(12) United States Patent
Berrido et al.

(10) Patent No.: US 9,493,728 B2
(45) Date of Patent: Nov. 15, 2016

(54) MICROPARTICLES AND METHOD OF MAKING MICROPARTICLES

(75) Inventors: Colin Berrido, Surrey (GB); Peter Rabke, Bevern (DE); Hans-Jurgen Huppert, Leipzig (DE)

(73) Assignee: BELL FLAVORS & FRAGRANCES DUFT UND AROMA GMBH, Leipzig (DE)

( * ) Notice: Subject to any disclaimer, the term of this patent is extended or adjusted under 35 U.S.C. 154(b) by 0 days.

(21) Appl. No.: 13/376,435

(22) PCT Filed: Jun. 24, 2010

(86) PCT No.: PCT/GB2010/001229
§ 371 (c)(1),
(2), (4) Date: Feb. 29, 2012

(87) PCT Pub. No.: WO2010/149966
PCT Pub. Date: Dec. 29, 2010

(65) Prior Publication Data
US 2012/0148636 A1 Jun. 14, 2012

(30) Foreign Application Priority Data
Jun. 24, 2009 (GB) .................................. 0910931.5

(51) Int. Cl.
| | |
|---|---|
| *A61K 8/04* | (2006.01) |
| *A61K 8/34* | (2006.01) |
| *C11D 3/18* | (2006.01) |
| *A61K 8/02* | (2006.01) |
| *A61Q 19/00* | (2006.01) |
| *C11D 3/20* | (2006.01) |
| *C11D 3/37* | (2006.01) |
| *C11D 3/384* | (2006.01) |
| *C11D 17/00* | (2006.01) |
| *C11D 3/50* | (2006.01) |

(52) U.S. Cl.
CPC ............... *C11D 3/18* (2013.01); *A61K 8/0245* (2013.01); *A61K 8/342* (2013.01); *A61Q 19/00* (2013.01); *C11D 3/201* (2013.01); *C11D 3/3719* (2013.01); *C11D 3/3765* (2013.01); *C11D 3/384* (2013.01); *C11D 3/505* (2013.01); *C11D 17/0013* (2013.01); *A61K 2800/56* (2013.01); *A61K 2800/652* (2013.01)

(58) Field of Classification Search
None
See application file for complete search history.

(56) References Cited

U.S. PATENT DOCUMENTS

| | | |
|---|---|---|
| 3,971,749 A | 7/1976 | Blunt |
| 4,152,272 A | 5/1979 | Young |
| 4,948,056 A * | 8/1990 | D'Errico ............... B02C 17/166 241/261.1 |
| 5,084,506 A | 1/1992 | Faler et al. |
| 5,096,493 A | 3/1992 | Hyche et al. |
| 5,155,156 A | 10/1992 | Scanley |
| 5,214,080 A | 5/1993 | Iwamura et al. |
| 5,250,586 A | 10/1993 | Scanley |
| 5,624,996 A | 4/1997 | Morinaga et al. |
| 5,929,162 A | 7/1999 | Horne et al. |
| 5,959,020 A | 9/1999 | Oliveri et al. |
| 5,998,542 A | 12/1999 | Horne et al. |
| 6,042,792 A | 3/2000 | Shefer et al. |
| 6,051,540 A | 4/2000 | Shefer et al. |
| 6,063,365 A | 5/2000 | Shefer et al. |
| 6,142,398 A | 11/2000 | Shefer et al. |
| 6,147,046 A | 11/2000 | Shefer et al. |
| 6,156,826 A | 12/2000 | Guenin et al. |
| 6,200,949 B1 | 3/2001 | Reijmer et al. |
| 6,235,274 B1 | 5/2001 | Lou et al. |
| 6,291,371 B1 | 9/2001 | Shefer et al. |
| 6,291,563 B1 | 9/2001 | Horne et al. |
| 6,368,633 B1 | 4/2002 | Lou et al. |
| 6,426,055 B1 | 7/2002 | Shefer et al. |
| 6,491,902 B2 | 12/2002 | Shefer et al. |
| 6,531,444 B1 | 3/2003 | Shefer et al. |
| 6,565,873 B1 | 5/2003 | Shefer et al. |
| 6,589,562 B1 | 7/2003 | Shefer et al. |
| 6,613,827 B2 | 9/2003 | Lundgard et al. |
| 6,645,479 B1 | 11/2003 | Shefer et al. |
| 6,703,011 B2 | 3/2004 | Shefer et al. |
| 6,740,631 B2 | 5/2004 | Shefer et al. |
| 6,743,756 B2 | 6/2004 | Harris, Jr. |

(Continued)

FOREIGN PATENT DOCUMENTS

| | | |
|---|---|---|
| EP | 0 455 073 A1 | 11/1991 |
| EP | 0 465 001 A1 | 1/1992 |
| EP | 0 466 310 A1 | 1/1992 |
| EP | 0 733 666 A2 | 9/1996 |
| EP | 0 896 016 A2 | 2/1999 |
| EP | 0 908 174 A2 | 4/1999 |
| EP | 0 964 023 A2 | 12/1999 |
| EP | 1 057 867 B1 | 4/2005 |

(Continued)

OTHER PUBLICATIONS

Search Report dated Jul. 23, 2010, for Application No. GB0910931.5.
Search Report dated Oct. 14, 2010 for Application No. PCT/GB2010/001229.
Office Action dated Aug. 10, 2015 for Application No. EP 10 731 551.7-1358.

*Primary Examiner* — Jessica Worsham
(74) *Attorney, Agent, or Firm* — Ladas & Parry LLP

(57) ABSTRACT

A process for producing micronized dispersed micro-particles and to micro-particles produced by this process. In the process a combination of a dispersion liquid, an active ingredient and a wax is passed at a temperature at which the wax is molten into a high energy micro-particle producing machine operating at a temperature at which the active ingredient and wax are kept molten and producing a composition comprising a plurality of micro-particles dispersed in said dispersion liquid by cooling said combination to a temperature below the solidification temperature of each of said micro-particles before each said micro-particle leaves said micro-particle producing assembly.

31 Claims, 41 Drawing Sheets

(56) References Cited

U.S. PATENT DOCUMENTS

| | | |
|---|---|---|
| 6,790,460 B2 | 9/2004 | Shefer et al. |
| 6,818,597 B2 | 11/2004 | Harris |
| 6,825,161 B2 | 11/2004 | Shefer et al. |
| 6,887,493 B2 | 5/2005 | Shefer et al. |
| 6,979,440 B2 | 12/2005 | Shefer et al. |
| 7,053,034 B2 | 5/2006 | Shefer et al. |
| 7,067,152 B2 | 6/2006 | Shefer et al. |
| 7,084,096 B2 | 8/2006 | Harris, Jr. et al. |
| 7,115,282 B2 | 10/2006 | Shefer et al. |
| 7,119,060 B2 | 10/2006 | Shefer et al. |
| 7,208,460 B2 | 4/2007 | Shefer et al. |
| 7,214,382 B2 | 5/2007 | Shefer et al. |
| 7,338,928 B2 | 3/2008 | Lau et al. |
| 7,670,627 B2 | 3/2010 | Shefer et al. |
| 7,691,986 B2 | 4/2010 | Ni et al. |
| 7,705,135 B2 | 4/2010 | Ni et al. |
| 7,803,838 B2 | 9/2010 | Davis et al. |
| 2002/0146379 A1 | 10/2002 | Shefer et al. |
| 2003/0203829 A1 | 10/2003 | Shefer et al. |
| 2006/0058437 A1 | 3/2006 | Martin et al. |
| 2006/0116524 A1* | 6/2006 | Bruening et al. ............ 554/166 |
| 2006/0188551 A1 | 8/2006 | Hauser et al. |
| 2007/0081954 A1 | 4/2007 | Mougin et al. |
| 2008/0160290 A1 | 7/2008 | Park et al. |
| 2010/0143479 A1 | 6/2010 | Thanoo et al. |
| 2010/0209512 A1 | 8/2010 | Driscoll et al. |

FOREIGN PATENT DOCUMENTS

| | | |
|---|---|---|
| GB | 986911 | 3/1965 |
| WO | 96/39461 A1 | 12/1996 |
| WO | 98/33864 A1 | 8/1998 |
| WO | 99/10416 A1 | 3/1999 |
| WO | 02/04004 A1 | 1/2002 |
| WO | 2004/062630 A1 | 7/2004 |
| WO | 2006/078541 A1 | 7/2006 |
| WO | 2010/072711 A1 | 7/2010 |

* cited by examiner

200 µm

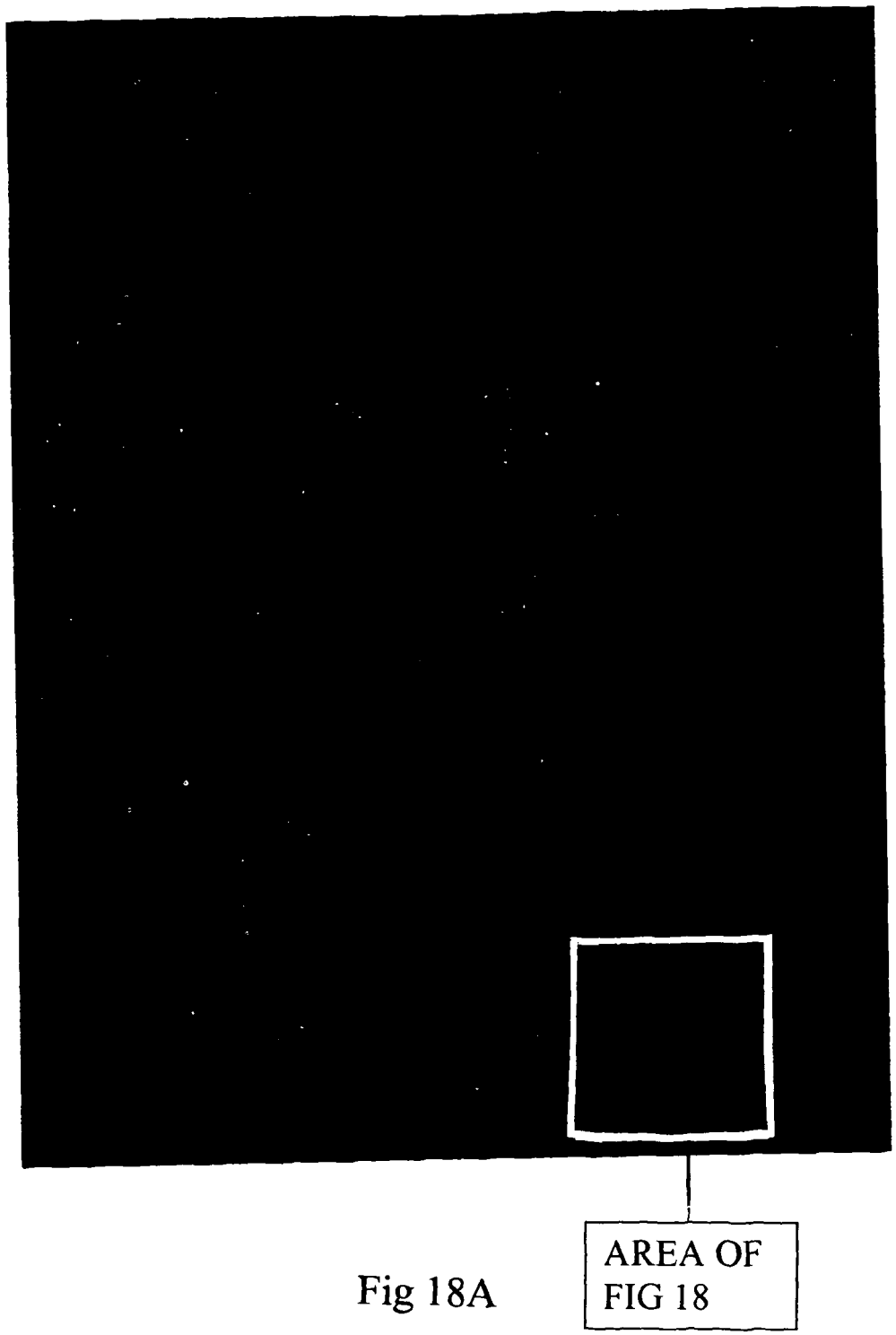
Fig 18A  |  AREA OF FIG 18

100 μm

MICROPARTICLES AND METHOD OF MAKING MICROPARTICLES

The present invention relates to a method for making micro-particles containing actives, and to novel compositions comprising the micro-particles containing the actives. These novel compositions are well suited for use in various applications e.g. personal care applications, laundry products and fragrance products.

Encapsulation of actives e.g. fragrances is well known in the art. Encapsulation provides advantages to the active including the protection of the active in the capsule matrix until the active is intended to be delivered. In particular, capsules are often designed to deliver their contents at a desired time by the capsule being compromised after a desired period. The capsule can be compromised by various factors such as mechanical fracture or by melting or dissolving the encapsulating material to release the contents when desired. Other types of carriers for actives such as fragrances are known such as Bell MikroChips® pastilles where the active is protected by being dispersed throughout the matrix of a non-frangible composition until the active is required to be released. Bell MikroChips® pastilles are commercially available and are used to carry/protect liquid fragrances before the liquid fragrances are released. Liquid fragrances can present particular challenges in use for example in that they are relatively unstable being relatively easily oxidized. Bell MikroChips® pastilles are characterized by having a matrix formed by a C22 fatty alcohol and are commercially available in 2-7 mm pastille format or block form. Bell MikroChips® pastilles have been found to be extremely efficient carriers for fragrances etc in that they can carry high amounts of liquid fragrance typically up to 60 weight percent, with the carrier protecting the liquid fragrance from oxidation very well and in that they have super long life (only losing about 5% of the fragrance over a storage period of about 6 months).

From a practical standpoint this means that significant release of the fragrance does not occur at room temperature but increases with increasing temperature up to its melting point of around 65° C. when the C22 fatty alcohol matrix melts thus effecting substantial release. This release profile means the use of Bell MikroChips® pastilles is best suited to applications where release is achieved by the input of heat energy as detailed in EP Patent Publication No. EP 1 627 647 A1 Air Treatment Apparatus etc., Berrido et al. However, Bell MikroChips® pastilles are not an ideal system for rapid delivery of actives at lower temperatures for example at temperatures around human body temperature (e.g. at temperatures of about 37° C.). It is obviously not desired that the active be released too easily from the matrix such that the active releases prematurely. On the other hand it is also not desired that the active is too hard to release such that the active cannot be released when required. What is required is a good balance of properties such that the active releases when needed, yet the active is adequately protected.

It has now been unexpectedly discovered that a very small micro-particle can be produced which unexpectedly solves the problem of the difficulty of release whilst surprisingly retaining the advantages of the larger known non-frangible compositions (e.g. Bell MikroChips® pastilles) of providing good carrying capacity e.g. carrying high amounts of liquid fragrance with good fragrance protection. No one would have expected that any carrying/protecting effect at all could be retained after the larger carriers (e.g. Bell MikroChips® pastilles) were size reduced down to micro-particles having a particle size of 0.1-20 micrometers in the high energy environment of a high shear micro-particle producing machine e.g. a colloid mill. Yet, surprisingly, these advantages are retained in the micro-particles of the present invention.

Furthermore the small particle size of the micro-particles provides a remarkable and totally unexpected improvement in the speed of the release of the active even at temperatures of around human body temperature (e.g. about 37° C.), thus permitting the fragrance to be released at the relatively low temperatures where fragrance release is required in many commercial applications. Thereby the problem of the larger carriers having particle size of for example 3 mm (e.g. Bell MikroChips®) of difficult fragrance release is unexpectedly overcome with the additional unexpected effect that the good properties of the larger carriers of high fragrance loading and good protection of the fragrance are retained. The advantage of easy active release is especially important where the amount of heat available for effecting release of the active is limited, e.g., as in consumer products for personal use, where release is affected by body heat. For many personal use compositions such as drugs, foods, etc., the release of active should be as quick and easy as possible with release occurring at low temperatures around body temperature. Easy release in many instances is necessary to provide a concentration of the active that will provide the desired effect at the low temperature and in other instances is necessary to avoid the use of excessive amounts of fragrance carrier. U.S. Pat. No. 4,152,272 discloses fabric conditioning compositions that contain particles of size 0.1 to 200 microns and of melting point 38° C. to 150° C. and comprising a wax-like carrier substance and a perfume.

Accordingly in one aspect the present invention provides a composition comprising a plurality of the micro-particles and a dispersion liquid in which said micro-particles are dispersed, each said micro-particle comprising a wax or wax-like dispersion matrix with an active dispersed therein, at least a majority of said micro-particles having a particle size of from 0.1 to 20 micrometers, the wax of said wax or wax like dispersion matrix being a solid at a temperature of 21° C., and wherein said plurality of micro-particles dispersed in said dispersion liquid are present in said dispersion liquid in an amount of above 20 weight percent, more preferably from 21 to 60 weight percent, yet more preferably from 25 to 60 weight percent, even more preferably 35 to 60 weight percent, yet more preferably 40 to 60 weight percent, even more preferably 21 to 40 weight percent, yet more preferably 21 to 30 weight percent.

In another aspect the subject invention provides a process of preparing a composition comprising a plurality of micro-particles and a dispersion liquid in which said micro-particles are dispersed comprising the steps of:

providing a high energy micro-particle producing machine comprising a micro-particle producing assembly, providing a combination of a dispersion liquid, an active and a wax or wax like material at such a temperature that the active and the wax or wax-like components of the combination are melted;

passing said combination into said micro-particle producing assembly of said high energy micro-particle producing machine whilst said micro-particle producing assembly is operating at such a temperature that said active and said wax or wax-like components of the combination are kept melted then while said micro-particle producing assembly is kept operating producing a composition comprising a plurality of micro-particles dispersed in said dispersion liquid by cooling said combination to a temperature below the solidification temperature of each of said micro-particles before each said micro-particle leaves said micro-particle producing assembly, each said micro-particle comprising a wax or wax-like dispersion matrix with said active dispersed therein.

High energy micro-particle producing machines suitable for use in the present invention include those that can produce a smooth creamy dispersion of solid wax particles wherein at least 50% of said particles have a particle size in the range 0.1-20 micrometers from a combination comprising 10% by weight molten wax in an aqueous medium containing a surface tension lowering agent to lower the surface tension to below 30 dynes/cm, when solidification is carried out.

Preferably in the above process when said active and said wax or wax-like components of the combination are melted or kept melted it is not desirable to heat the combination to such a high temperature that the active is subjected to temperature stress. This temperature stress arises where the active is subjected to unnecessarily high temperatures. For example in a case where the active is a relatively volatile perfume subjecting the perfume to an unnecessarily high temperature can result in loss of the perfume where the perfume volatizes and is driven away. Accordingly in the above process said active and said wax or wax-like components of the combination are melted or kept melted preferably by heating to a temperature from 40° C. to 115° C., more preferably from 45° C. to 90° C., yet more preferably from 55° C. to 90° C., even more preferably from 55° C. to 80° C. to avoid volatizing the active.

Preferred embodiments of the invention are described below by way of example only wherein:

FIG. 18A shows the full photomicrograph of FIG. 18.

Figure 22:
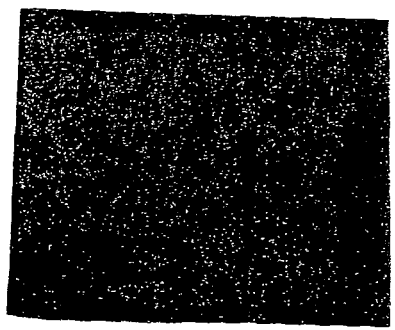

FIG. 22 a photomicrograph showing micro-particles of the composition of the invention produced by the method of Example 5 herein.

Figure 23:
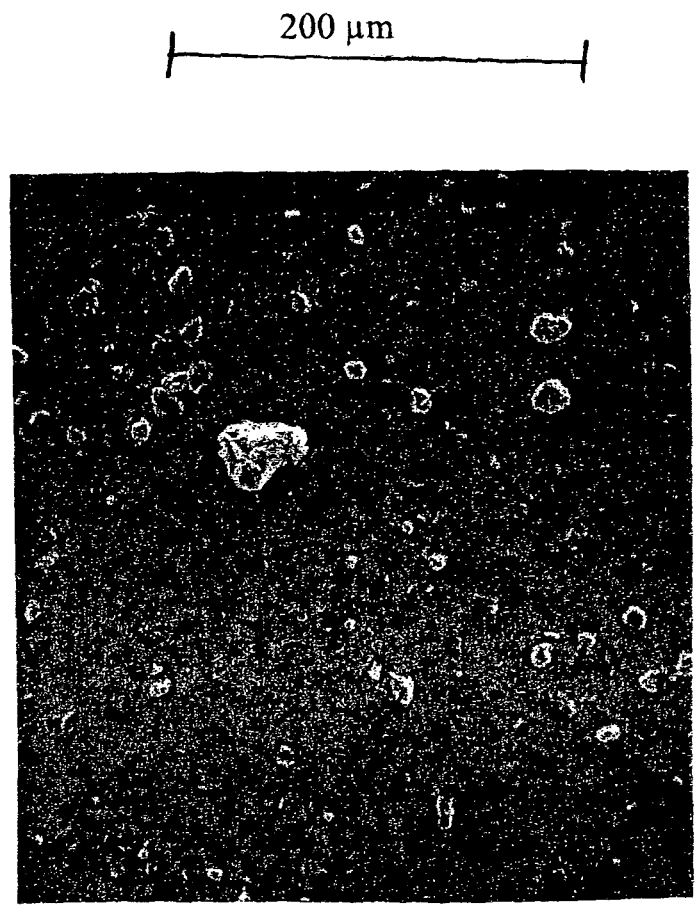

FIG. 23 is an electronmicrograph with a 200 micrometer scale line marked on the electronmicrograph showing micro-particles of the composition of the invention produced by the method of Example 5 herein.

Figure 24:
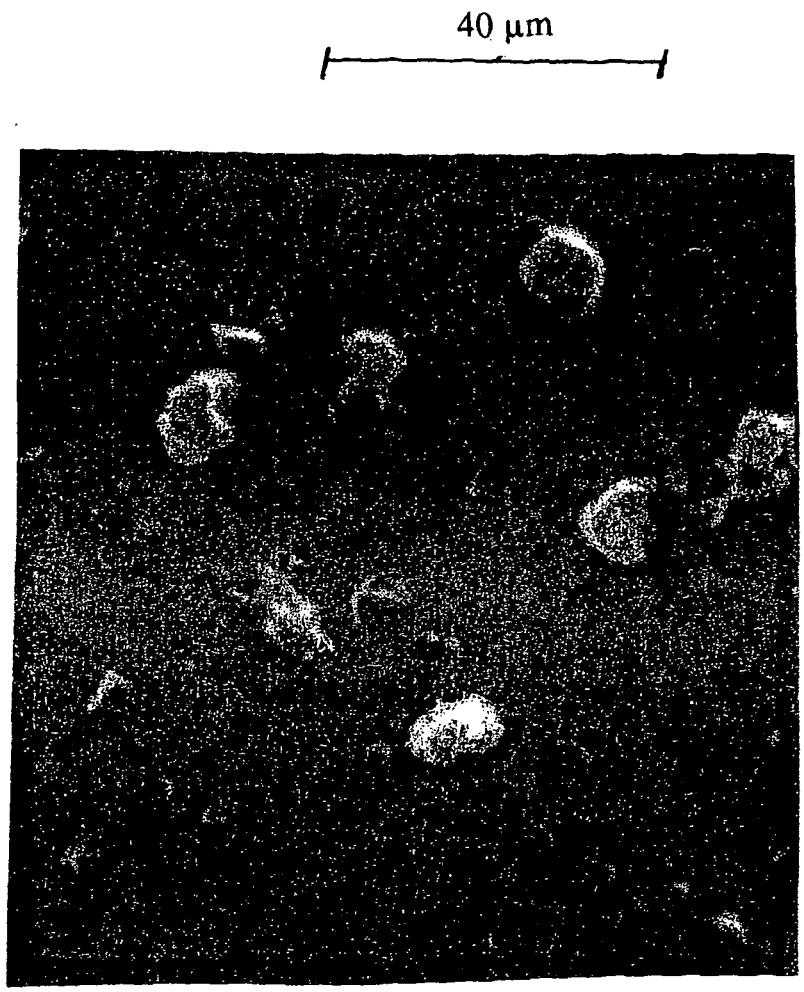

FIG. 24 is an electronmicrograph with a 40 micrometer scale line marked on the electronmicrograph showing micro-particles of the composition of the invention produced by the method of Example 5 herein.

Figure 25:
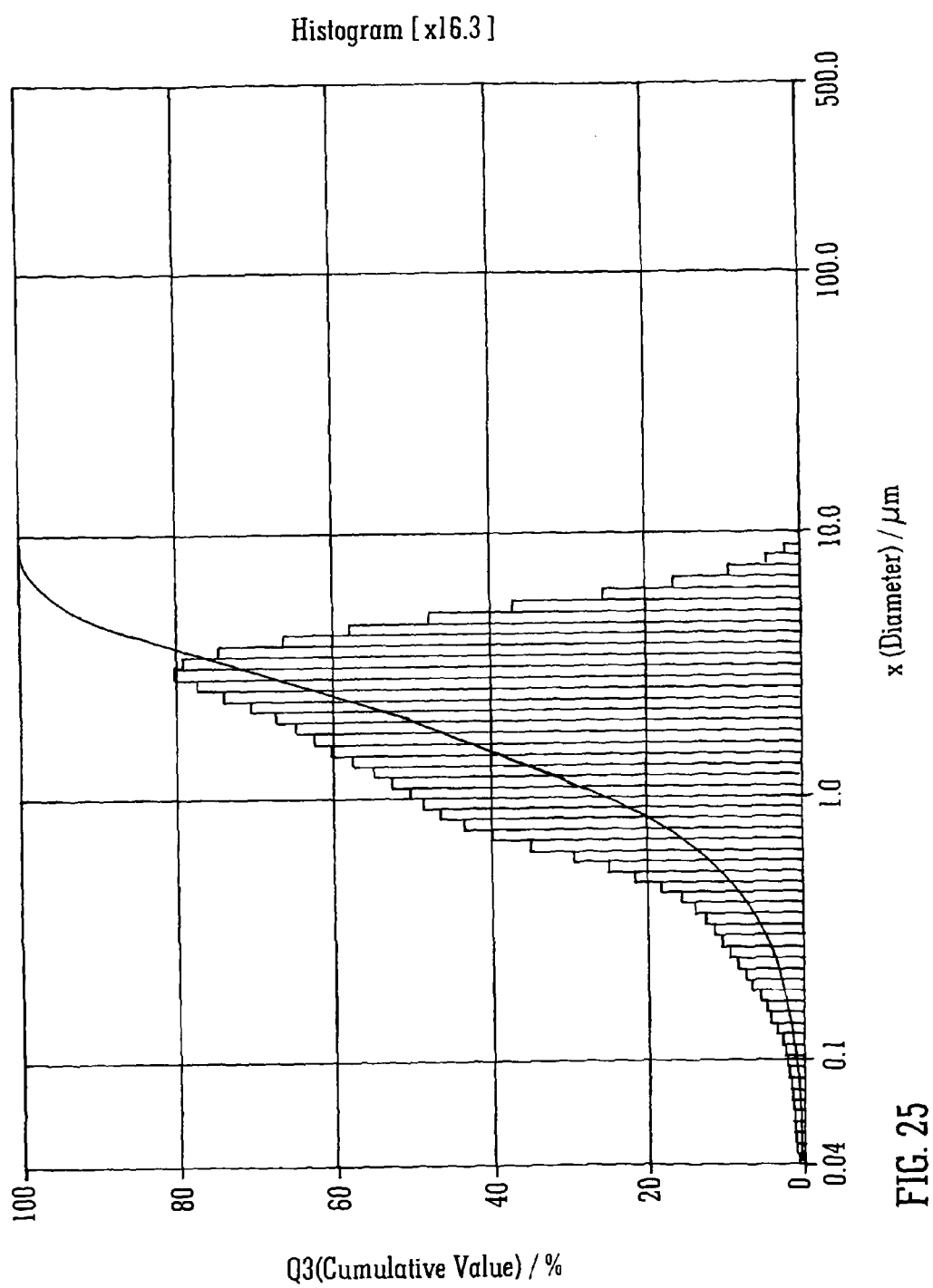

FIG. 25 is a size distribution curve of the micro-particles of the composition of the invention produced by the method of Example 5 herein.

Figure 26:
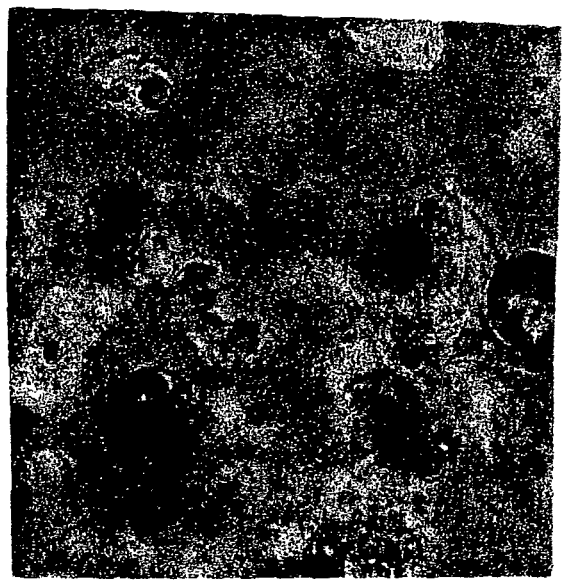

FIG. 26 shows a cut out part of a photomicrograph (magnification 400 fold) showing micro-particles of the composition of the invention produced by the method of Example 6 herein.

Figure 26A:
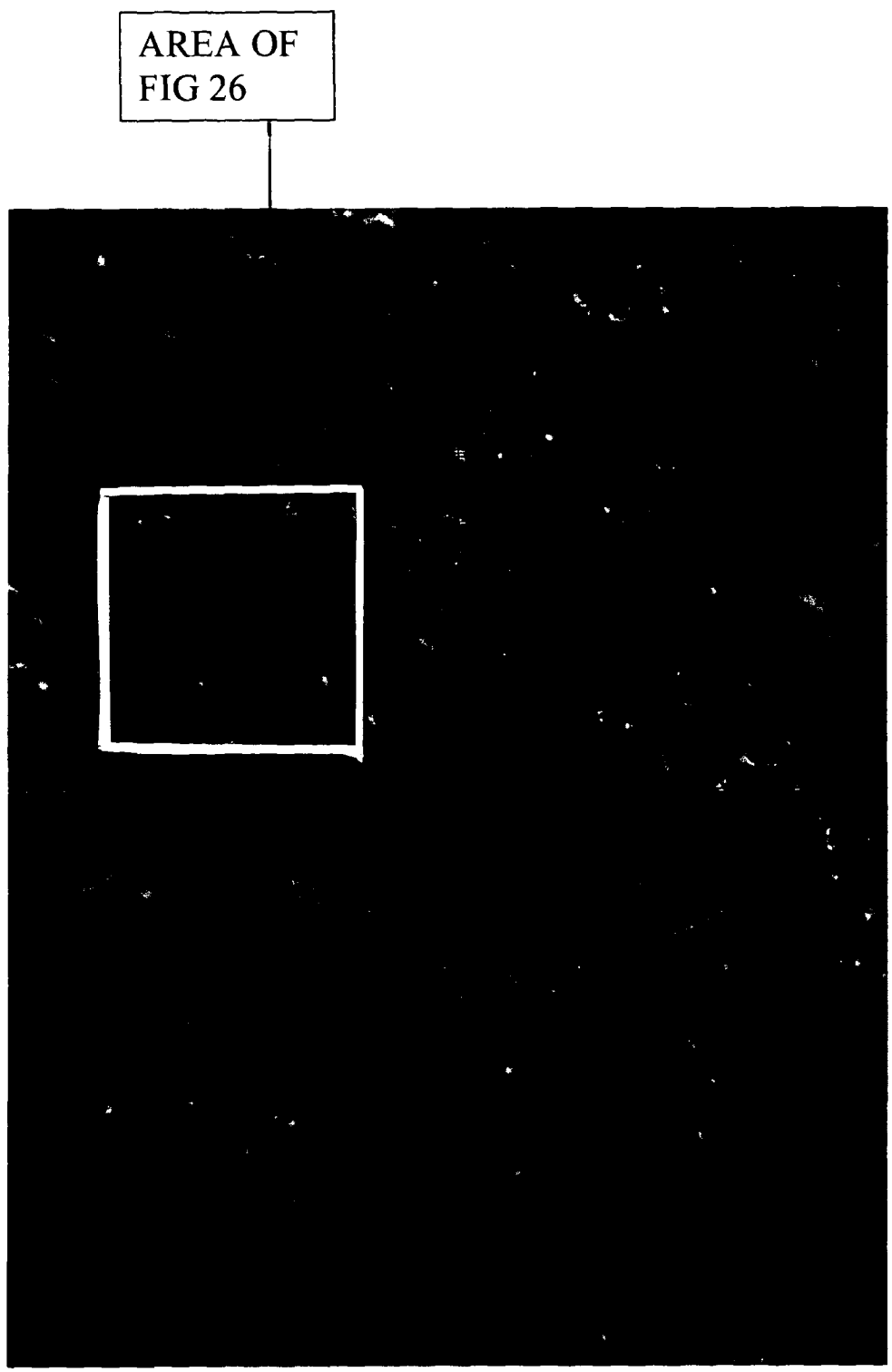

FIG. 26A shows the full photomicrograph of FIG. 26.

Figure 27:
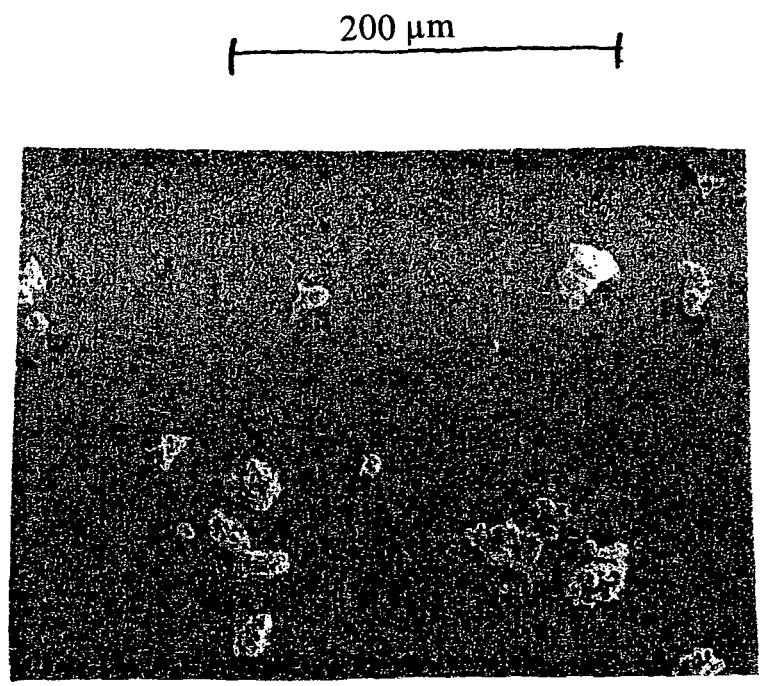

FIG. 27 is an electronmicrograph with a 200 micrometer scale line marked on the electronmicrograph showing micro-particles of the composition of the invention produced by the method of Example 6 herein.

Figure 28:
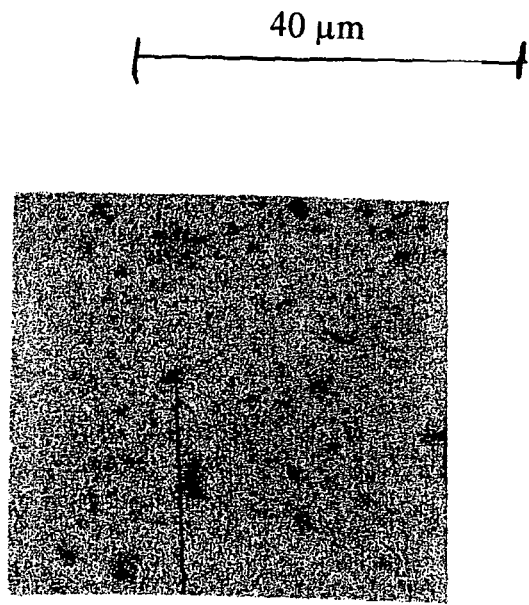

FIG. 28 is an electronmicrograph with a 40 micrometer scale line marked on the electronmicrograph showing micro-particles of the composition of the invention produced by the method of Example 6 herein.

Figure 29:
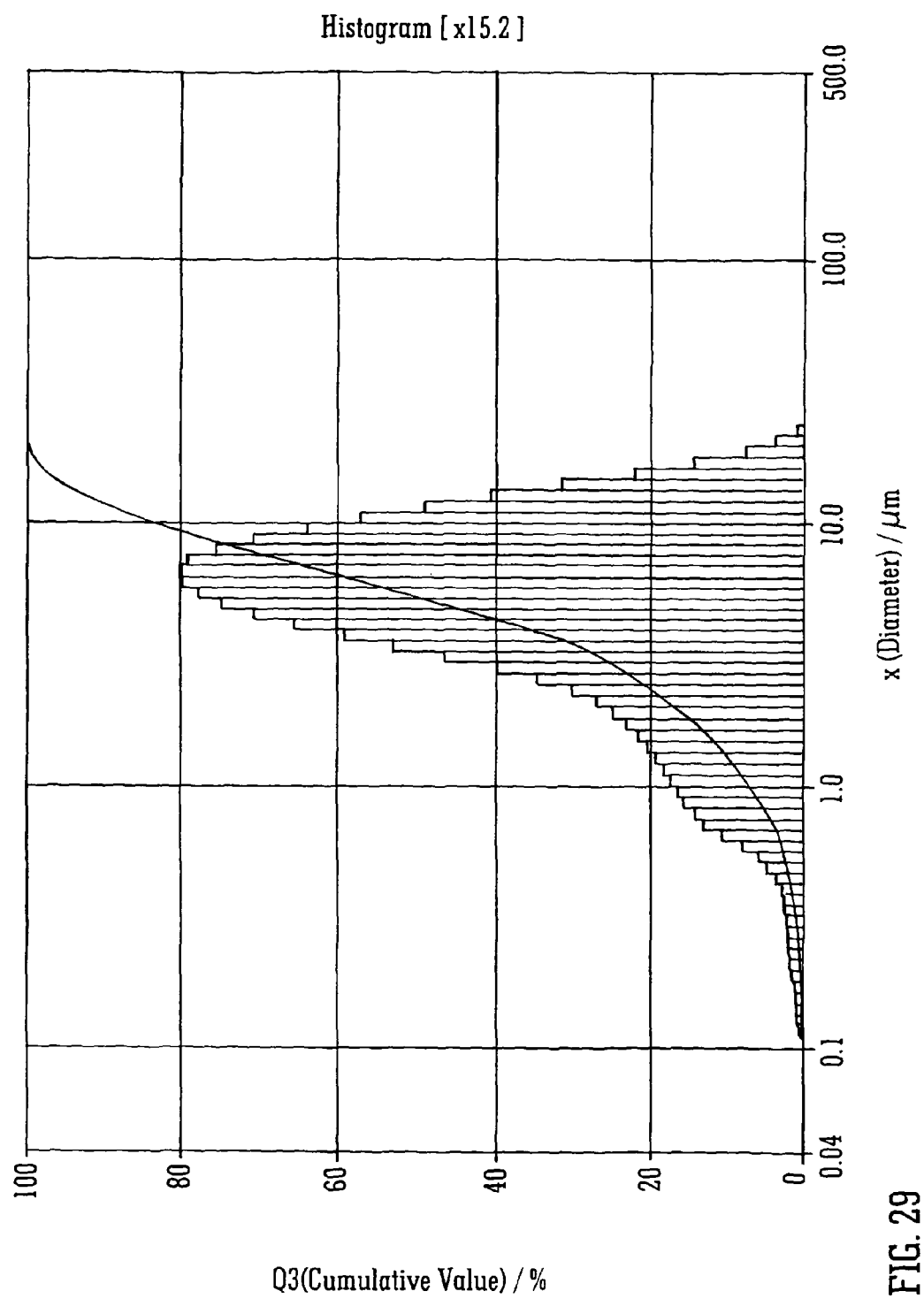

FIG. 29 is a size distribution curve of the micro-particles of the composition of the invention produced by the method of Example 6 herein.

Figure 30:

FIG. 30 shows a composition (which is a product of the invention) comprising a plurality of the micro-particles of the composition of the invention and a dispersion liquid in which said micro-particles are dispersed.

Figure 31:
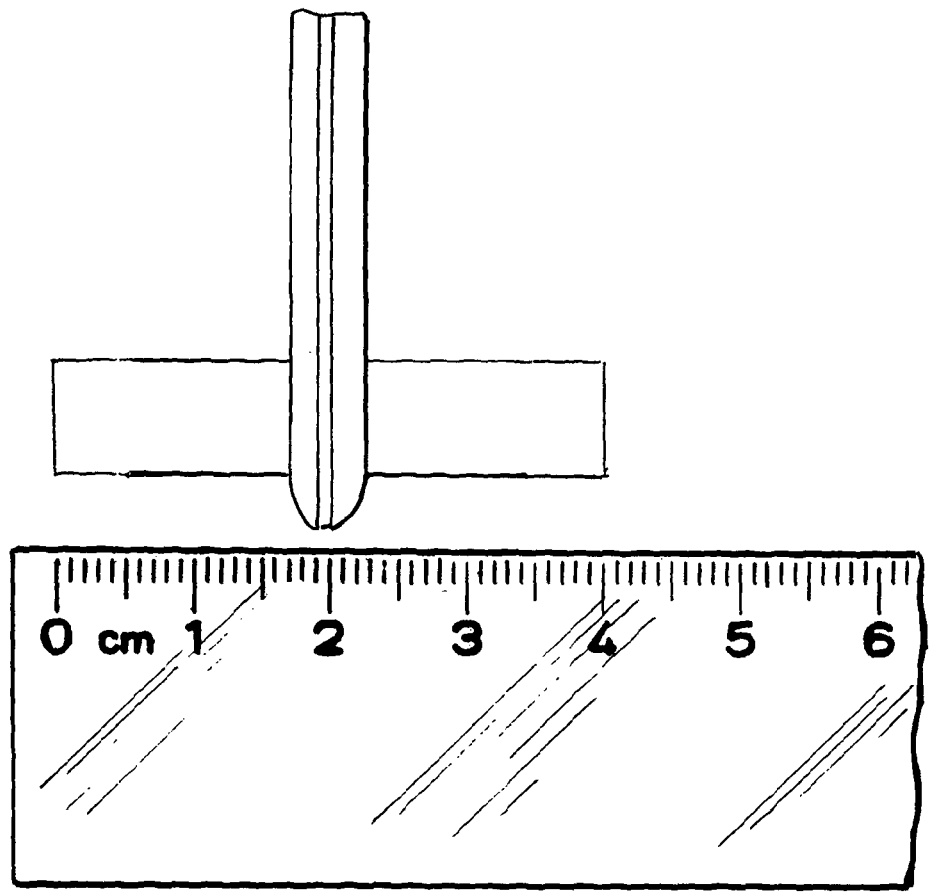

FIG. 31 shows an ordinary paddle like mixing means of the type used in low energy impeller type laboratory mixers.

Figure 32:
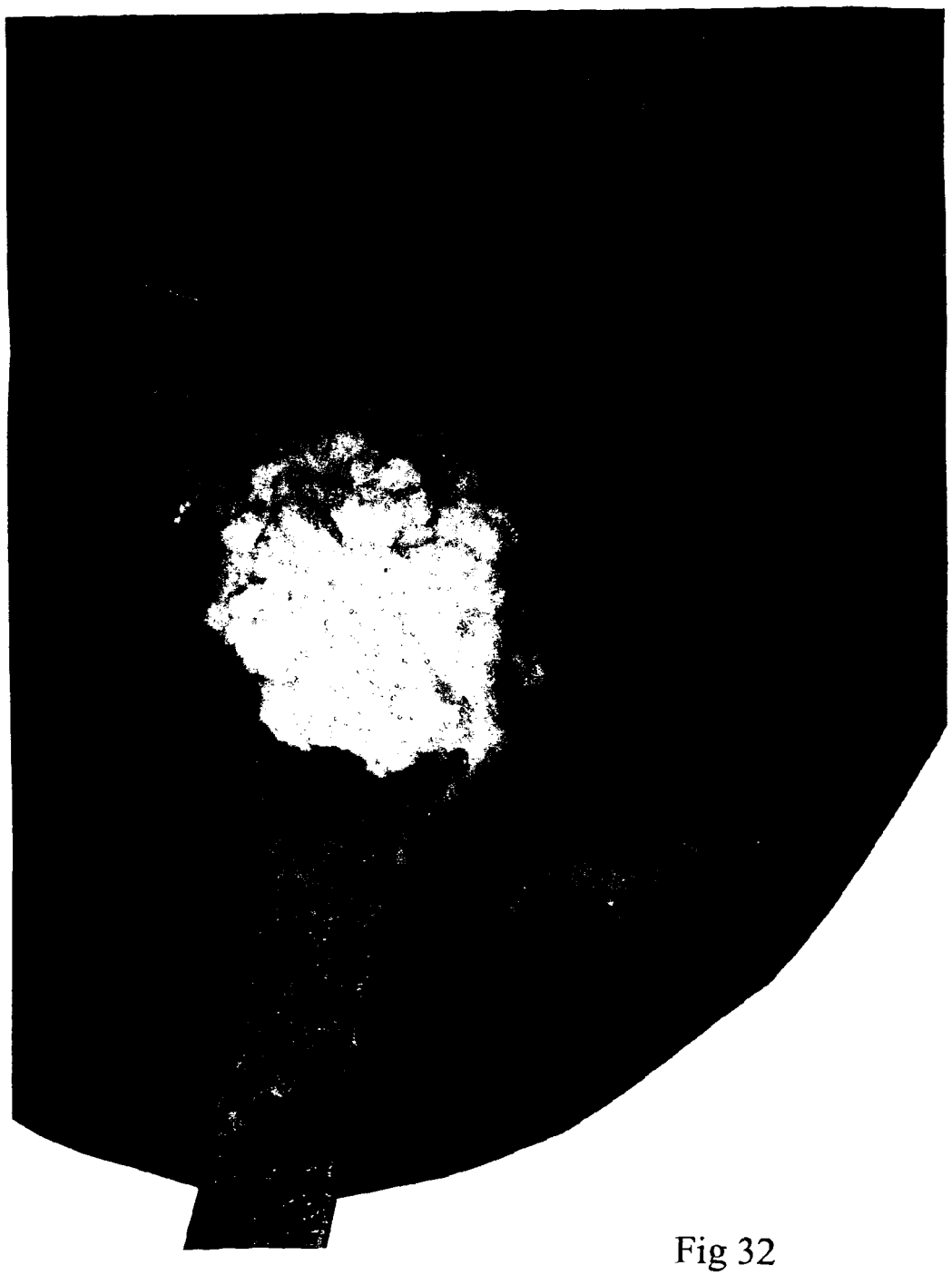

FIG. 32 shows the composition which results when the process of the invention is carried out with a low energy impeller type laboratory mixer.

Figure 33:

FIG. 33 shows a photomicrograph (magnification 400 fold) showing micro-particles of the composition of the invention produced by the method of Example 7 herein.

Figure 34:

FIG. 34 shows a photomicrograph (magnification 400 fold) showing micro-particles of the composition of the invention produced by the method of Example 8 herein.

Figure 35:
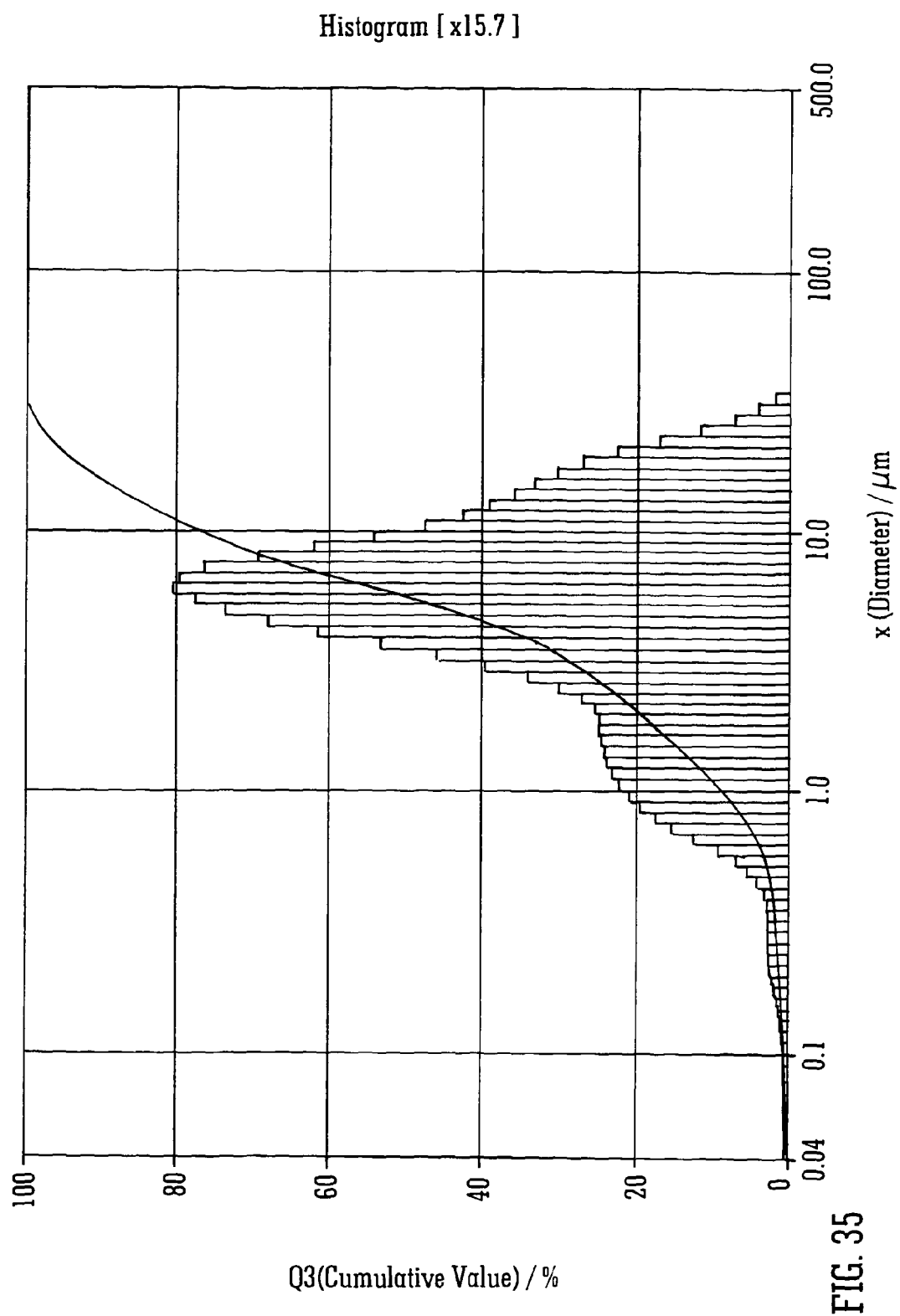

FIG. 35 is a size distribution curve of the micro-particles of the composition of the invention produced by the method of Example 7 herein.

Figure 36:
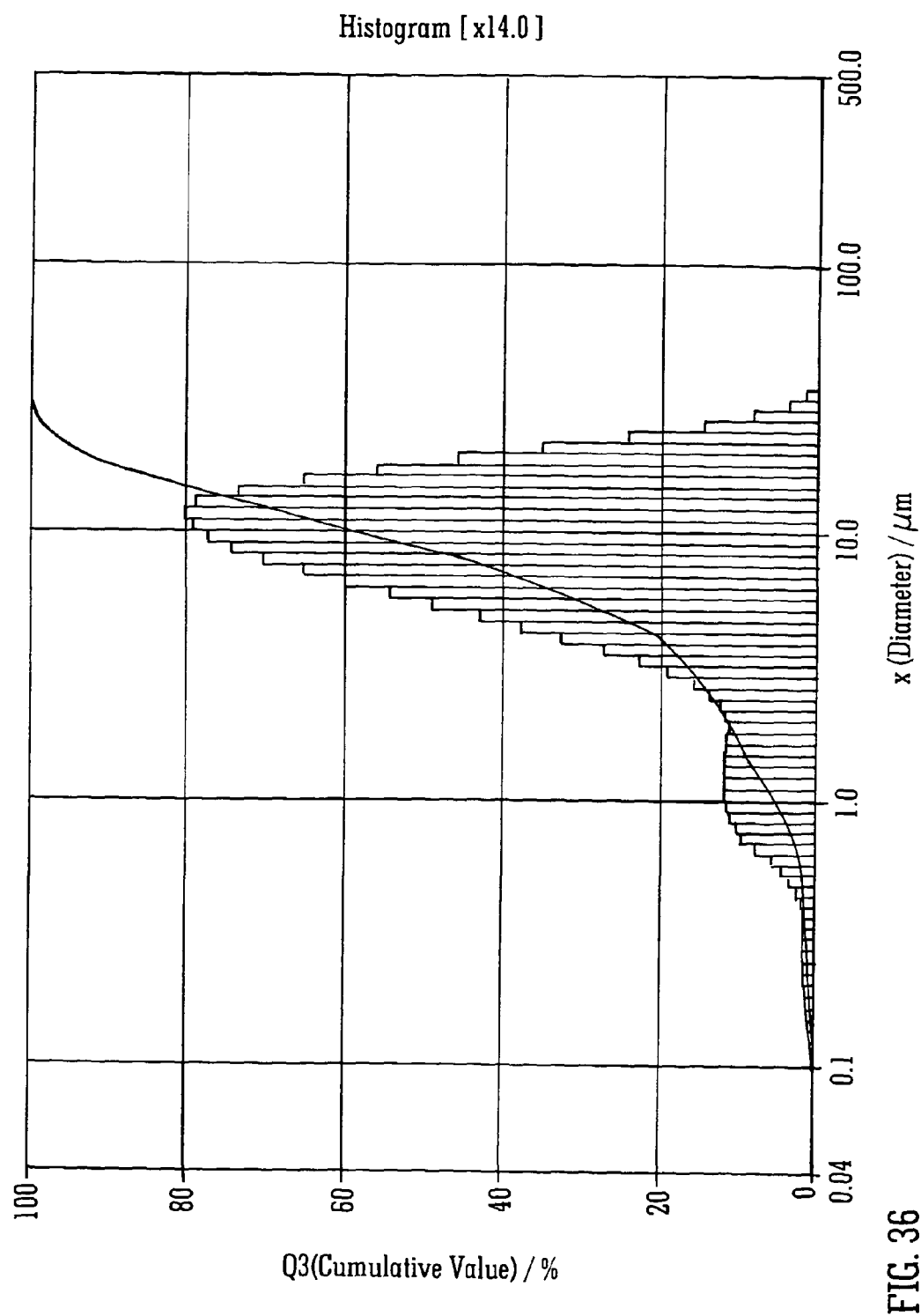

FIG. 36 is a size distribution curve of the micro-particles of the composition of the invention produced by the method of Example 8 herein.

Frangible microcapsules are well understood by the skilled addressee to mean microcapsules comprising an outer breakable shell formed for example from an aminoplast polymer encapsulating a core of an active for example a liquid fragrance wherein the frangible microcapsules can break and release the encapsulated perfume under the action of a certain bursting force or a certain bursting pressure. WO 2008/098387 for example describes frangible microcapsules comprising a core of a fragrance and a shell of aminoplast polymer and describes that its microcapsules are useful for the storage and dissemination of fragrance in products such as laundry products. WO 2008/098387 describes its microcapsules as being highly frangible and describes highly frangible as meaning the ability of its dry microcapsules to break and release the encapsulated perfume under the action of a normal bursting force not superior to 9 mN for microcapsules having a diameter of 60 micrometers and not superior to 3 mN for microcapsules having a diameter of 35 micrometers and describes that these bursting forces correspond to a bursting pressure not higher than 6×106 MPa. WO 2008/098387 then describes that both bursting force and bursting pressure may be measured by various methods, such as a nano-indentation test, as described in Example 3 of WO 2008/098387, or an osmotic rupture test. The on-line encyclopedia Wikipedia discloses that a material is said to be frangible if through deformation it tends to break up into fragments, rather than deforming plastically and retaining its cohesion as a single object and then describes that common cookies or crackers are examples of frangible materials, while fresh bread, which deforms elastically is not frangible. This definition is consistent with the above description of frangible microcapsules it being noted that frangibility is a function of temperature e.g. whilst fresh bread, which deforms elastically is not frangible at room temperature it may become frangible when frozen.

The micro-particles of the composition of the subject invention are non-frangible which means that they do not release their active e.g. liquid perfume through the breaking of an outer shell under the action of a outer shell breaking force or pressure but instead normally (i.e at temperatures around ambient and above e.g. at about 21° C. and above but not at super cold temperatures) do through deformation tend to deform plastically retaining their cohesion as a single object and do tend to release their active e.g. perfume to their exterior along a diffusion pathway through the action of heat.

Bell MikroChips® pastilles have pastille size of about 3 mm and are commercially available from Bell Flavors and Fragrances-Europe, Schimmel-Strasse1. 04205, Leipzig (Miltitz), Germany. Bell MikroChips® pastilles can be prepared in accordance with methods described in European Patent EP 1 549 729 B1 the disclosures of which are incorporated herein by reference. The solid commercially available Bell MikroChips® pastilles have a dispersion matrix portion formed of a C22 fatty alcohol with a fragrance as the active dispersed therein. The melting temperature of the C22 fatty alcohol component of the Bell MikroChips® pastilles composition is around 65.

Wax or wax like materials that can be used in the subject process and which are contained in the subject composition are well known to the skilled addressee. The Penguin Dictionary of Chemistry copyright 1983 by D.W.A Sharp defines waxes as 'formally fatty acid esters with monohydric fatty alcohols having wax like properties but now arbitrarily extended to any organic material having such properties' and further indicates 'waxes are water repellant and have plasticity'. A description of such wax or wax like materials is also given in the book "Chemistry and Technology of Waxes" A. H. Warth Second Edition, 1960, incorporated herein by reference. U.S. Pat. No. 4,152,272 as mentioned above also discloses micro-particles comprising a wax like substance. Wax or wax like materials that can be used in the present invention include macro- and microcrystalline hydrocarbon waxes, derived from petroleum or made synthetically, ester waxes such as bees wax, carnauba wax, ozokerite; fatty acid esters of mono- or polyhydric alcohols; hardened fatty acids and hydroxy fatty acids; higher monohydric alcohols. The microcrystalline waxes and the Fischer-Tropsch waxes described below are also suitable.

Some suitable microcrystalline waxes include:

Microcrystalline wax 160/165 sold by Shell Chemicals

Microcrystalline wax 185/190 sold by Shell Chemicals (the numerical ranges are believed to represent the melting point ranges—DEG F.)

Microcrystalline wax 160/25 Y sold by BP Chemicals

Microcrystalline wax OK239 sold by Astor Chemicals Ltd.

Mobilwax 2305 sold by Mobil Oil Company Limited, and

Mobilwax 2360 sold by Mobil Oil Company Limited

Witcodur 263 Mpt. 83 DEG-89 DEG C. sold by Witco Chemicals (Holland)

Witcodur 272 Mpt. 83 DEG-89 DEG C. sold by Witco Chemicals (Holland)

Witcodur 143 Mpt. 79 DEG-84 DEG C. sold by Witco Chemicals (Holland)

Witcodur 145 Mpt. 78 DEG-83 DEG C. sold by Witco Chemicals (Holland)

Witcodur 146 Mpt. 70 DEG-75 DEG C. sold by Witco Chemicals (Holland)

Fischer Tropsch waxes, such as those sold by Veba Chemie, AG, are also suitable, for example VEBA wax SP 1044 (melting point about 106 DEG-111 DEG C.). Macrocrystalline hydrocarbon waxes, such as high melting paraffin wax, are also useful in the present invention.

A great variety of waxy esters are also suitable. These include the naturally derived ester waxes, preferably those with low saponification value, that is not exceeding 100, preferably below 60. Also suitable, provided that they are chosen as having high enough melting point when mixed with the active e.g. perfume are fatty acid esters and partial esters of mono- and polyhydric alcohols or anhydrides thereof, said alcohols or anhydrides having 1 to 8 carbon atoms. These fatty acid esters and partial esters are more fully described in the German Offenlegungsschrift No. 26 31 114. These materials are fatty acid esters of mono- or polyhydric alcohols or anhydrides having from 1 to 8 carbon atoms. It is preferred that the fatty acid ester should have at least 1, more preferably 2, free (i.e. unesterified) hydroxyl groups and at least 1, more preferably at least 2 fatty acyl groups.

The mono- or polyhydric alcohol portion of the ester can be represented by methanol, isobutanol, 2-ethylhexanol, isopropanol, ethylene glycol and polyethylene glycol with a maximum of 5 ethylene glycol units, glycerol, diglycerol, xylitol, erythritol, pentaerythritol, sorbitol or sorbitan. Ethylene glycol, glycerol and sorbitan esters are particularly preferred. The fatty acid portion of the ester normally comprises a fatty acid having from 12 to 22 carbon atoms, typical examples being lauric acid, myristic acid, palmitic acid, stearic acid and behenic acid.

Specific useful fatty acid partial esters are xylitol monopalmitate, pentaerythritol mono-stearate, glycerol monostearate and ethylene glycol monostearate. As with the sorbitan esters, commercially available monoesters normally contain substantial quantities of di- or tri-esters.

Other preferred wax or wax like materials are fatty alcohols of about 16 carbon atoms upwards, more preferably having from 16-29 carbon atoms, yet more preferably 18-24 carbon atoms, even more preferably 22 carbon atoms such as octadecanol (C18), eicosanol (C20), and tallow alcohols. Higher nearly saturated fatty acids can also be used, for example palmitic, stearic, arachidic, hardened fatty acid from tallow or fish oils, or hydrogenated castor oil (known as castorwax). All these substances are commercially available. A table of physical properties of some common waxes is published in Soap & Chemical Specialties, December 1957, p. 141, and is hereby incorporated by reference.

Other preferred wax or wax like materials that can be used in the present invention are selected from ethylene-acrylic acid copolymer wax like materials; polyamide polymer wax like materials; polyethylene-vinyl acetate copolymer wax like materials, fatty alcohol wax like materials and a mixture of said fatty alcohol wax like materials with fatty acid(s) and/or fatty alcohol ethoxylate and/or polyethylene glycol. Yet other preferred wax or wax like materials that can be used in the subject invention are selected from wax like edible oils, wax like edible fats, petroleum based wax like materials and alkane hydrocarbons and mixtures thereof. Preferably the polyamide polymer wax like material has a molecular weight in the range of from about 6,000 up to about 12,000, and preferably the petroleum based wax like materials are selected from paraffinic waxes with chemical formula C2H2n+2 where n=30 or more and microcrystalline waxes produced from heavy lubricating oil residues having a microcrystalline structure. As mentioned preferably also each of the above fatty alcohols and the above fatty acids have 16-29, more preferably 18-24 carbon atoms. Preferably the above fatty alcohol ethoxylates have 10-29 carbon atoms, preferably 14-20 carbon atoms with there being present 5-100 moles of ethylene oxide in each case. Preferably also the above polyethylene glycols have a molecular weight of 10-30,000 g per mole, more preferably 15,000-25,000 g per mole. Mixtures of any one listed wax or wax like material with any other listed wax or wax like material can be used and every one listed wax or wax like material is herein expressly disclosed in combination with every other listed wax or wax like material.

Melting points of the micro-particles of the composition of the invention are measured by a capillary tube method, for instance the method of the American Oil Chemists Association (A.O.C.A.) Cc 1-25, incorporated herein by reference. The melting point of the micro-particles of the composition of the invention is usually a function of the wax or wax-like substance employed but it should be understood that it is the melting point of the micro-particle rather than of the wax or wax-like substance employed that is important since it is the micro-particle which is produced herein. The melting point of the micro-particles of the composition of the invention are preferably in the range from 38° C. to 150° C. more preferably from 65° C. to 100° C. The wax or wax like material used herein can be any substantially water-insoluble wax or wax like substance compatible with and miscible with an active as described herein (an example of the active being a perfume).

The term 'the dispersion matrix' as used herein for example with reference to the micro-particles of the subject invention has the same meaning as the term 'carrier substance' or 'carrier' as used in U.S. Pat. No. 4,152,272.

Actives that can be used in the subject process and which are contained in the subject composition are well known in the art and are listed below under the heading 'actives'. Preferably the active is selected from botanical extracts including essential oils, other perfumes and mixtures thereof. Alternative preferred actives are selected from flavours, pharmaceutical actives, insecticides and mixtures thereof. Mixtures of the said botanical extracts can be used. Mixtures of the said essential oils can be used. Mixtures of the said other perfumes can be used. Mixtures of the said flavours can be used. Mixtures of the said pharmaceutical actives can be used. Mixtures of the said insecticides can be used. Preferably the active is a liquid at 21° C., although less preferably the active can be a solid at 21° C. All these actives are suitable to be carried in the micro-particles of the composition of the composition of the subject invention. Every listed active is herein expressly disclosed in combination with every listed dispersion matrix. Sometimes (for example in order to produce a fragrance having desired fragrance high notes and desired fragrance low notes) it is desired to carry a blend or mixture of actives dispersed in the dispersion matrix. Any such blend or mixture of actives can be dispersed in the micro-particle as would be well known to the skilled addressee and any desired combination of actives is herein expressly disclosed in combination with every listed dispersion matrix.

As described herein the dispersion liquid has the function of dispersing the micro-particles of the composition of the invention and a composition comprising a plurality of these micro-particles and a dispersion liquid in which said micro-particles are dispersed is a product of the invention and an example is shown in FIG. 30. The dispersion liquid also prevents the caking of the micro-particles of the composition of the invention on the components of the high energy micro-particle producing machine. Micro-particle production can take place using a dispersion liquid, with or without a surface tension lowering agent. Dispersion liquids that can be used without a surface tension lowering agent are selected from propylene glycol, glycerol, paraffin oil, methyl silicone fluids, a blend of surfactants suitable for use as a laundry detergent base, and a blend of surfactants suitable for use as a fabric conditioner and mixtures thereof. Use of a dispersion liquid comprising a surface tension lowering agent (preferably water plus surface tension lowering agent) is preferred when it is desired to produce micro-particles with sizes up to about 10 micrometers. Every listed dispersion liquid or combination thereof is hereby expressly disclosed in combination with every herein disclosed dispersion matrix, every herein disclosed active, every herein disclosed wax or wax like material and every herein disclosed high energy micro-particle producing machine.

As described above micro-particle production can take place using a dispersion liquid which comprises a surface tension lowering agent. When it is desired the micro-particles of the composition of the invention have a particle sizes of 10 micrometers or less down to a minimum particle size of 0.1 micrometer use of a dispersion liquid comprising a surface tension lowering agent (e.g. Tween 80® dispersing) is preferred. Without wishing to be bound by theory it is believed a function of the surface tension lowering agent (e.g. Tween 80) is to prevent flocculation of the produced micro-particles such that particle sizes of from 0.1-10 micrometers preferably 1-10 micrometers can more easily be obtained.

Preferably at least a majority of said micro-particles, more preferably at least 80% of said micro-particles, yet more preferably at least 90% of said micro-particles, even more preferably substantially 100% of said micro-particles have a particle size of from 0.1 to 20 micrometers. More preferably at least a majority of said micro-particles, even more preferably at least 80% of said micro-particles, yet more preferably at least 90% of said micro-particles, even more preferably substantially 100% of said micro-particles have a particle size of from 0.1 to 10 micrometers. Yet more preferably at least 90% of said micro-particles have a particle size of from 0.1 to 20 micrometers. Yet more preferably at least 90% of said micro-particles have a particle size of from 0.1 to 10 micrometers. Even more preferably at least 90% of said micro-particles have a particle size of from 1 to 10 micrometers. Preferably the average particle size is from 3-7 micrometers, more preferably from 4-6 micrometers yet more preferably from 4.5-5.5 micrometers. In more preferred embodiments the above particle sizes of the micro-particles are achieved when micro-particle production takes place using a dispersion liquid which comprises a surface tension lowering agent. Preferably the combination of the dispersion liquid and surface tension lowering agent comprises a blend of an aqueous phase and the surface tension lowering agent capable of lowering the surface tension of the aqueous phase to 30 dynes/cm or less, more preferably capable of lowering the surface tension of the aqueous phase to 20 dynes/cm or less, even more preferably capable of lowering the surface tension of the aqueous phase to 10 dynes/cm or less. Preferably the combination of the dispersion liquid and the surface tension lowering agent comprises a blend of water and the surface tension lowering agent. Preferably said surface tension lowering agent is present in the dispersion liquid in an amount of 0.5-10 weight percent, more preferably in an amount of 2-6 weight percent.

Blends of liquid surfactants can be considered as dispersion liquid/surface tension lowering agent combinations. In this situation a liquid surfactant component of the blend disperses a further liquid surfactant component of the blend. Examples of blends of liquid surfactants are laundry liquid detergent concentrates and fabric conditioners. Every listed dispersion liquid/surface tension lowering agent combination, or combination thereof is hereby expressly disclosed in combination with every herein disclosed dispersion matrix, with every herein disclosed active, and every herein disclosed high energy micro-particle producing machine. When micro-particle production takes place using a dispersion liquid (e.g. water) which comprises a surface tension lowering agent, a dispersion liquid/surface tension lowering agent combination that can be used is water as the dispersion liquid the water including Tween 80® dispersing agent as the surface tension lowering agent. Tween 80® dispersing agent is commercially available from Akzo Nobel N.V. and is a non-ionic surfactant derived from polyethoxylated sorbitan and oleic acid. Tween 80 is often used in foods. Where particle sizes of 10 micrometers or less are desired, use of a dispersion liquid comprising a surface tension lowering agent (e.g. water comprising Tween 80® dispersing agent) is preferred.

High energy micro-particle producing machines having a micro-particle producing assembly as described herein are well known in the art and are commercially available. Preferably said high energy micro-particle producing machine having said micro-particle producing assembly is a high energy rotor-stator machine comprising a rotor-stator assembly. High energy micro-particle producing machines are high energy machines relative to low energy machines such as ordinary low energy impeller type mixers which low energy impeller type mixers habitually use ordinary paddle like mixing means of the type shown in FIG. 31. Mixing with machines having these ordinary paddle like mixing means is not characterized by the production of micro-particles but involves mere mixing. In contrast processing a combination of wax or wax like material, active and dispersing liquid (with or without surface tension lowering agent) with high energy micro-particle producing machines such as the FrymaKoruma Toothed colloid mill results in the production of a composition comprising a plurality of micro-particles dispersed in the dispersion liquid.

FIG. 30 shows a photograph of the product composition of Example 2 (subject invention) comprising a plurality the micro-particles of the composition of the invention dispersed in their dispersion liquid including surface tension lowering agent. As can be seen this product composition has the appearance of smooth creamy material. In order to demonstrate that there must be processing in a high energy micro-particle producing machine, the process of Example 2 as set out below was repeated except that there was mixing with an ordinary low energy impeller type mixer of the type described above rather than in the high energy FrymaKoruma Toothed Colloid Mill used in Example 2. At the end of the cooling stage of Example 2 clumps had been formed which persisted even after 30 minutes additional mixing with the ordinary low energy impeller type mixer. A picture of these clumps as they looked after the 30 minutes mixing is shown in FIG. 32. This can be used to determine whether a machine is a high energy micro-particle producing machine required to be used to produce the micro-particles of the composition of subject invention or whether it is not such a machine. If Example 2 herein is carried out and a clumped mass as shown in FIG. 32 is produced after the processing with the machine, the machine is not a high energy micro-particle producing machine. If on the other hand Example 2 is carried out and a smooth creamy material as shown in FIG. 30 is produced after processing in the machine, the machine is a high energy micro-particle producing machine.

Colloid mills are a species of high energy micro-particle producing machines as are other species of high energy micro-particle producing machines such as the Ultra-Turrax® emulsifying mixer Type T25 basic available from IKA Werke GmbH & Co KG, Germany as used in Example 4 herein and the Silverson® mixer. Silverson mixers are available from Silverson Machines Ltd, Waterside, Chesham, Bucks HP5 1 PQ, U.K Any type of colloid mill can be used in the process of the subject invention and examples of suitable colloid mills are listed below. Colloid mills made by Sonic Corporation are preferred. In the process of the subject invention more spherical micro-particles are produced as compared to the more rod shaped micro-particles that are produced by the cold process used for example in U.S. Pat. No. 4,152,272. High energy micro-particle producing machines which can be used in the process of the subject invention include high energy fluid shear mixers or colloid mills. General disclosure on high energy micro-particle producing machines and more details of high energy micro-particle producing machines which are preferred for use in the subject invention will be set out below.

When the inventive composition exits the high energy micro-particle producing machine for the last time the said inventive composition comprises the plurality (e.g. billions) of the micro-particles and the dispersion liquid (with or without surface tension lowering agent) in which said micro-particles are dispersed. These plurality of micro-particles dispersed in the dispersion liquid (with or without surface tension lowering agent) are a product of the inventive method described herein and in a further step can be collected and packaged for sale.

Figure 1:
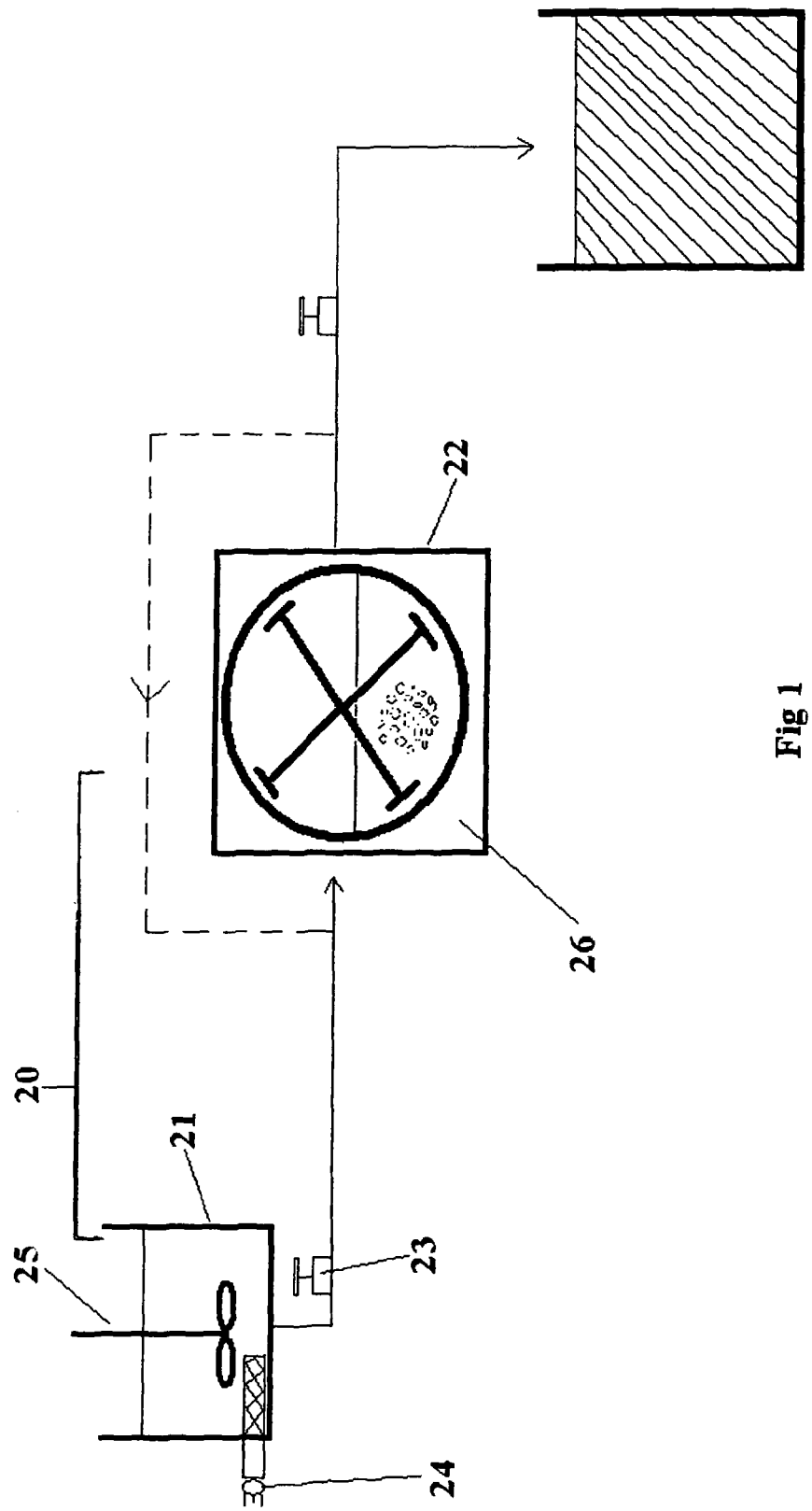
FIG. 1 shows a schematic drawing of a first embodiment of a process in accordance with the subject invention.

FIG. 1 shows a schematic drawing of a first embodiment of the process in accordance with the subject invention. The high energy micro-particle producing machine 20 (hereinafter referred to as the mill) used was a 2.5 inch Sonic bench top colloid mill comprising feeding funnel 21 and micro-particle producing assembly 22 supplied by Sonic Corporation whose address is set out below. The mill comes fitted with a laboratory mixer 25 for use in its feeding funnel 21. The mill was further adapted as follows. A stopcock 23 was fitted below the feeding funnel between feeding funnel and micro-particle producing assembly 22 such that the stopcock could be either closed to close off the flow of fluid from the feeding funnel into the micro-particle producing assembly 22 or the stopcock could be opened to allow the flow of fluid from the feeding funnel into the micro-particle producing assembly 22. Furthermore the feeding funnel was equipped with an immersion heater 24, the heating part of which could be introduced into the fluid contained within the feeding funnel when the stopcock was in the closed position to heat the fluid contained in the feeding funnel to a desired temperature. The mill was equipped with a water cooling jacket 26. The stopcock below the feeding funnel 21 was closed to close off the flow of fluid from the feeding funnel into the micro-particle producing assembly 22. Then individual amounts of dispersion liquid, surface tension lowering agent, active and wax or wax-like material were added to feeding funnel 21 and the combination was heated by the immersion heater 24 to 75° C. whilst stirring with the laboratory mixture 25. The individual compounds were added in such amounts as to give the desired concentration of active dispersed in the wax or wax-like dispersion matrix of each micro-particle of the product composition and to give the desired concentration of the produced micro-particles in their dispersion liquid. All feeding pipes of the micro-particle producing assembly 22 were preheated with heating tape to approximately 80-90° C. The mill's water cooling was turned on. The micro-particle producing assembly was switched on and the feed to the micro-particle producing assembly was started by opening the stopcock between funnel and micro-particle producing assembly inlet to allow the heated mixture contained in the feeding funnel to pass through the micro-particle producing assembly within 30 seconds. The milled composition comprising a plurality of micro-particles and the dispersion liquid (with or without surface tension lowering agent) in which said micro-particles are dispersed was taken out of the mill and collected. The temperature of the cold water flowing through the water cooled jacket 26 had previously been adjusted such that the composition exiting the mill had a temperature below the solidification point of each produced micro-particle. With the Sonic mill it is possible to produce micro-particles having concentration in a range up to 80 weight % active dispersed in the wax or wax-like dispersion matrix and it is also possible to produce the composition comprising a high concentration of up to 60 weight percent of micro-particles dispersed in their dispersion liquid. Optionally the combination can be re-circulated through the micro-particle producing assembly for additional cooling of the combination as shown by dotted lines in FIG. 1. Other cooling means can be used for cooling said melted combination of dispersion liquid (with or without surface tension lowering agent), active and wax or wax like material to a temperature below the solidification point of each produced micro-particle for example feeding additional cold dispersion liquid (with or without surface tension lowering agent) into the said melted combination in the micro-particle producing assembly. The composition comprising the plurality of micro-particles dispersed in their dispersion liquid (with or without surface tension lowering agent) can be further cooled after exiting the mill for example either by use of a water cooled heat exchanger or through use of additional dilution liquid. Further cooling allows the product to be more easily filled into its container (in which it is shipped to customers). In addition said further cooling by use of the additional dilution liquid enables the product having a high concentration of the micro-particles in their dispersion liquid (with or without surface tension lowering agent) to be diluted easily according to the needs of the customer. In another embodiment the active and the wax or wax like material can be provided as a composition comprising the wax or wax-like dispersion matrix with said active dispersed therein, and the composition can be either provided in solid or melted form. For example Bell MikroChips® could be added to the feeding funnel 21 either in solid or melted form.

Figure 2:
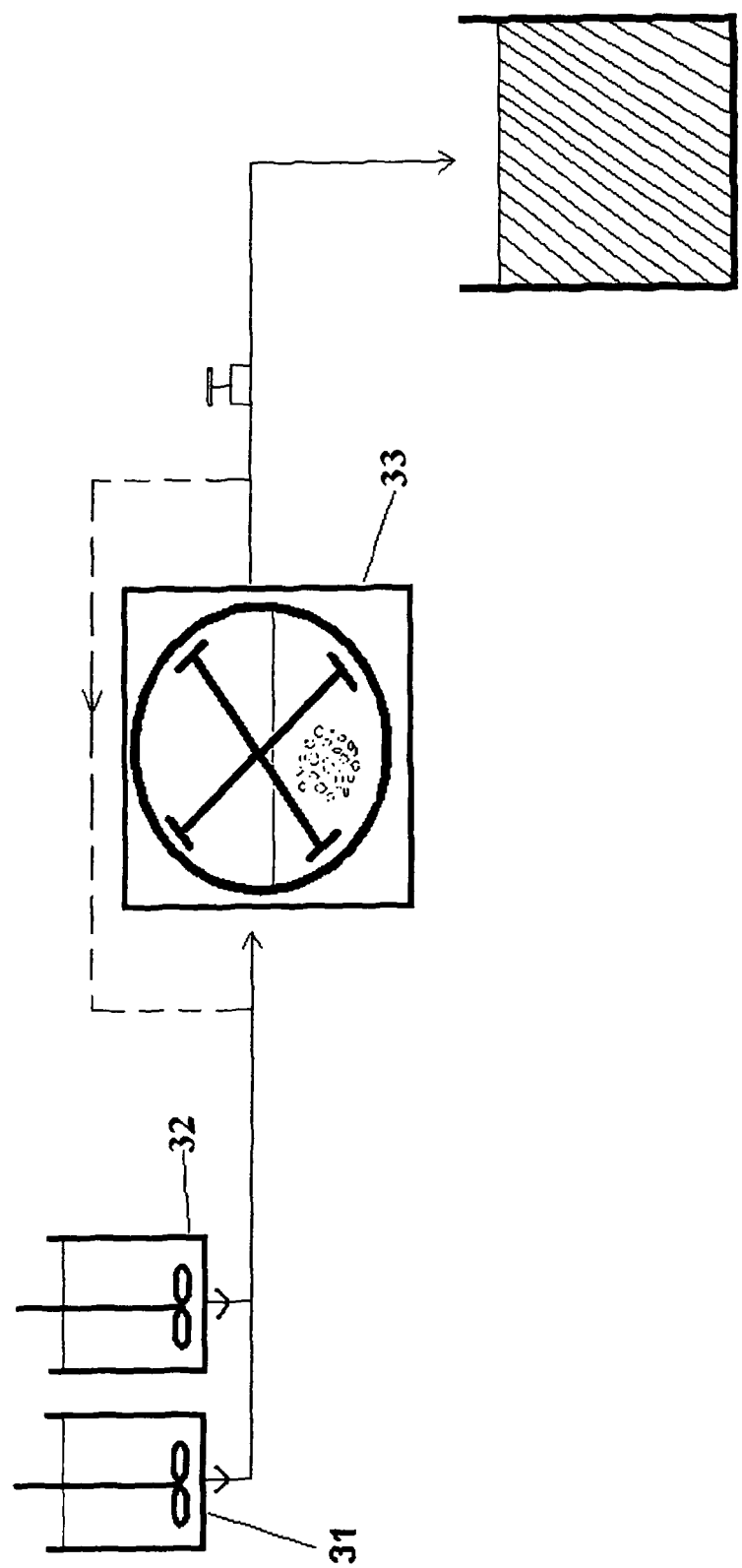
FIG. 2 shows a schematic drawing of a second embodiment of a process in accordance with the subject invention.

FIG. 2 shows a schematic drawing of a second embodiment of the process in accordance with the subject invention. In this embodiment the high energy micro-particle producing machine used was a FrymaKoruma Toothed Colloid Mill, Type MZ 80 available from FrymaKoruma AG, Switzerland, the FrymaKoruma Colloid Mill being provided with a water cooling jacket. A mixture of dispersion liquid and surface tension lowering agent (Phase A), was heated in a first beaker 31 to 82° C. Then individual amounts of active and wax or wax-like material were added to a second beaker 32 and heated to 90° C. and mixed to homogenity (Phase B). The individual compounds and the compositions were added in such amounts as to give the desired concentration of active dispersed in the wax or wax-like dispersion matrix of each micro-particle of the product composition and to give the desired concentration of the produced micro-particles in their dispersion liquid. The heated phase A composition was filled into the Fryma colloid mill 33. The Fryma colloid mill 33 was switched on and the heated Phase A composition was allowed to re-circulate through the mill. Then in a time period of 1 minute all the Phase B composition (melted wax or wax-like dispersion matrix with an active dispersed therein) was continuously poured into the mill containing the re-circulating hot Phase A composition. Then the tap water cooling system of the Fryma colloid mill 33 was turned on during recirculation of the combination of the Phase A composition plus the Phase B composition to cool down the combination. After 4 min of running of the mill with its tap water cooling system in operation the composition comprising a plurality of micro-particles dispersed in said dispersion liquid was formed by dropping the temperature of the combination of Phase A plus Phase B in the mill to a temperature below the solidification point of each produced micro-particle. The product composition was taken out of the mill and the mill was switched off. With the Fryma mill it is possible to produce micro-particles having concentration in a range up to 60 weight % active dispersed in the wax or wax-like dispersion matrix and it is also possible to produce the composition comprising a high concentration of up to 60 weight percent of micro-particles dispersed in their dispersion liquid. The composition comprising the plurality of micro-particles dispersed in their dispersion liquid can be further cooled after exiting the mill for example either by use of a water cooled heat exchanger or by use of additional dilution liquid similar to the situation with the Sonic mill described above. In another embodiment the active and the wax or wax like material can be provided into beaker 32 as a composition comprising the wax or wax-like dispersion matrix with said active dispersed therein, and the composition can be either provided in solid or melted form. For example Bell MikroChips® could be added to the beaker either in solid or melted form.

Figure 3:
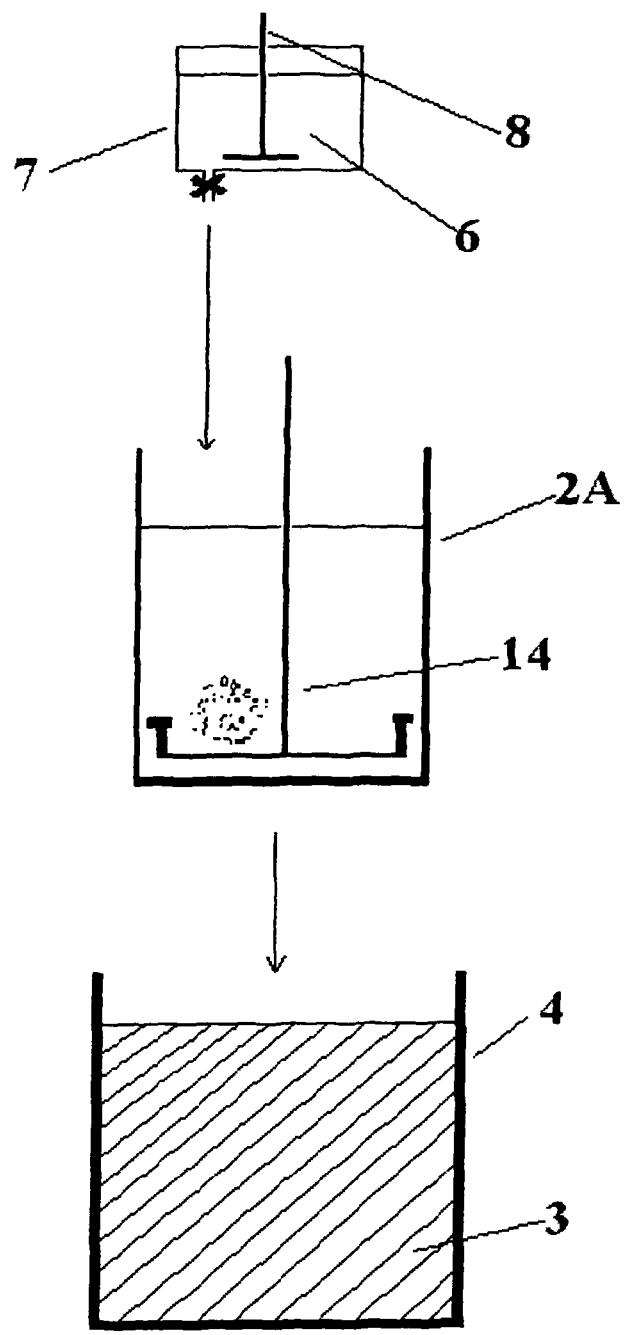
FIG. 3 shows a schematic drawing of a third embodiment of a process in accordance with the subject invention.

FIG. 3 shows a schematic drawing of a third embodiment of a process in accordance with the subject invention. The high energy micro-particle producing machine used was a Silverson high energy emulsifier mixer 14. Dispersion liquid (for example water comprising a Tween 80® dispersing agent) was added to beaker 2A which is equipped with the Silverson mixer. Individual amounts of active (e.g. perfume) and wax or wax-like material were added to a beaker 7 and then heated (with heating means which is not shown) to form a melted composition 6 comprising a wax or wax-like dispersion matrix with the active dispersed therein whilst stirring with laboratory mixer 8. Alternatively solid chips of a composition comprising a wax or wax-like dispersion matrix with an active dispersed therein for example Bell MikroChips® pastilles having particle size of about 3 mm could be added to a beaker 7 and heated to form a melted composition 6 whilst stirring with laboratory mixer 8. In each case the melted composition 6 was held at such a temperature to keep it melted and in the case where the MikroChips® pastilles are used the melted composition 6 was held in beaker 7 at a temperature of about 80° C. The dispersion liquid in beaker 2A was cooled to a temperature about 15 below the solidification temperature of melted composition 6 which in the case where the MikroChips® pastilles were used was about 50° C. The Silverson mixer was turned on and the melted composition 6 was added to beaker 2A whilst emulsification with the Silverson mixer continued for about 30 minutes. Whilst the Silverson mixer 2A is in operation the mixture temperature decreases such that the micro-particles of the composition of the invention are form by solidification such that a composition comprising a plurality (e.g. billions) of micro-particles dispersed in their dispersion liquid is produced. These plurality of product micro-particles dispersed in the dispersion liquid are a product of the inventive method and in a further step can be collected and packaged for sale. Then the composition comprising the plurality of micro-particles dispersed in their dispersion liquid is taken out of the beaker 2A and collected batchwise in container 4 where the product is shown with reference numeral 3. The product 3 having the micro-particles dispersed in the dispersion liquid has the appearance of white emulsion paint. FIG. 3 shows a batch process with batchwise collection in container 4.

Figure 4:
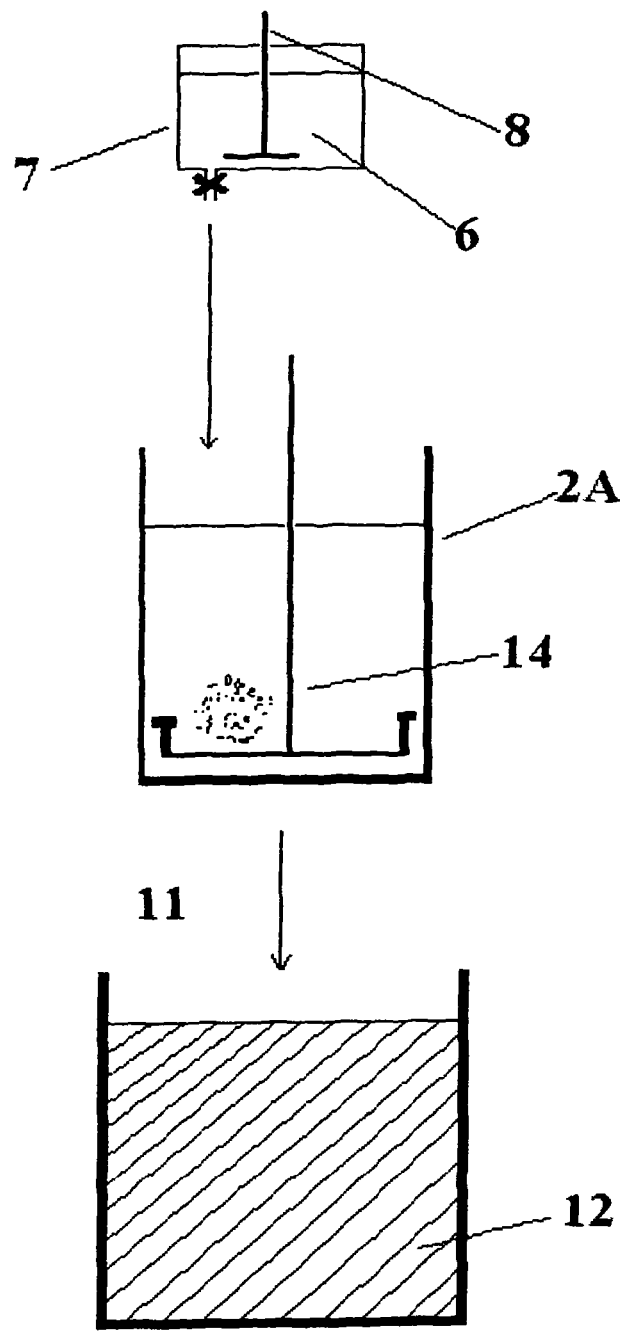
FIG. 4 shows a schematic drawing of a fourth embodiment of a process in accordance with the subject invention.

The process shown in FIG. 4 is a process similar to the process shown in FIG. 3 except that the process shown in FIG. 4 is a so called continuous process (not a batch process) utilizing in-line addition. A dispersion liquid such as propylene glycol without the inclusion of a surface tension lowering agent is used and has relatively lipophilic character and can be used in FIG. 4 or in any other continuous process embodiment. As a result of the use of propylene glycol as a dispersion liquid the propylene glycol being used without the inclusion of a surface tension lowering agent the micro-particles produced are relatively unstable and are not suitable for being stored for long but preferably should be used substantially immediately. The composition comprising the micro-particles produced by the process shown in FIG. 4 are shown being used for direct 'in line' addition as an ingredient into the apparatus of a second process whereby a product of the second process is produced which contains a plurality of the micro-particles of the composition of the present invention. For example the mentioned second process could be a process for making laundry liquid containing the composition comprising the micro-particles of the present invention. In FIG. 4 a continuous process is schematically shown where the composition comprising the micro-particles dispersed in the dispersion liquid are produced in a continuous process by automation of the process of FIG. 3 are then continuously removed from the beaker 2A as an intermediate product and then are continuously added into the line (in-line addition, see reference numeral (11)) of the second process (e.g. a process for making laundry liquid (12) containing the composition comprising the micro-particles of the subject invention).

Figure 5:
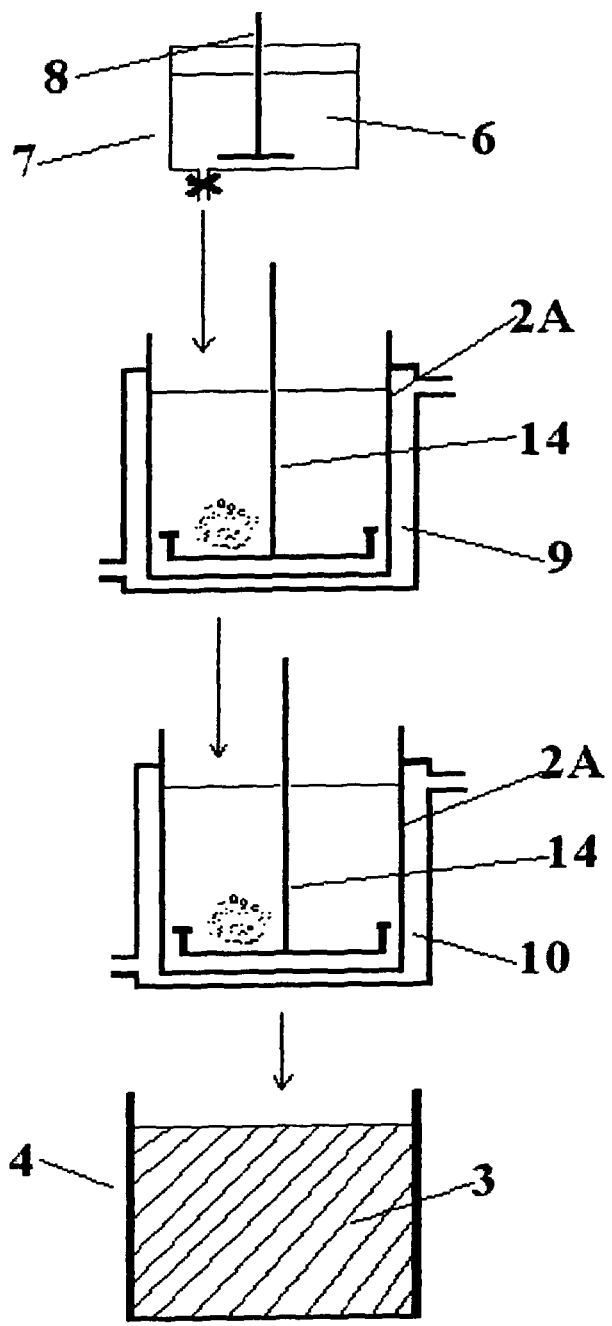
FIG. 5 shows a schematic drawing of a fifth embodiment of a process in accordance with the subject invention.

The process shown in FIG. 5 is a batch process similar to the process shown in FIG. 3 except that the dispersion liquid is hot i.e held at a temperature above the melting temperature of the melted composition 6. In the case of the use of the Bell MikroChips® pastilles this melting temperature is around 65. As for the process of FIG. 3 the processing in the Silverson mixer then takes place in two stages. There is a first higher temperature stage of processing where heating is applied during processing such that the first stage of processing taking place ot at a temperature above the melting temperature of the composition 6. There is then a change in the processing temperature during the operation of the machine with transitioning of processing temperature through the melting temperature of the composition 6. There is then a second lower temperature stage of processing with the Silverson mixer which takes place at a temperature below the melting temperature of the melted composition 6 where cooling is applied during processing with the Silverson mixer.

Most preferably during this 'hot' processing stage the temperature is held very close to, but just above the melting temperature of the micro-particles that are produced as a product of the process, to avoid temperature stress to the actives of the micro-particles as discussed above. Temperature stress to the actives of the micro-particles arises where the actives of the micro-particles are subjected to unnecessarily high temperatures. For example in a case where the active is a relatively volatile perfume subjecting the perfume to an unnecessarily high temperature can result in loss of the perfume where the perfume volatizes and is driven away. Furthermore it is a waste of energy to use unnecessary heating in the process particularly as any such unnecessary heating is then followed by cooling.

During the second lower temperature stage of processing the mixture undergoing the process is preferably held at a temperature just below the melting temperature of the micro-particles that are produced. For easier understanding of the two processing stages two representations of Silverson mixer 14 are shown, a first representation of Silverson mixer 14 being shown equipped with steam jacket 9 representative of a first processing stage and a second representation of Silverson mixer 14 being shown equipped with a water cooling jacket 10 representative of a second processing stage where micro-particle production is taking place. It is to be understood that a sole Silverson mixer 14 is used in the process shown in FIG. 5, but equipped with both steam jacket 9 and water cooling jacket 10 wherein the steam jacket 9 is used in the first processing stage. Then at the start of the stage of temperature transitioning use of the steam jacket is stopped and use of the water cooling jacket is started. Then use of the water cooling jacket 10 continues in the second processing stage. In the case of the use of Bell MikroChips steam jacket 9 is used to keep the mixture at a suitable temperature for example around 68° C. for good temperature control during the primary processing step and for good temperature control during the second processing stage cooling jacket 10 is used to keep the mixture at a suitable temperature for example around 58° C. Any suitable temperature reducing means can be used to reduce the temperature to a temperature below the melting temperature of the micro-particles that are produced as a product of the process. The temperature reducing may for example take place in the fluid shear micro-particle producing machine due to a cooling jacket being turned on, or through dilution of the media being processed with cold dispersion liquid while the high shear micro-particle producing machine is running.

The composition of the subject invention comprising the plurality of micro-particles and the dispersion liquid (with or without surface tension lowering agent) in which said micro-particles are dispersed can be used for direct 'in line' addition as an ingredient into the apparatus of a second process whereby a product of the second process is produced which contains a plurality of the micro-particles. This in line addition embodiment is explained with regard to FIG. 4 for example. This in line addition embodiment can be used as a preferred feature of any embodiment of the invention herein disclosed and is hereby disclosed generally in combination with any of the embodiments of the invention herein disclosed. There are however dispersion liquid or dispersion liquid surface tension lowering agent combinations which can only be used in the in-line processes because their use results in the production of micro-particles of the composition of the invention which are not sufficiently storage stable to be batchwise collected and stored. The particular dispersion liquid or dispersion liquid/surface tension lowering agent combination used will affect the stability of the micro-particles produced and preferably is selected based on its hydrophile lipophile character. Where as is usually the case the active has lipophilic character, micro-particles produced with dispersion liquid or dispersion liquid/surface tension lowering agent combinations having hydrophilic properties will be relatively storage stable, whereas micro-particles produced with dispersion liquid or dispersion liquid/surface tension lowering agent combinations having relatively lipophilic character will affect release of the contained active almost immediately. Whilst not wishing to be bound by theory it is believed that where the actives are lipophilic, the lipophilic actives tend to be dragged out of their dispersion within the micro-particles of the composition of the invention into solution in the dispersion liquid or dispersion liquid/surface tension lowering agent combination if the dispersion liquid or dispersion liquid/surface tension lowering agent combination is too lipophilic. As a result of the dragging out effect the micro-particles produced tend relatively quickly to be emptied out of active. Dispersion liquids selected from propylene glycol, glycerol, paraffin oil, methyl silicone fluids, and mixtures thereof used with a lipophilic active and used without a dispersing agent will produce micro-particles of the composition of the invention which are not storage stable.

The Fryma mill described with reference to FIG. 2 hereof is less preferred than the Sonic mill described with reference to FIG. 1 hereof because more numerous process steps are required with the Fryma than with the Sonic at least because with the Fryma the combination to be milled cannot be made in-situ in the machine. With the Fryma it is necessary separately to prepare the composition comprising the wax or wax-like dispersion matrix with an active dispersed therein externally to the machine. This is because the Fryma is not equipped with the type of stopcock controlled feeding funnel that the Sonic mill has and because it is not possible to use an immersion heater with the Fryma mill. Hence separate external preparation of starting material compositions is required with the Fryma. The process exemplified in Example 7 hereof is a very optimal process of the subject invention because a minimum number of process steps are used. Also use of the Sonic mill described with reference to FIG. 1 hereof results in the production of compositions of the subject invention comprising their micro-particles dispersed in their dispersion liquid (with or without surface tension lowering agent) having optimal micro-particle size of about 10 microns plus optimal narrow micro-particle size distribution. This results partly from the possibility of being able to adjust the size of the milling gap of the machine's micro-particle producing assembly and partly from the efficiency of the machine due to its relatively high energy.

Having discussed several process advantages of the process of the subject invention the processing advantages of the process of the subject invention over the cold process as described in U.S. Pat. No. 4,152,272 can be readily understood. Generally speaking the process of the subject invention requires less steps, uses less equipment in its process, is more economical, is more efficient, is cheaper and easier to implement in commercial operation, and produces a better product.

In the process as described in U.S. Pat. No. 4,152,272 use of a colloid mill is required and certain other high energy micro-particle producing machines described herein for example the Silverson L5 series of laboratory mixers or the Ultra-Turrax® emulsifying mixer Type T25 basic cannot be used to produce the composition comprising the micro-particles as claimed due to being insufficiently powerful. Furthermore the process as described in U.S. Pat. No. 4,152,272 requires feeding of solid material (the solid composition comprising a wax or wax-like dispersion matrix with an active dispersed therein, e.g. Bell MikroChips®) into the colloid mill and with certain colloid mills described herein (e.g. the 2.5 inch Sonic bench top colloid mill used in Example 7 hereof) it is impossible to feed solid material into the mill. Even finely divided solid material for example as produced after a pre-grind step in a 'coffee grinder' like mechanical grinding machine cannot be fed into the 2.5 inch Sonic bench top colloid mill used in Example 7 hereof. Hence in order to use the 2.5 inch Sonic bench top colloid mill used in Example 7 hereof in the cold process it is necessary to form a slurry (e.g of the Bell MikroChips) that is capable of fluid flow into the 2.5 inch Sonic bench top colloid mill. This requires more process steps and complexity.

Figure 14:
FIG. 14 shows a cut out part of a photomicrograph (magnification 400 fold) showing micro-particles of the composition of the invention produced by the method of Example 3 herein.
Figure 14A:
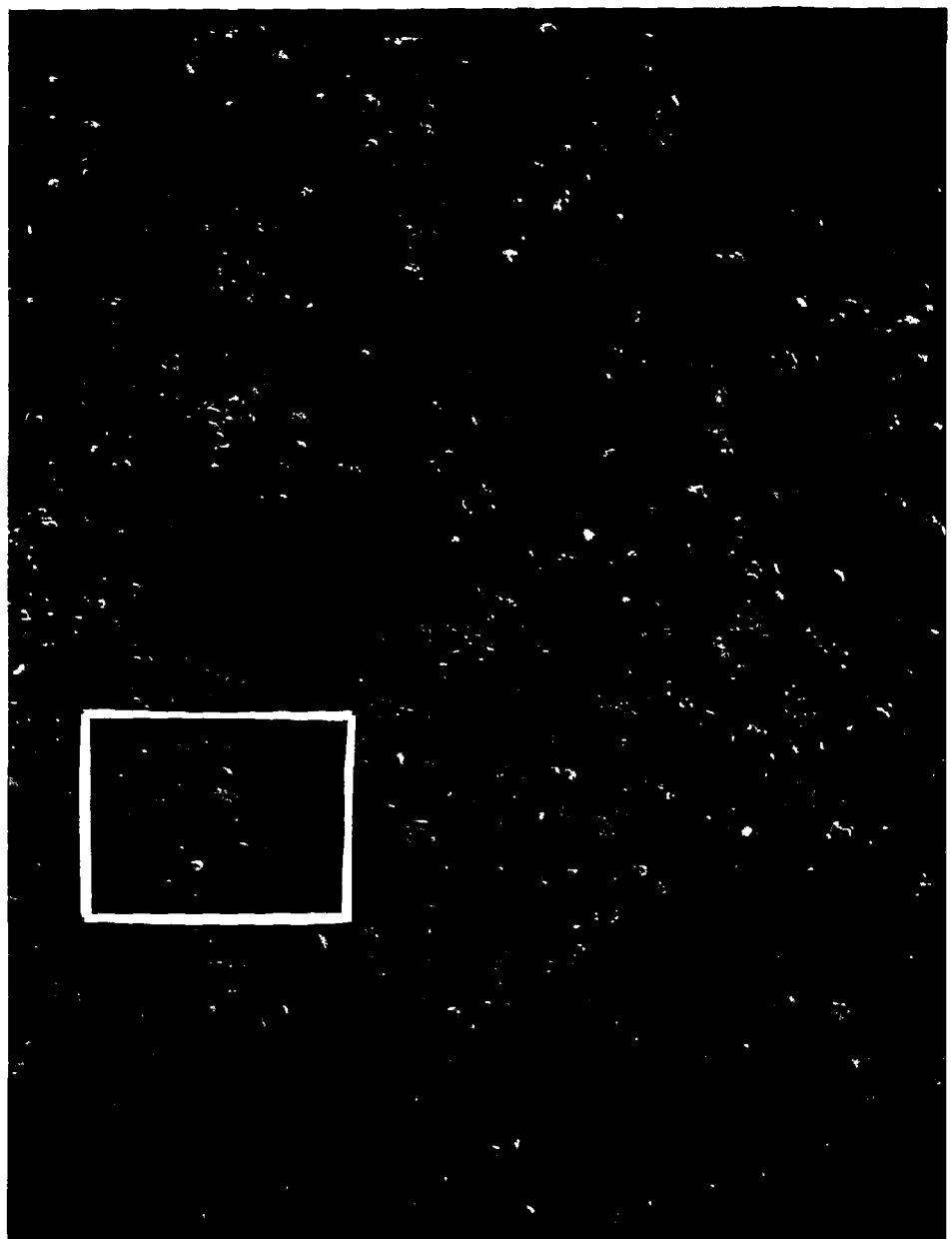
FIG. 14A shows the full photomicrograph of FIG. 14.

The process of the subject invention is also advantageous over the process as described in U.S. Pat. No. 4,152,272 when it is desired to obtain high concentrations of the micro-particles of the composition of the invention in the dispersion liquid in which they are dispersed. In the process U.S. Pat. No. 4,152,272 it is not possible to achieve such high concentrations of the micro-particles in the dispersion liquid in which they were dispersed as can be achieved in the process of the subject invention. U.S. Pat. No. 4,152,272 describes that the maximum amount of its size reduced micro-particles which can be present in the dispersion liquid in which they were size reduced in 20 weight percent. When the process of the subject invention is used to produce the micro-particles much higher concentrations of micro-particles in the dispersion liquid in which they are dispersed can be produced up to a maximum of 60 weight percent. With the process of the subject invention concentrations of the micro-particles of the composition of the subject invention in the dispersion liquid in which they are dispersed in a range of up to 60 weight percent, preferably from 21 weight percent to 60 weight percent can be achieved. A further advantage of the process of the subject invention over the process used in U.S. Pat. No. 4,152,272 is that with the process of the subject invention the micro-particles of the composition of the subject invention are more uniform in size than are the micro-particles of the composition of U.S. Pat. No. 4,152,272. The micro-particles shown in FIGS. 6A, 14A and 26A are produced by processes similar to the processes used in U.S. Pat. No. 4,152,272. The micro-particles shown in FIGS. 10A, 18A and FIGS. 33-34 are produced in accordance with the process of the subject invention. As can be seen the micro-particles shown in FIGS. 10A, 18A and FIGS. 33-34 form a more crowded 'universe' of micro-particles with less big size 'clumps' visible. Less big size 'clumps' is indicative of micro-particles being more uniform in size. More crowding of the micro-particles is indicative of the obtaining of higher concentrations of micro-particles per unit amount of the dispersion liquid in which the micro-particles are dispersed. Any specific amount (whether measured by reference to weight or volume) of the dispersion liquid in which the micro-particles are dispersed can be taken as a unit amount for the purpose of comparing relative concentrations of the micro-particles in the dispersion liquid in which the micro-particles are dispersed provided the specific amount chosen is the same for all comparisons. In preferred compositions of the subject invention comprising a plurality of micro-particles and a dispersion liquid (with or without surface tension lowering agent) in which said micro-particles are dispersed the active of each said micro-particle is a perfume or mixture thereof and the wax or wax-like dispersion matrix is a C22 fatty alcohol dispersion matrix. U.S. Pat. No. 4,152,272 describes perfumed conditioning compositions comprising micro-particles dispersed in an aqueous dispersion liquid. These compositions of U.S. Pat. No. 4,152,272 comprise from 0.1% to 20% micro-particles by weight of the composition. Each micro-particle of the composition of U.S. Pat. No. 4,152,272 comprises by weight of the microparticles, less than 95% and at least 25% of a dispersion matrix and from 1% to 75% of the perfume. The composition of the subject invention comprising a high concentration of micro-particles dispersed in their dispersion liquid is more efficient at imparting a high perfume loading to a fabric treating composition than is the composition of U.S. Pat. No. 4,152,272 because the composition of the subject invention can impart a higher perfume loading per unit amount of dispersion liquid than can the composition of U.S. Pat. No. 4,152,272. U.S. Pat. No. 4,152,272 accordingly discloses a maximum perfume loading per unit amount of 15% (75%× 20%). The micro-particles of the composition of the subject invention are present in their dispersion liquid at concentrations up to a maximum concentration of 60 weight percent and each said micro-particle can preferably comprise up to 80 weight percent perfume in the wax or wax like dispersion matrix, less preferably up to 60 weight percent perfume in the wax or wax like dispersion matrix. Therefore with the use of the micro-particles of the composition of the subject invention a maximum perfume loading per unit amount of 48% (80%×60%) can be achieved. Even when the micro-particles of the composition of the subject invention only comprise 60 weight percent perfume in the wax or wax like dispersion matrix a perfume loading per unit amount of 36% (60%×60%) can be achieved. This possibility of imparting a higher perfume loading per unit amount of dispersion liquid through use of the micro-particles of the composition of the subject invention has particular advantages when perfuming thick gelled laundry liquids comprising e.g. a 90% gelled solution of surfactants when only about a third to half the amount of dispersion liquid need be used as compared to the amount of dispersion liquid needed by the composition of U.S. Pat. No. 4,152,272 to achieve the same amount of perfume inputted thereby making it easier to provide desirable high perfume loadings to these thick gelled laundry liquids without breaking the gel. When trying to maximize the amount of perfume in the wax or wax like dispersion matrix of each micro-particle of the composition of the subject invention during the inventive process it is desirable to hold the temperature of the melted wax or wax-like dispersion matrix with the active dispersed therein very close to, but just above the melting temperature of the micro-particles that are produced as a product of the process to avoid loss of the normally volatile perfume by evaporating it away and preferred temperature ranges to achieve this are mentioned above.

The process of the subject invention is also advantageous over the process as described in U.S. Pat. No. 4,152,272 when it is desired to obtain lower average size and smaller size distribution of the micro-particles of the composition of the invention in the dispersion liquid in which they are dispersed. In the compositions comprising the plurality of micro-particles dispersed in their dispersion liquid as produced by U.S. Pat. No. 4,152,272 the average size of the micro-particles is about 50 microns with relatively large size distribution whereas with the process of the subject invention it is possible to achieve an average size of the micro-particles of the composition of the invention of is about 10 microns (or any other size desired) with relatively small size distribution.

A further advantage of the composition of the subject invention comprising high concentrations of micro-particles dispersed in their dispersion liquid is that it is easy to sell product compositions comprising the plurality of micro-particles dispersed in their dispersion liquid at concentrations of the micro-particles in the dispersion liquid desired by the end user. It is easy and cheap from a processing point of view to produce a range of compositions of the subject invention having concentrations of micro-particles dispersed in their dispersion liquid tailored to the individual desires of individual customers by dilution of the compositions of the subject invention with more dispersion liquid (e.g. suitable amounts and concentrations of water plus Tween).

In batch process embodiments the composition of the invention comprising a plurality of micro-particles dispersed in their dispersion liquid is collected batchwise in a container. This batch embodiment can be used as an alternative to the in-line addition embodiment as a preferred feature of any embodiment of the invention herein disclosed and is hereby disclosed generally in combination with any of the embodiments of the invention herein disclosed. The batchwise product is a product preferably a final product of the process of the invention.

The method used herein for measuring the particle size of the micro-particles of the invention as measured by Quantachrome GmbH & Co. KG, Rudolf-Diesel-Strasse 12, D-85235 Odelzhausen is described in Example I hereof.

The Actives

Many different actives can be carried by the dispersion matrices described herein. Perfumes, or mixtures thereof, are a highly desirable active that can usually benefit from protection and that can be carried, especially when the perfume, or mixture thereof, is relatively hydrophobic. Flavoring actives, or mixtures thereof are like perfumes in that they tend to be adversely affected by the environment and require protection and are another active can be carried by the dispersion matrices described herein. Another type of active that is often in need of protection in carrier matrices etc. is a pharmaceutical active, or mixtures thereof, that also needs to be protected from the environment and can be carried by the dispersion matrices described herein. Yet another type of active that is often in need of protection and can be carried by the dispersion matrices described herein is a natural material active e.g. a botanical extract or mixtures thereof. Yet another type of active that is often in need of protection and can be carried by the dispersion matrices described herein is an essential oil or mixture thereof. Yet another type of active that is often in need of protection and can be carried by the dispersion matrices described herein is an insecticide, or mixture thereof.

Yet another type of active that can be carried by the dispersion matrices described herein e.g. for protection from the environment is an oxidation or reduction active or mixture thereof that interacts with other materials that are present. In general, actives that are carried by the dispersion matrices of the subject invention e.g. those formed of a C22 fatty alcohol or other dispersion matrices herein described and are released by the action of heat are useful in the practice of this invention and these will be described herein below.

Perfumes:

Detergents; fabric softening products; cosmetics, including antiperspirants, hair and skin care products; and disposable absorbent products like diapers, all typically contain some perfume to provide some fragrance to provide an olfactory aesthetic benefit and/or to serve as a signal that the product is effective.

The perfume in such products is often lost before it is needed. Perfumes can be subject to damage and/or loss by the action of, e.g., oxygen, light, heat, etc.

Perfumes used in cosmetics and disposable absorbent products also tend to be lost prematurely. It is highly desirable to have volatile perfume ingredients or mixtures thereof dispersed in the dispersion matrices of the micro-particles of the composition of the invention until they are released by the heat of the human body etc.

The perfume actives of this invention are the conventional ones known in the art. Selection of any perfume component, or amount of perfume, is based solely on aesthetic considerations. Suitable perfume compounds and compositions can be found in the art including U.S. Pat. No. 4,145,184, Brain and Cummins, issued Mar. 20, 1979; U.S. Pat. No. 4,209,417, Whyte, issued Jun. 24, 1980; U.S. Pat. No. 4,515,705, Moeddel, issued May 7, 1985; and U.S. Pat. No. 4,152,272, Young, issued May 1, 1979, all of said patents being incorporated herein by reference. Many of the art recognized perfume compositions are relatively substantive, as described hereinafter, to maximize their odor effect on substrates. However, it is a special advantage of perfume delivery via the micro-particles of the composition of the subject invention that nonsubstantive perfumes are also effective.

A substantive perfume is one that contains a sufficient percentage of substantive perfume materials so that when the perfume is used at normal levels in products, it deposits a desired odor on the treated substrate. In general, the degree of substantivity of a perfume is roughly proportional to the percentage of substantive perfume material used. Relatively substantive perfumes contain at least about 1%, preferably at least about 10%, substantive perfume materials.

Substantive perfume materials are those odorous compounds that deposit on substrates via the treatment process and are detectable by people with normal olfactory acuity. Such materials typically have vapor pressures lower than that of the average perfume material. Also, they typically have molecular weights of about 200 or above, and are detectable at levels below those of the average perfume material.

Perfumes can also be classified according to their volatility, as mentioned hereinbefore. The highly volatile, low boiling, perfume ingredients typically have boiling points of about 250° C. or lower. Many of the more moderately volatile perfume ingredients are also quickly lost. For example, substantially all of such perfumes are lost in the drying cycle of a typical laundry process. The moderately volatile perfume ingredients are those having boiling points of from about 250° C. to about 300° C. The less volatile, high boiling, perfume ingredients are those having boiling points of about 300° C. or higher. Many of the perfume and flavor ingredients as discussed hereinafter, along with their odor and/or flavor characters, and their physical and chemical properties, such as boiling point and molecular weight, are given in "Perfume and Flavor Chemicals (Aroma Chemicals)," Steffen Arctander, published by the author, 1969, incorporated herein by reference.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, isoeugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other C15H24 sesquiterpenes.

Examples of the less volatile, high boiling, perfume ingredients are: benzophenone, benzyl salicylate, ethylene brassylate, galaxolide (1,3,4,6,7,8-hexahydro-4,6,6,7,8,8-hexamethyl-cyclo-penta-gama-2-benzopyran), hexyl cinnamic aldehyde, lyral (4-(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, and phenylethyl phenyl acetate.

Flavors

Flavoring materials or mixtures thereof are desirable actives to use dispersed in the dispersion matrices of the micro-particles of the composition of the invention. As used herein, the term "flavors" also includes spices, flavor enhancers, essential oils, natural extracts, etc., that contribute to the overall flavor perception.

Flavor actives, like perfume actives, normally consist of several components. Specific examples of flavors and flavor enhancers include those disclosed in U.S. Pat. No. 4,348,416, Boden, incorporated herein by reference. I.e., organic acids, e.g., acetic acid, formic acid, 2-hexenoic acid, n-butyric acid, caproic acid, caprylic acid, cinnamic acid, isobutyric acid, isovaleric acid, alphamethylbutyric acid, propionic acid, valeric acid, 2-methyl-2-pentenoic acid and, ketones and aldehydes, acetophenone, acetone, acetyl methyl carbinol, acrolein, n-butanal, diacetyl, 2-methylbutanal, methyl n-amyl ketone, n-hexanal, 2-hexanal, isopentenal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetophenone, 2-methyl-2-hepten-6-one, 2-octanone, 2-undecanone, furfural, 5-methyl-furfural, cinnamaldehyde, 2-pentanone, 2-pentenal and propanal, alcohols such as 1-butanol, benzyl alcohol, iso-borneol, trans-2-buten-1-ol, ethanol, geraniol, 1-hexanol, 2-heptanol, trans-2-hexen-1-ol, cis-3-hexen-1-ol, 1-penten-3-ol, isoamyl alcohol, phenyl-2-ethanol, alpha-terpineol, eugenol, linalool, 2-heptanol, menthol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, ethyl succinate, isobutyl cinnamate, cinnamyl formate, methyl cinnamate, and terpenyl acetate; hydrocarbons such as dodecane, methyl naphthalene, myrcene, caryophyllene, alphaphellandrene, beta-phellandrene, p-cymene, alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, methyl ethylpyrazine, tetramethylpyrazine, trimethylpyrazine; essential oils and extracts such as jasmine absolute, *cassia* oil, cinnamon bark oil, black pepper oleoresin, tumeric oil, oil of black pepper, rose absolute, orris absolute, oil of cubeb, oil of coriander, oil of pimento leaf, oil of patchouli, oil of nutmeg, ginger oil, lemon essential oil, dill oil, lemon grass oil, oil of valerion, marjoram oil, raspberry oil, cinnamon oil, carrot oil, anise oil, orange oil, thyme oil, peppermint oil, sweet cumin oil, celery oil, garlic oil, onion oil, tarragon oil, caraway oil, basil oil, bay leaf oil, mustard oil, sage, tea extract, coffee extract, safran oil, Bulgarian rose, capsicum, yara yara, vanilla, nut oils and the synthetic versions of these natural oils and extracts; lactones such as .gamma.-nonalactone; sulfides, e.g., methyl sulfide and other materials such as maltol, and acetals (e.g., 1,1-diethoxyethane, 1,1-dimethyloxyethane and dimethoxymethane), piperine, chavicine, and piperidine.

Specific examples of the invention include the use of the micro-particles of the composition of the invention in the preparation of powdered mixes, e.g., drink mixes. For example the micro-particles of the invention including, tea extract, synthetic sweeteners, and/or one or more flavors such as bergamot, jasmine, lemon oil, peppermint oil, etc., or mixtures thereof dispersed in the dispersion matrix of the micro-particle can be added to a powdered instant tea mix and the resulting product has a more stable flavor profile and the flavor is released immediately to allow for full enjoyment of the flavor. Examples of tea mixtures and instant tea mixes can be found in U.S. Pat. No. 4,474,822, Sato et al., issued Oct. 2, 1984; and in Brit. Pat. 2,074,838, to Chinoin Gyogyszer, issued Nov. 11, 1981, said patents being incorporated herein by reference.

Similar advantages are found when a flavor ingredient such as a beef extract is dispersed in the dispersion matrix of the micro-particle of the composition of the invention and added to a powdered soup mix.

Dairy products or mixtures thereof are especially desirable to be dispersed in the dispersion matrix of the micro-particle of the composition of the invention. Butter flavor is especially prone to destruction during storage.

The micro-particles of the composition of the invention carrying flavors are also very useful in other products like chewing gum, toothpastes and powders, medicines, etc., where the product is used in the mouth.

Pharmaceuticals:

Another class of actives that is highly desirable to carry/protect in the micro-particles of the composition of the invention is pharmaceutical materials (drugs) or mixtures thereof. Drugs that have been suggested for carrying include those described in the patents incorporated by reference hereinbefore, and especially U.S. Pat. No. 4,727,064, Pitha, issued Feb. 23, 1988, incorporated herein by reference. The list includes ibuprofen, acetylsalicylic acid (or its salts), acetamidophen, apomorphine, butylated hydroxytoluene, chlorthalidone, cholecalciferol, dexamethasone, dicumarol, digoxin, diphenylhydantoin, estradiol, estriol, ethinylestradiol-3-methyl ether, ethisterone, furosemide, hydroflumethiazide, indomethacin, iproniazid phosphate, 17-methyltestosterone, nitroglycerin, norethindrone, oubain, oxprenolol, progesterone, retinal, trans-retinoic acid and/or its salts, retinol, spironolactone, sulpiride, testosterone, theophylline, aryclovir, cloridine HCl, etc.

Botanical Extracts:

Another class of actives that is highly desirable to carry/protect in the micro-particles of the composition of the invention is botanical extracts or mixtures thereof. Botanical extracts are selected from *Dipteryx odorata* extract, Fennel oil, *Eugenia caryophyllata* oil, *Hierochloe odorata* extract, *Arnica montana* extract, *Rosa gallica* extract, *Passiflora incarnata* extract, *Junglans regia* shell extract, Chamomile oil, Apocarotenal, *Pyrus malus* juice, *Vitis vinifera* juice, *Arcticum Majus* Root Extract, *Mentha piperita, Nelumbo Nucifera* Flower Extract, *Purnus armeniaca* kernel oil, *Arctium lappa* root extract, Wachholderdestillat, *Melaleuca alternifolia* Extract, *Cupressus Sempervirens* Leaf Extract, *Hibiscus Sabdariffa* Extract, *Acacia farnesiana* extract, *Persea gratissima* extract, *Eucalyptus globulus* extract, *Mentha piperita* extract, *Santalum album* wood extract, *Cananga odorata* flower extract, *Ocimum Basilicum* extract, *Pimenta dioica* extract, *Arabica* Seed extract, *Coffea Arabica* Seed extract, *Avena Sativa* Kernel extract, *Prunus Amygdalus Amara* Extract, *Bambusa vulgarise* Stem Extract, *Capsicum Frutescens* extract, *Cinnamomum Zeylanicum* Extract, *Carica Papaya* Fruit Extract, *Solanum Lycopersicum* extract, *Cucurbita Pepo* extract, *Fortunella margarita* Extract, *Rubus fruticosus* extract, *Sapindus mukurossi* peel extract, *Avena Sativa* Extract, *Prunus Amygdalus Dulcis* Extract, *Aspalathus linearis* Extract, *Dipteryx odorata* bean extract, *Ocimum tenuiflorum* extract, *Plantago major* Extract, *Coffea Arabica* Bean Extract, *Cannabis Sativa* Seed Extract, *Aniba rosaeodora* extract, *Myrtus communis* extract, *Bambusa vulgaris* Extract, *Ficus carica* fruit extract, *Gossiypium Herbaceum* Seed Extract, *Mentha piperita* leaf extrac, *Vitis Vinifera* Seed Extract, *Hylocereus undatus* Extract, *Pinus Pumilio* Leaf Extract, *Bellis perennis* flower extract, *Avena sativa* bran extract, *Salvia Hispanica* Seed Oil, *Amaranthus Caudatus* Seed Extract, *Persea gratissima* fruit extract, *Thuja occidentalis* leaf extract, *Magnolia bondii* flower extract, *Purnus serotina* bark extract, *Fragaria vesca* fruit Extract, *Prunella Vulgaris* Extract, *Ananas Sativus* Fruit Extract, *Schinus terebinthifolius* seed extract, *Mentha aquatica* extract, *Tropaeolum majus* extract, *Piscum Ovum* Extract, *Viola tricolor* extract, *Serenoa Serrulata* Fruit Extract, *Citrus aurantium dulcis* fruit extract, *Pyrus malus* fruit extract, *Psidium guajava* fruit extract, *Centaurea cyanus* flower extract, *Salvia officinalis* leaf extract, *Ribes nigrum* fruit extract, *Juniperus Virginiana* Wood Extract, *Punica granatum* fruit extract, *Schisandrae Chinensis* Fruit Extract, *Chamaecyparis Obtusa* Leaf Extract, *Cornus officinalis* fruit extract, *Ribes nigrum* Extract, *Lavandula angustifolia* flower extract, *Citrus aurantifolia* fruit extract, *Arctium Lappa* Root Extract, *Foeniculum vulgare* fruit extract, *Eucalyptus globulus* leaf extract, *Camomilla Recutita* Flower Extract, *Urtica dioica* leaf extract, *Pumus armeniaca* fruit extract, *Laminaria japonica* extract, *Capsicum annuum* Extract, *Prunus Amygdalus* Amara Extract, *Purunus avium* fruit extract, *Linum usitatissimum* seed extract, *Vanilla planifolia* extract, *Glycyrrhiza glabra* extract, *Carum carvi* extract, *Panicum Miliaceum* Extract, *Anthemis nobilis* extract, *Calendula Officinalis* Extract, *Hypericium perforatum* extract, *Prunus persica* extract, *Cocos nucifera* extract, *Salvia officinalis* extract, *Ginkgo biloba* extract, *Centella asiatica* leaf extract, *Fucus vesiculosus* extract, *Saponaria officinalis* extract, *Rosmarinus officinalis* extract, *Tilia cordata* oil, *Tilia cordata* extract, *Aesculus hippocastanum* extract, *Equisetum arvense* extract, *Panax ginseng* root extract, *Citrus madurensis* extraxt, *Cucumis melo* extract, *Medicago sativa* extract, *Lawsonia inermis* extract, *Vitis vinifera* fruit extract, *Picea Excelsa* Leaf Extract, *Dioscorea Villosa* Extract, *Juglans regia* extract, *Euphrasia officinalis* extract, *Hamamelis virginiana* leaf extract, *Musa Sapientium* extract, *Urtica dioica* Extract, *Mentha piperita* leaf extract, *Lavender* oil, bulg., *Aloe barbadensis* extract, *Chamomilla recutica* flower extract, *Oryza Sativa* Bran Extract, *Brassica oleiferanapus* Extract, *Chamomile Thyme* Extr., *Acorus Calamus* Extract, *Chamaemelum nobile* extract, *Plantago lanceolata* extract, *Hedera helix* extract, *Chamomilla recutica* extract, *Hamamelis virginiana* extract, *Alchemilla vulgaris* extract, *Betula alba* leaf extract, *Betula alba* extract, Hydrolyzed silk, *Symphytum officinale* extract, *Sambucus nigra* extract, *Citrus Aurantium Dulcis* Peel Extract, *Tussilago farfara* leaf extract, *Verbena officinalis* extract, *Juniperus communis* fruit extract, *Echinacea angustifolia* extract, *Arnica montana* flower extract, *Mangifera Indica* Fruit Extract, *Mangifera indica* fruit extract, *Calendula officinalis* flower extract, Sine adipe lac, *Cucumis melo* fruit extract, *Jasminum Officinale* Flower Extract, *Salix Alba* Bark Extract, Bay laurel extract, *Calluna Vulgaris* Extract, *Tussilago farfara* extract, Pacific Sea Kelp Extract, *Jasminum Officinale* Extract, *Cinnamomum camphora formosana* wood extra, *Cedrus atlantica* extract, *Cederus atlantica* bark extract, *Commiphora myrrha* extract, *Plumeria alba* extract, *Phyllantus emblica* extract, *Centella asiatica* extract, *Boswellia carterii* extract, *Silybum marianum* extract, *Stellaria media* extract, *Baptisia Tinctoria* Extract, *Carbenia Benedicta* Extract, *Thymus Vulgaris* Extract, *Matricaria recutita* extract, *Trifolium pratense* flower extract, *Simmondsia chinensis* extract, *Olea europaea* leaf extract, *Polygonum Fagopyrum* Extract, *Ruta graveolens* extract, *Olea europaea* extract, *Malva sylvestris* flower extract, *Pimpinella anisum* extract, *Helianthus Annuus* Extract, *Morus Alba* Leaf Extract, *Iris Germanica* Extract, *Morus Alba* Extract, *Harpagophytum procumbens* extract, *Carica papaya* fruit extract, *Lonicera Caprifolium* Extract, *Papaver rhoeas* extract, *Bellis perennis* extract, *Rosa gallica* flower extract, *Papaver rhoeas* petal extract, *Carica papaya* fruit extract, *Citrus aurantifolia* extract, *Crataegus Monogyna* Extract, *Cinchona Pubescens* Extract, *Citrus Medica Limonum* Juice, *Nymphaea Odorata* Root Extract, *Melissa Officinalis* Distillate, *Macadamia Temifolia* Extract, Wine kern extract, *Triticum vulgare* bran extract, *Spiraea ulmaria* extract, *Zingiber officinale* root extract, *Trifolium pratense* extract, *Viola Odorata* Extract, *Hyssopus Officinalis* Extract, *Chelidonium Majus* Extract, *Agrimonia Eupatoria* Extract, *Aloe Barbadensis* Leaf Extract, *Tagetes Erecta* Extract, *Primula Veris* Extract, *Primrose Angelica Marigold* Extract, *Paeonia Albiflora* Extract, *Hibiscus sabdariffa* flower extract, *Nelumbium Speciosum* Extract, *Nymphaea odorata* root extract, *Nymphaea alba* extract, *Arctostaphylos Uva-ursi* Leaf Extract, *Annona reticulata* Extract, *Arctostaphylos uva ursi* leaf extract, *Zingiber Officinale* Extract, *Helichrysum Italicum* Extract, *Pogostemon Cablin* Extract, *Pterocarpus Santalinus* Extract, *Citrus aurantium amara* flower extraxt, *Cupressus Sempervirens* Extract, *Elettaria cardamomum* Extract, *Lavandula Angustifolia* Extract, *Vinva minor* extract, *Magnoliavine* fruit Extract, *Rubus fruticosus* fruit extract, *Purnus Avium* Extract, *Rubus idaeus* Extract, *Vaccinium myrtillus* extract, *Populus nigra* extract, *Vaccinium vitis-idaea* fruit extract, *Vaccinium macrocapron* extract, Chicory extract, *Nicotiana tabacum* leaf extract, *Trigonella Foenum Graecum* Extract, *Cydonia oblonga* extract, *Pryrus cydonia* extract, *Prunus Serotina* Bark Extract, *Petrocarpus Santalinus* Extract, *Citrus nobilis* Extract, *Punica granatum* extract, *Prunus armeniaca* Extract, *Macadamia Ternifolia* Seed Extract, *Anigozanthos Flavidus* Flower Extract, *Malpighia Punicifolia* Extract, *Sambucus Nigra* Berry Extract, *Actinidia chinensis* fruit extract, *Pyrus Malus* Extract, *Carica Papaya* Extract, *Hedychium Coronarium* Root Extract, *Passiflora incamata* fruit extract, *Macrocystis Pyrifera* Extract, *Cola acuminata* seed extract, *Theobroma Cacao* Extract, *Angelica Archangelica* Extract, *Ceratonia*

Siliqua Extract, *Asphdatus contaninatus* Extract, *Coriandrum sativum* extract, *Eruca sativa* Extract, *Nasturtium officinalis* extract, *Paullinia cupana* extract, *Gentiana lutea* Extract, Laurel Leaf Extract, *Crataegus oxycanthoides* extract, *Taraxacum officinale* extract, *Hippophae rhamnoides* extract, *Artemisia Absinthium* Extract, *Hippophae Rhamnoides* Kernel Extract, *Allium Sativum* Extract, *Allium Cepa* Extract, *Flores Graminis* extract, *Schinus molle* extract, *Curcuma longa* extract, *Curcuma longa* extract, *Pumus amygdalus amara* extract, *Ruscus aculeatus* extract, *Ruscus aculeatus* root extract, *Camelia Sinensis* Extract, *Cucumis sativus* extract, Algae Extract, *Chrysanthemum parthenium* extract, *Chlorella Vulgaris* Extract, *Chlorella emersonii* extract, *Nepeta Cataria* Extract, *Alpinia officinale* Extract, *Tamarindus Indica* Extract, *Vaccinium macrocarpon* fruit extract, *Sesamium indicum* extract, *Vaccinium angustifolium* fruit extract, *Gossiypium Herbaceum* Seed Extract, *Rosa damascena* flower water, *Santalum album* extract, *Citrus Aurantium Dulcis* Flower Water, *Salvia sclarea* extract, *Juniperus communis* destillate, *Vitis vinifera* extract, *Vitis vinifera* seed Extract, *Vitis vinifera* leaf extract, *Krameria triandra* extract, *Artemisia dracunulus* extract, *Krarmaeria triadra* root extract, *Myristica fragrans* extract, *Cinnamomum cassia* extract, *Citrus bergamia* Extract, *Cornus mas* extract, *Potentilla Erecta* Extract, *Echinacea purpurea* extract, *Prunus domestica* extract, *Prunus Amygdalus* Amara Peel Extract, *Quercus alba* Extract, *Levisticum officinale* extract, *Artemisia absinthum* extract, *Althaea officinalis* extract, *Pulmonaria officinalis* extract, *Eugenia caropyllus* (Clove) Flower Extract, *Salix alba* extract, *Rosa Damascena* Extract, *Citrus grandis* extract, *Citrus junos* extract, *Citrus medica limonum* extract, *Eugenia Caryophyllus* Extract, *Ilex paraguariensis* Extract, *Ilex paraguariens* extract, *Origanum vulgare* Extract, *Artemisia Vulgaris* Extract, *Cymbopogon schoenanthus* Extract, *Cynara Scolymus* Extract, *Rhodiolae roseae* extract, *Juglans Nigra* Shell Extract, *Iris Florentina* Extract, *Viola oforata* leaf extract, *Cola acuminata* extract, *Illicum verum* Extract, *Piper Nigrum* Extract, *Qauassia amara* extract, *Fagus sylvatica* extract, *Morus alba* bark extract, *Quercus robur* Extract, *Muira puma lignum, Muira puma lignum, Cinnamon* extract (*Cinnamomum* spp.), *Citrus Aurantium Amara* Peel Extract, *Citrus sinensis* peel extract, *Citrus medica limonum* peel extract, *Cananga Odorata* Extract, *Ficus carica* Extract, *Phoenix Dactylifera* Extract, *Mentha spicata* Extract, *Angostura* Extract, *Turnera Diffusa* Extract, Extract *acanthopanax senticosus* extract, *Melilotus officinalis* extract, *Echinacea* concentrate, Mate, Mate leaves, Roibush leaves, Ginger, *Cistus incanus* Extract, *Cistus incanus* dry extract, *Echinacea*, *Kakao* Extract conc., *Panax ginseng* extract, *Ginkgo biloba* leaf extract, *Swertia Chirata* Extract, *Centaruim erythraea* extract, *Menyanthes trifoliata* extract, *Tabeabuia impetignosa* bark extract, *Malva sylvestris* extract, *Petroselium crispum* Extract, *Peucedanum graveolens* extract, *Allium schoenoparsum* Extract, *Foeniculum vulgare* extract, *Nelumbium Speciosum* Flower Extract, *Nymphaea alba* flower extract, *Nymphaea alba* root extract, MeI Extract, *Oryza Sativa* Extract, *Coffea arabica* Extract, *Absinth Raft* Extracts, *Humulus lupulus* extract, *Thymus serpyllum* Extract, *Melissa officinalis* leaf extract, *Melia Azadirachta* Seed Extract, *Prunus domestica* fruit extract, *Piper nigrum* fruit extract, *Zanthoxylum pipertium* fruit extract, *Salvia trilobae* Herb Extract, *Ceratonia siliqua* extract, Deertongue Extract, *Quillaia saponaria* extract, *Elettaria cardamomum* extract, *Rheum palmatum* root extract, *Rosa Canina* Fruit Extract, *Nicotiana tabacum* flower extract and mixtures thereof.

Essential Oils:

Another class of actives that is highly desirable to carry/protect in the micro-particles of the composition of the invention is essential oils or mixtures thereof. Essential oils are selected from *Illicium Verum* Oil, *Humulus lupulus* oil, *Angelica archangelica* oil, *Valerian officinalis* Oil, *Ocimum basilicum* oil, *Pimenta racemosa* oil, *Citrus aurantium bergamia* oil, *Satureja hortensis* oil, *Acorus calamus* oil, *Elettaria cardamomum* oil, *Cypressus sempervirens* oil, *Juniperus* oil, *Citrus aurantium dulcis* oil, *Cistus ladaniferus* oil, *Cymbopogon nardus* oil, *Citronella* oil, *Citrus medica limonum* oil, *Copaiba officinalis* oil, *Coriandrum sativum* oil, *Peucedanum graveolens* oil, *Abies pectinata* oil, *Artemisia dracunculus* oil, *Eucalyptus Globulus* oil, *Eucalyptus globulus* oil, *Abies sibirica* oil, *Ferula galbaniflua* oil, *Pelargonium graveolens* oil, *Citrus grandis* oil, *Bulnesia sarmienti* oil, Strohblumenol, *Zingiber officinale* oil, *Hyssopus officinalis* oil, *Anthemis nobilis* oil, *Laurus camphora, Daucus carota* oil, *Pinus sylvestris* oil, *Mentha veridis* oil, Caraway oil, *Pinus mugo* oil, *Lavandula angustifolia* oil, Lemongrass oil, *Litsea cubeba* oil, *Laurus nobilis* oil, *Citrus nobilis* oil, *Salvia sclarea* oil, *Eugenia caryophyllus* leaf oil, *Eugenia caryophyllus* oil, *Citrus aurantium amara* flower oil, *Prunus amygdalus amara* oil, *Citrus aurantium dulcis* leaf oil, *Carum petroselinum* oil, *Mentha arvensis* oil, *Pimenta officinalis* oil, *Citrus aurantium amara* oil, *Citrus aurantuim dulcis* oil, Terpenes, limonene fraction, *Rosa damascena* oil, *Salvia officinalis* oil, *Apium graveolens* oil, *Artemisia vulgaris* oil, *Thuja occidentalis* oil, *Juniperus communis* oil, *Artemisia absinthium* oil, *Cinnamon zeylanicum* oil, *Levisticum officinale* oil, *Barosma betulina* oil, *Perilla ocymoides* oil, *Commiphora myrrha* oil, *Cananga odorata* oil, *Myroxylon pereirae* oil, *Eucalyptus citriodora* oil, *Myrtus communis* oil, *Achillea millefolium* oil, Orange oil, *Citrus aurantifolia* oil, *Myristica fragrans* oil, *Melaleuca alternifolia* oil, *Carum carvi* oil, *Allium sativum* oil, *Carum petriselinum* oil, *Cinnamomum sassia* oil, *Piper nigrum* oil, *Persea gratissima* oil, *Brassica nigra* oil, *Foeniculum vulgare* oil, *Boswellia serrata* oil, *Carum carvi* fruit extract, *Allium cepa* oil, *Origanum majorana* oil, Lemon oil Pelatrice, Niemöl, *Magnolia grandiflora* leaf extract, *Juniperus virginiana* oil, *Aniba rosaeodora* oil, Turpentine oil, *Prunus amygdalus* oil, *Copaifera officinalis* resin, *Santalum album* oil, *Myrocarpus frondosus* oil, *Croton glabellus* oil, Cubeb oil, *Cuminum cyminum* oil, *Artemisia pallens* oil, Elemi oil, *Alpinia officinalis* oil, Geranium oil, *Gurjun balsam* oil, *Cistus* oil, *Chamomilla recutita* oil, *Ormenis multicaulis* oil, *Lavandula hybridis* oil, Opoponax, *Pogostemon cablin* oil, *Pinus palustris* oil, *Mentha pulegium* L., *Rosmarinus officinalis* oil, *Tagetes* oil, *Thymus vulgaris* oil, *Vetivera zizanoides* oil, *Cananga odorata* oil, *Cinnamomum zeylanicum* oil and mixtures thereof.

Micro-Particle Producing Machines:

Colloid Mill High Energy Micro-Particle Producing Machines:

Colloid mills are well known in the art. Any type of colloid mill can be used for for the process of the subject invention. A preferred type of colloid mill is a Fryma Karuma colloid mill commercially available from Fryma-Koruma AG Switzerland. A more preferred type of colloid mill is a Sonic Corporation colloid mill commercially available from Sonic Corporation 1 Research Drive, Stratford, Conn., 06615 USA.

Other High Energy Micro-Particle Producing Machines:
1. High energy fluid shear mixers e.g. high shear emulsifier mixers.

These other types of high energy micro-particle producing machines cannot be used for the process of U.S. Pat. No. 4,152,272, but can be used for the process of the subject invention:

Silverson L5 series of laboratory mixers available from Silverson Machines Ltd, Waterside, Chesham, Bucks HP5 1PQ, UK.

An Ultra-Turrax® emulsifying mixer Type T25 basic available from IKA Werke GmbH & Co KG, Germany.

2. Machines similar to the Sonic Sonolator micro-particle producing machine available from Sonic Corporation (see above).

The micro-particle of the composition of the invention comprising a dispersion matrix with an active dispersed therein can be used in various applications and examples of these applications are given below.

i. Laundry
   i. Liquid Detergents
   ii. Powdered Detergents
   iii. Fabric Conditioners
   iv. Specialist treatment products (e.g., softening products, whitening agents, stain removal products)
   v. Laundry Drier Sheets—coated non-woven fabrics
ii. Personal Care
   i. Personal Deodourants
   ii. Feminine Hygiene products (paper/non-woven fabric coatings)
   iii. Hair Care treatments
   iv. Shampoos
   v. Cosmetics
   vi. Skin Creams/Moisturisers
   vii. Hair conditioners
   viii. Oral care—tooth pastes, tooth whitening products, mouth washes
   ix. Solid bar soaps
iii. Home Care
   i. Air Care—air fresheners and room de-odourisers, fragranced candles
   ii. Vacuum Cleaner Freshener
   iii. Anti-bacterial Agent delivery—e.g., anti-bacterial Cleaner
   iv. Shoe Fresheners (including anti bacterial agent delivery)
   v. Cleaning products
   vi. Car Air fresheners
   vii. Toilet Cleaning Products, e.g., under the rim toilet blocks and in-tank cleaning products
   viii. Surface Modifying Products—furniture polishes, car polishes, floor polishes etc
   ix. Incense Sticks
   x. Cat Litter deodoriser
   xi. Wardrobe Fresheners
iv. Pharmaceutical, Medical and Veterinary
   i. Trans dermal drug or active delivery
   ii. Wound dressings
   iii. Therapeutic active delivery
   iv. Vitamin delivery
v. Surface coatings to paper (cellulose), non-woven films (PP), plastic laminates and metallic foils, to Cat Litter (both mineral and paper based)
vi. Food & Flavours
   i. Beverages
   ii. Confectionary and Bakery
   iii. Processed Meat products
   iv. Barbeques flavourings
   v. Dairy Products
   vi. Chewing Gum
   vii. Savoury Snacks (e.g., potato chips)
vii. Insect Control
   i. Insecticides
   ii. Acaricides/Miticides
   iii. Insect Repellents
   iv. Pheromone delivery
viii. Other Miscellaneous
   i. Flavoured Tobacco

EXAMPLES

Example I

In this cold process Example the non-frangible starting material composition was Bell MikroChips® Alpinia in solid block form. Bell MikroChips® Alpinia in solid block form and all other types of Bell MikroChips® used as the non-frangible starting material composition in the following Examples herein are commercially available from Bell Flavors and Fragrances-Europe, Schimmel-Strasse1. 04205, Leipzig (Miltitz), Germany. The dispersion matrix of Bell MikroChips® Alpinia as used is formed of a C22 fatty alcohol with the Alpina fragrance dispersed therein. The Alpina fragrance is a proprietary blend of aroma chemicals and essential oils chosen from the list quoted above. Then 120 g of Polyoxyethylene(20) sorbitan monooleate non-ionic surfactant commercially available as Tween® 80 from ICI Americas, Inc. was mixed with 2580 g of cold water to provide a concentration of 4% by weight of the Polyoxyethylene(20) sorbitan monooleate surfactant in the dispersion liquid of the final product. The cold water had a temperature of 10-15° C. The cold water surfactant mixture was then placed into a FrymaKoruma Toothed Colloid Mill, Type MZ 80 available from FrymaKoruma AG, Switzerland, the FrymaKoruma Colloid Mill being provided with a water cooling jacket. To this cold water surfactant mixture in the colloid mill was added 300 g of the solid (i.e. unmelted) Bell MikroChips® Alpinia to provide a concentration of 10% by weight of the Bell MikroChips® Alpinia in the water surfactant mixture. Then about 0.1% by weight of a preservative was added to prevent microbiological contamination of the dispersion. The preservative was "Nipagin M" which is Methyl 4-Hydroxybenzoate from Clariant International Ltd, Functional Chemicals Division, 4132 Muttenz 1, Switzerland.

The colloid mill was then turned on and milling took place for 5 minutes with water cooling of the colloid mill such that the temperature of the mixture being milled did not exceed 45° C. during the milling. Then the mill was turned off and the product composition comprising a plurality the micro-particles of the composition of the invention dispersed in the liquid in which they were colloid milled was taken out.

Figure 6:
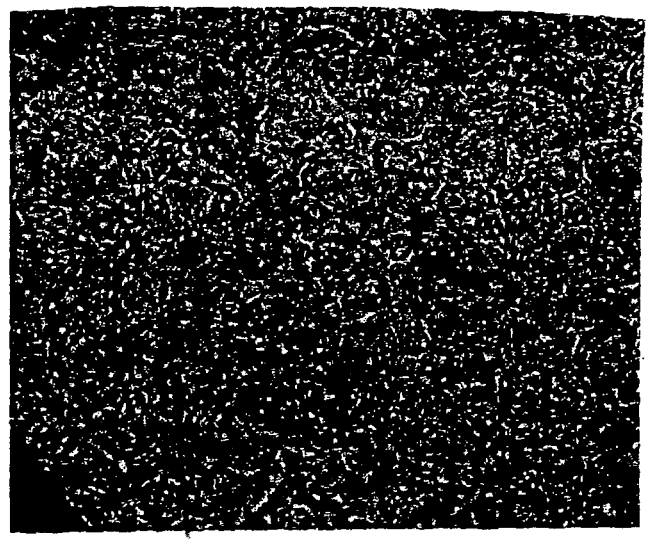
FIG. 6 shows a cut out part of a photomicrograph (magnification 400 fold) showing micro-particles of the composition of the invention produced by the method of Example 1 herein.
Figure 6A:
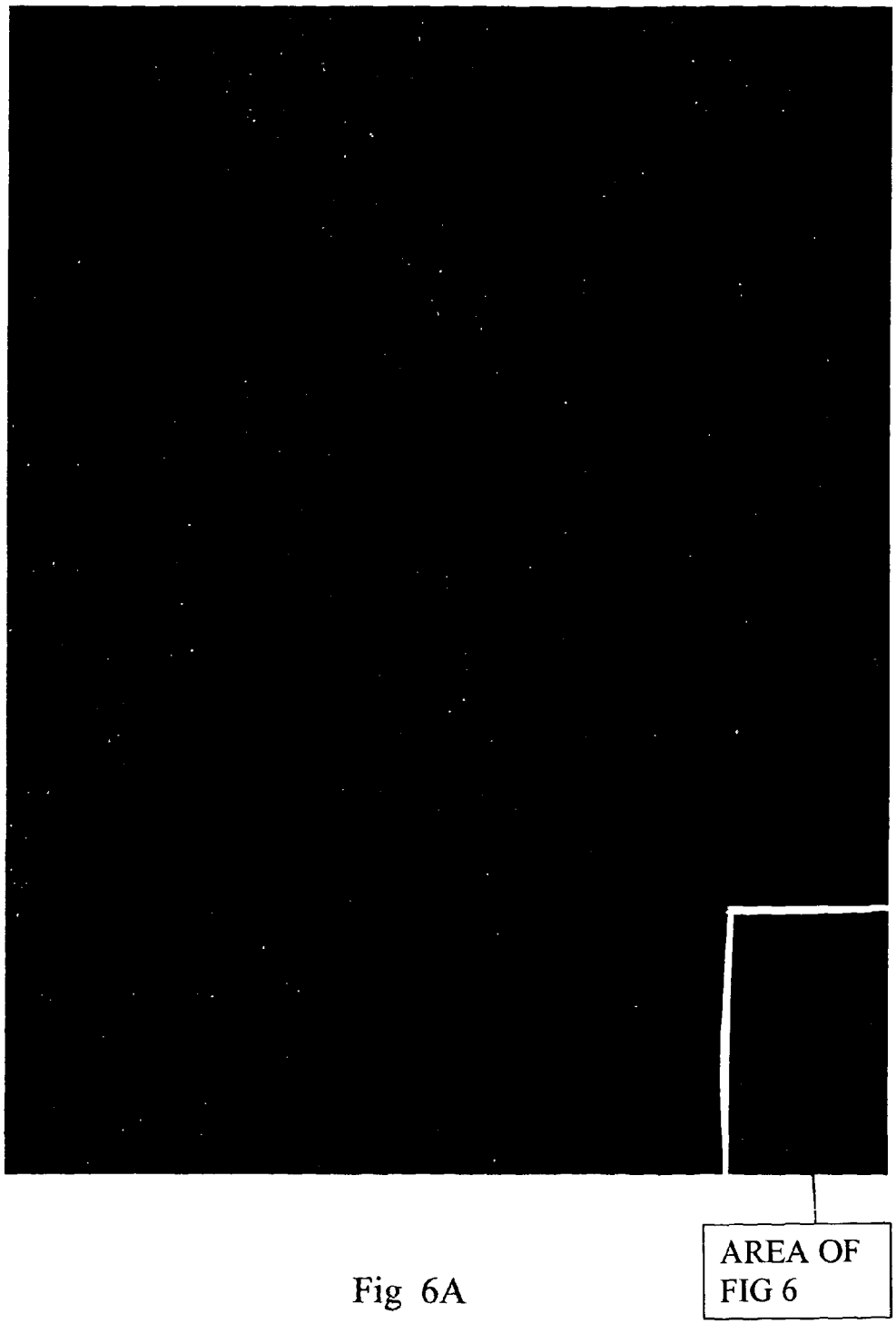
FIG. 6A shows the full photomicrograph of FIG. 6.
Figure 7:
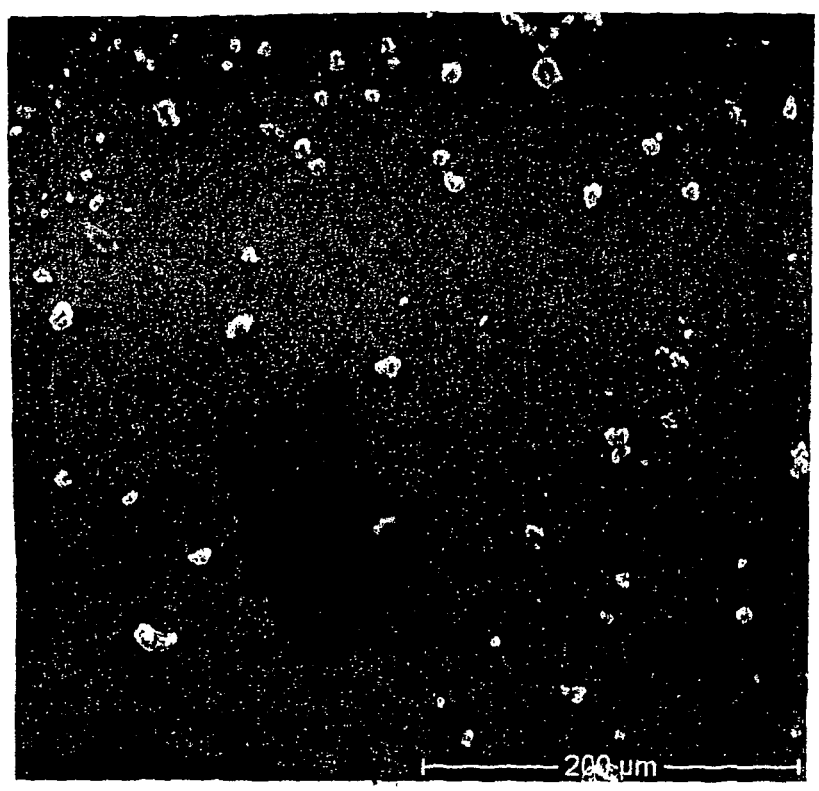
FIG. 7 is an electronmicrograph with a 200 micrometer scale line marked on the electronmicrograph showing micro-particles of the composition of the invention produced by the method of Example 1 herein.
Figure 8:
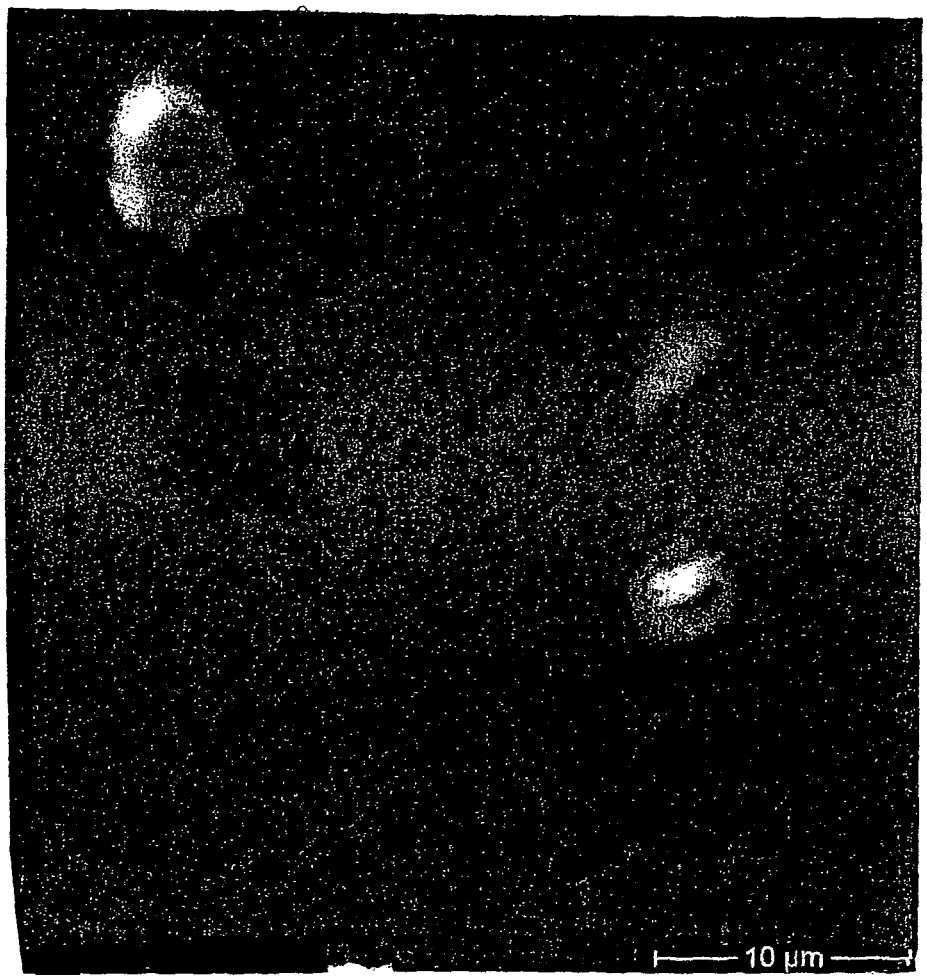
FIG. 8 is an electronmicrograph with a 10 micrometer scale line marked on the electronmicrograph showing micro-particles of the composition of the invention produced by the method of Example 1 herein.
Figure 9:
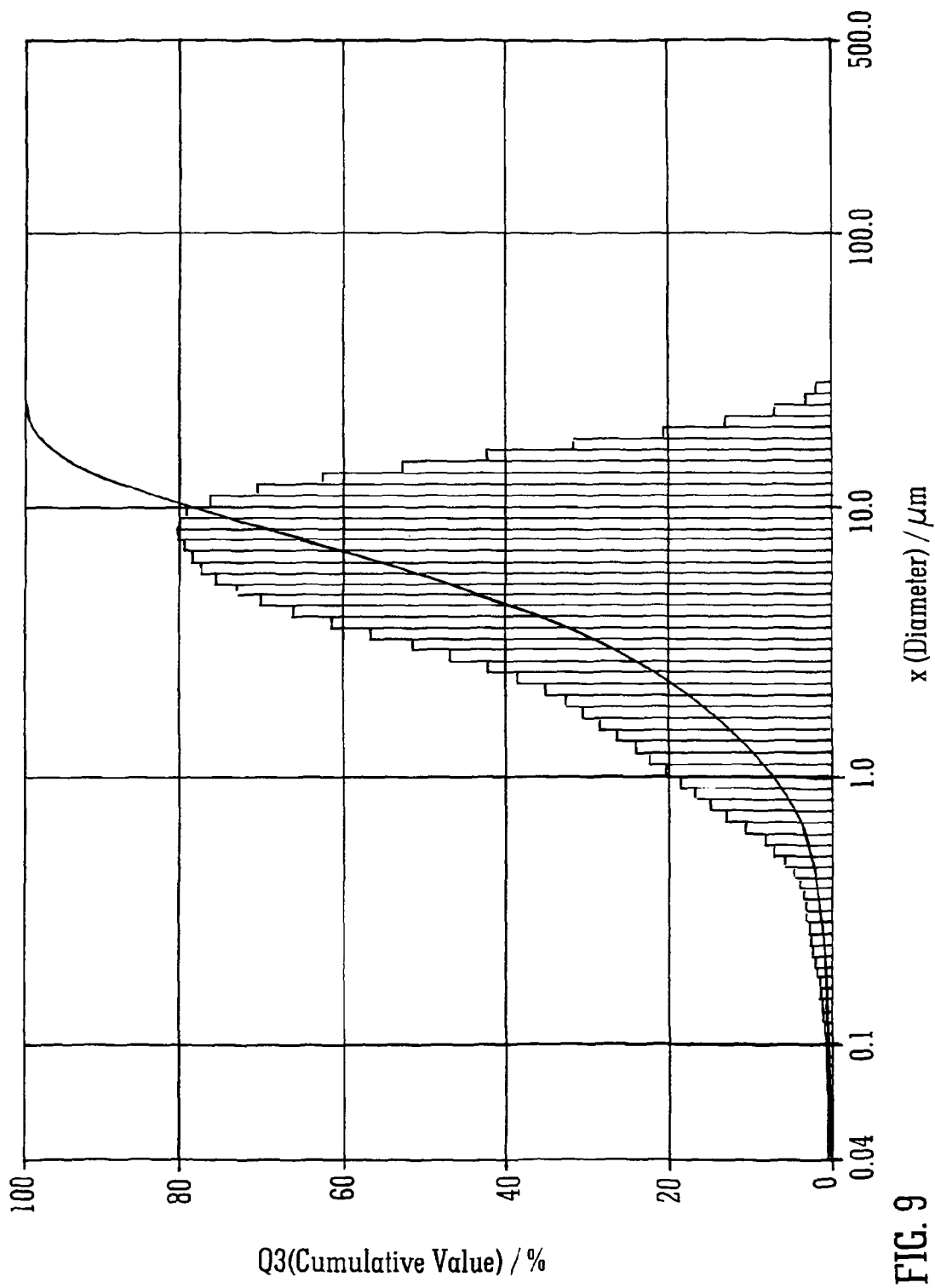
FIG. 9 is a size distribution curve of the micro-particles of the composition of the invention produced by the method of Example I herein.

A light microscopy photomicrograph slide of this Example 1 product composition comprising a plurality the micro-particles of the composition of the invention dispersed in the liquid in which they were colloid milled with magnification 400× is shown in FIGS. 6 and 6A. An electron microscopy photomicrograph slide of this Example I product composition comprising a plurality the micro-particles of the composition of the invention dispersed in the liquid in which they were colloid milled with a 200 micrometer scale line marked on the photomicrograph is shown in FIG. 7. An electron microscopy photomicrograph slide of this product composition of Example 1 comprising a plurality the microparticles of the composition of the invention dispersed in the liquid in which they were colloid milled with a 10 micrometer scale line marked on the photomicrograph is shown in FIG. 8. A sample of this product composition was then provided to Quantachrome GmbH & Co. KG, Rudolf-Diesel-Strasse 12, D-85235 Odelzhausen and a size distribution curve of the micro-particles of the composition of the invention was produced which is shown in FIG. 9 hereof. Quantachrome GmbH & Co. KG used the following procedure to measure the size of the micro-particles of the composition of the invention and to produce this size distribution curve of the micro-particles of the composition of the invention. In measuring the size of the micro-particles of the composition of the invention Quantachrome conducted the measurements in accordance with International Standard ISO 13320-1 (First Edition Jan. 11, 1999) entitled 'Particle size analysis laser diffraction methods'. All particle size measurements were made using a Cilas 1064 laser diffraction particle size analyzer available from Cilas, 8 avenue Buffon, 45063, Orleans, France. In all cases measurements were carried out in wet mode of the Cilas 1064 analyser. In all cases for evaluation purposes the Fraunhofer model was used.

A portion of the product sample provided to Quantachrome (product of the method of the invention comprising a plurality the micro-particles of the composition of the invention dispersed in their dispersion liquid) was subjected to ultrasonification for 60 seconds at 50 W. The ultrasonified measurement sample was then introduced into the Cilas 1064 analyser and a check was made to see if the % obscuration of the sample was between 1 and 30%, preferably between 10-20%. Reliable measurements can be made within these ranges of % obscuration. The % obscuration is the % reduction of laser intensity in passing the laser radiation through the sample. If the % obscuration is over 30% the sample should be diluted with deionized water and preferably dilution should be made so that the % obscuration is between 10-20%. Then the measurements were taken and the distribution curve as shown in the examples (see FIG. 9 for the curve for this Example 1) were plotted to show the size distributions of the micro-particles of the composition of the invention. In this example 1 measurement the obscuration was 17%.

As can be seen a majority of the micro-particles shown in FIG. 9 have a particle size of from 1-10 micrometers. The electronmicrographs were produced by Quantachrome.

Example 2

Figure 10:
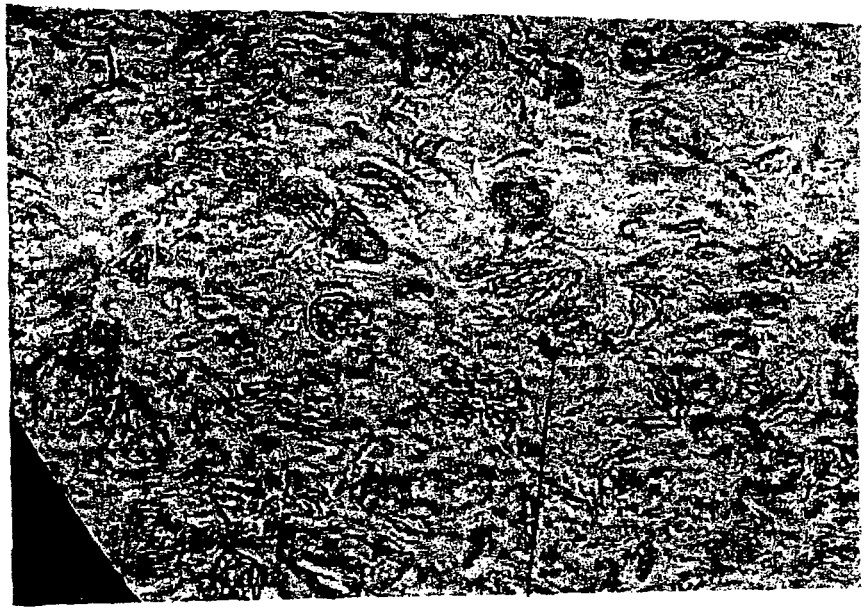
FIG. 10 shows a cut out part of a photomicrograph (magnification 400 fold) showing micro-particles of the composition of the invention produced by the method of Example 2 herein.
Figure 10A:
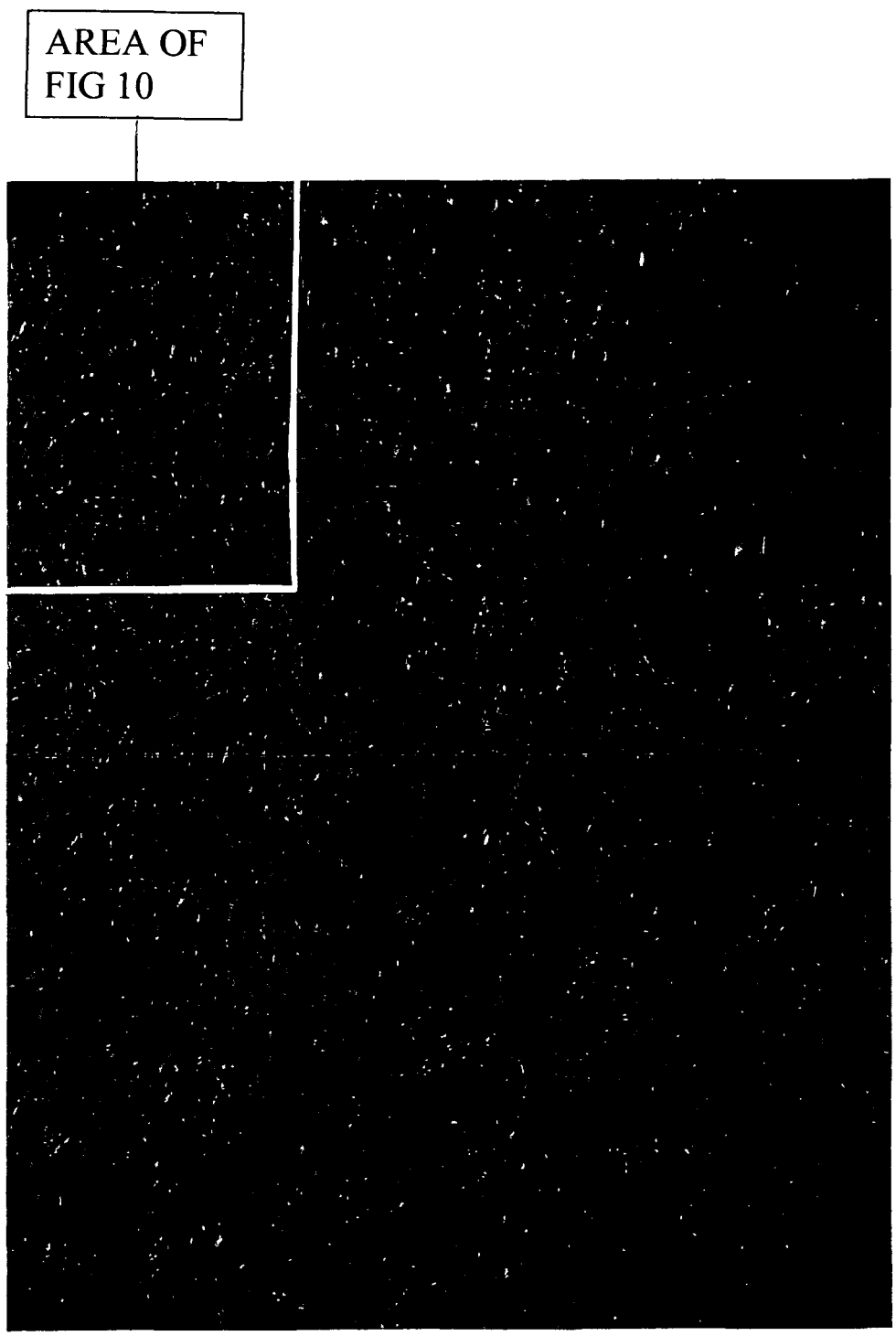
FIG. 10A shows the full photomicrograph of FIG. 10.
Figure 11:
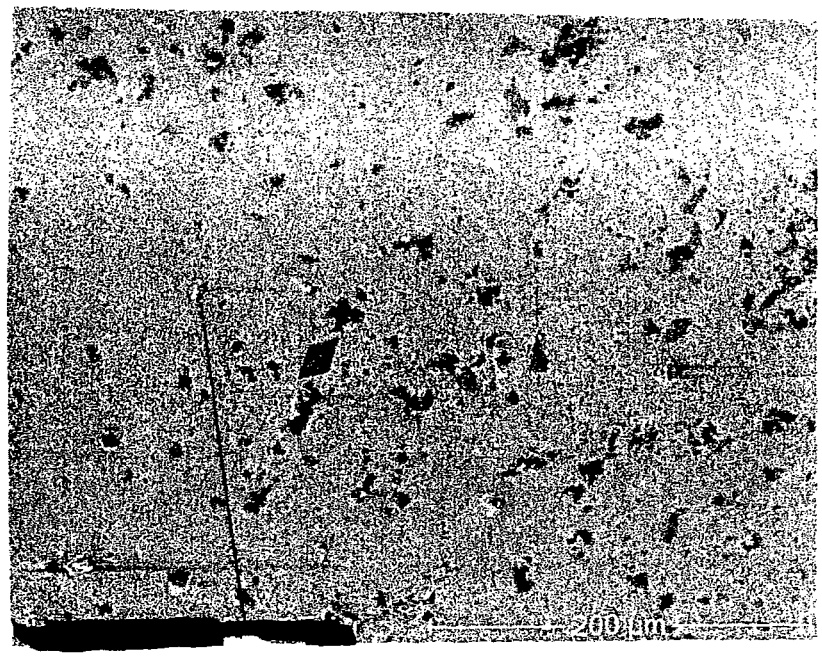
FIG. 11 is an electronmicrograph with a 200 micrometer scale line marked on the electronmicrograph showing micro-particles of the composition of the invention produced by the method of Example 2 herein.
Figure 12:
FIG. 12 is an electronmicrograph with a 60 micrometer scale line marked on the electronmicrograph showing micro-particles of the composition of the invention produced by the method of Example 2 herein.
Figure 13:
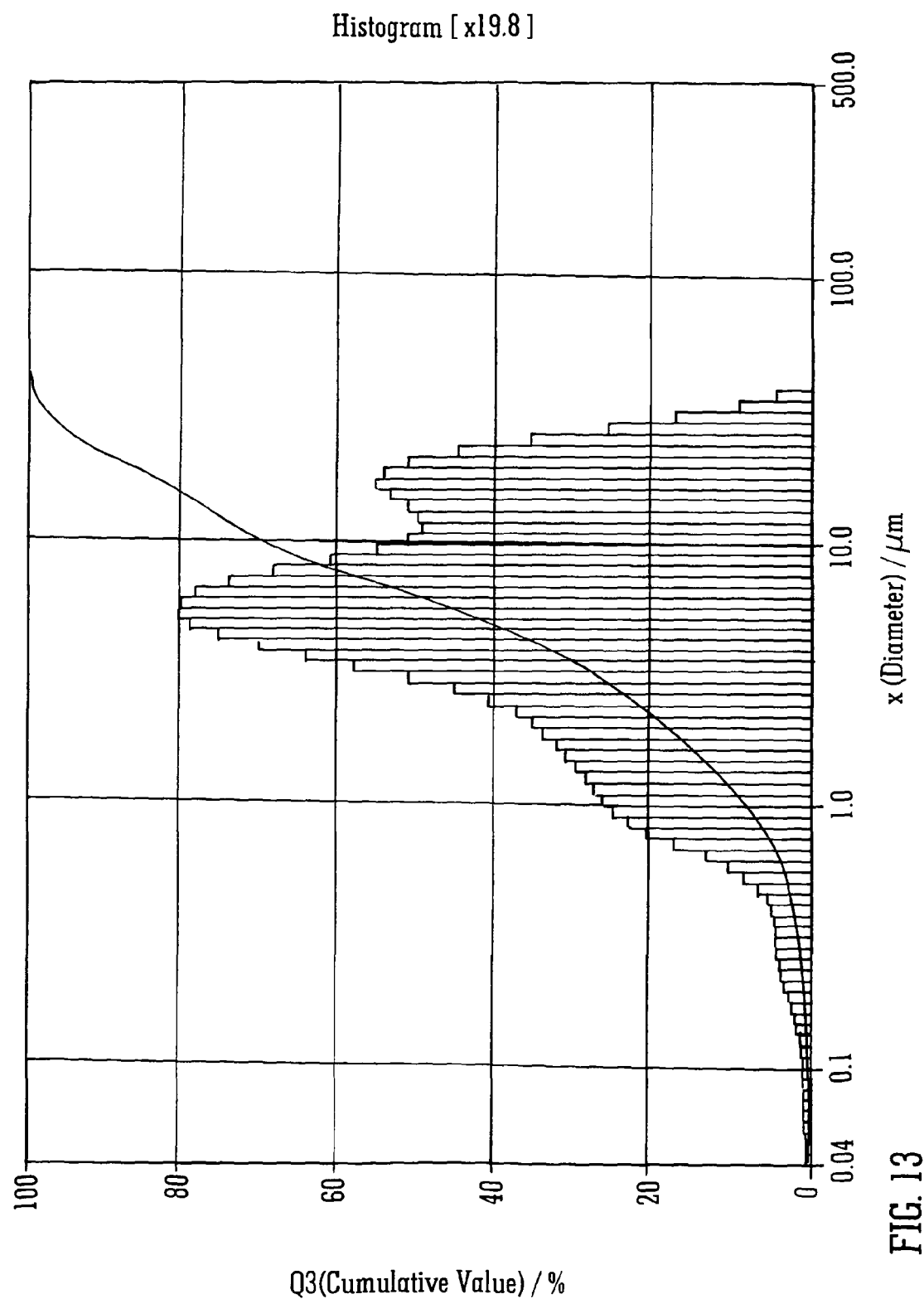
FIG. 13 is a size distribution curve of the micro-particles of the composition of the invention produced by the method of Example 2 herein.

In this process of the subject invention the starting material composition was Bell MikroChips® Alpinia the same non-frangible starting material composition as used in Example 1 hereof. These Bell MikroChips® Alpinia blocks were melted by heating to 80° C. and then held ready for use in melted form at 80° C. Then 120 g of Tween 80 as used in Example I was mixed with 1800 g of hot water. The hot water had a temperature of 90° C. The hot water surfactant mixture was then placed into a FrymaKoruma Toothed Colloid Mill of the same type as was used in Example I and the hot water surfactant mixture was held at a temperature of 90° C. The melted Bell MikroChips® Alpinia at 80° C. was then added to the hot water surfactant mixture in the colloid mill. During a first stage of milling the colloid mill was then turned on and milling of the hot mixture at a hot mixture temperature of about 85° C. took place for 1-2 minutes. Then cold water was commenced to pass through the cooling jacket of the mill and a further 780 grams of cold water was added whilst the mill was running during a second stage of milling to reduce the temperature of the mixture being milled to temperature of about 45° C., (below the melting temperature of the C22 fatty alcohol dispersion matrix of the Bell MikroChips®). The total amount of water added including the second batch of added water was 2580 g (the same amount as used in Example I) such that the concentrations of ingredients were the same as used in Example I. A light microscopy photomicrograph slide of this Example 2 product composition comprising a plurality the micro-particles of the composition of the invention dispersed in the liquid in which they were colloid milled with magnification 400× is shown in FIGS. 10 and 10A. An electron microscopy photomicrograph slide of this Example 2 product composition comprising a plurality the micro-particles of the composition of the invention dispersed in the liquid in which they were colloid milled with a 200 micrometer scale line marked on the photomicrograph is shown in FIG. 11. An electron microscopy photomicrograph slide of this product composition of Example 2 comprising a plurality the micro-particles of the composition of the invention dispersed in the liquid in which they were colloid milled with a 60 micrometer scale line marked on the photomicrograph is shown in FIG. 12. The electronmicrographs were produced by Quantachrome. A sample of this Example 2 product composition was then provided to Quantachrome GmbH and a size distribution curve of the micro-particles of the composition of the invention was produced in the same way as for Example I which is shown in FIG. 13 hereof. The % obscuration during the particle size measurement was 13%. As can be seen a majority of the micro-particles shown in FIG. 13 have a particle size of from 1-10 micrometers.

Example 3

Figure 15:
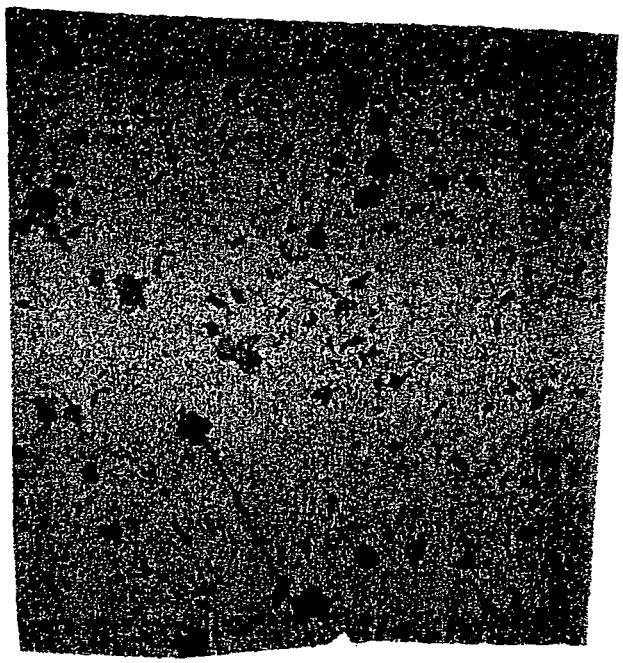
FIG. 15 is an electronmicrograph with a 200 micrometer scale line marked on the electronmicrograph showing micro-particles of the composition of the invention produced by the method of Example 3 herein.
Figure 16:
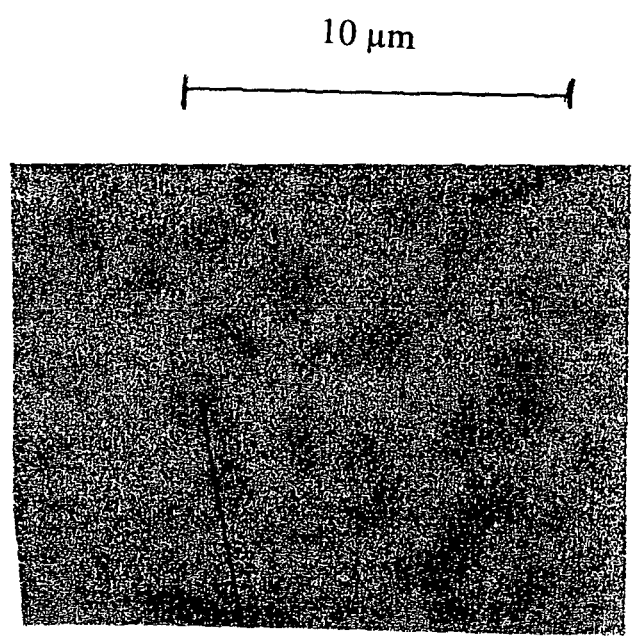
FIG. 16 is an electronmicrograph with a 10 micrometer scale line marked on the electronmicrograph showing micro-particles of the composition of the invention produced by the method of Example 3 herein.
Figure 17:
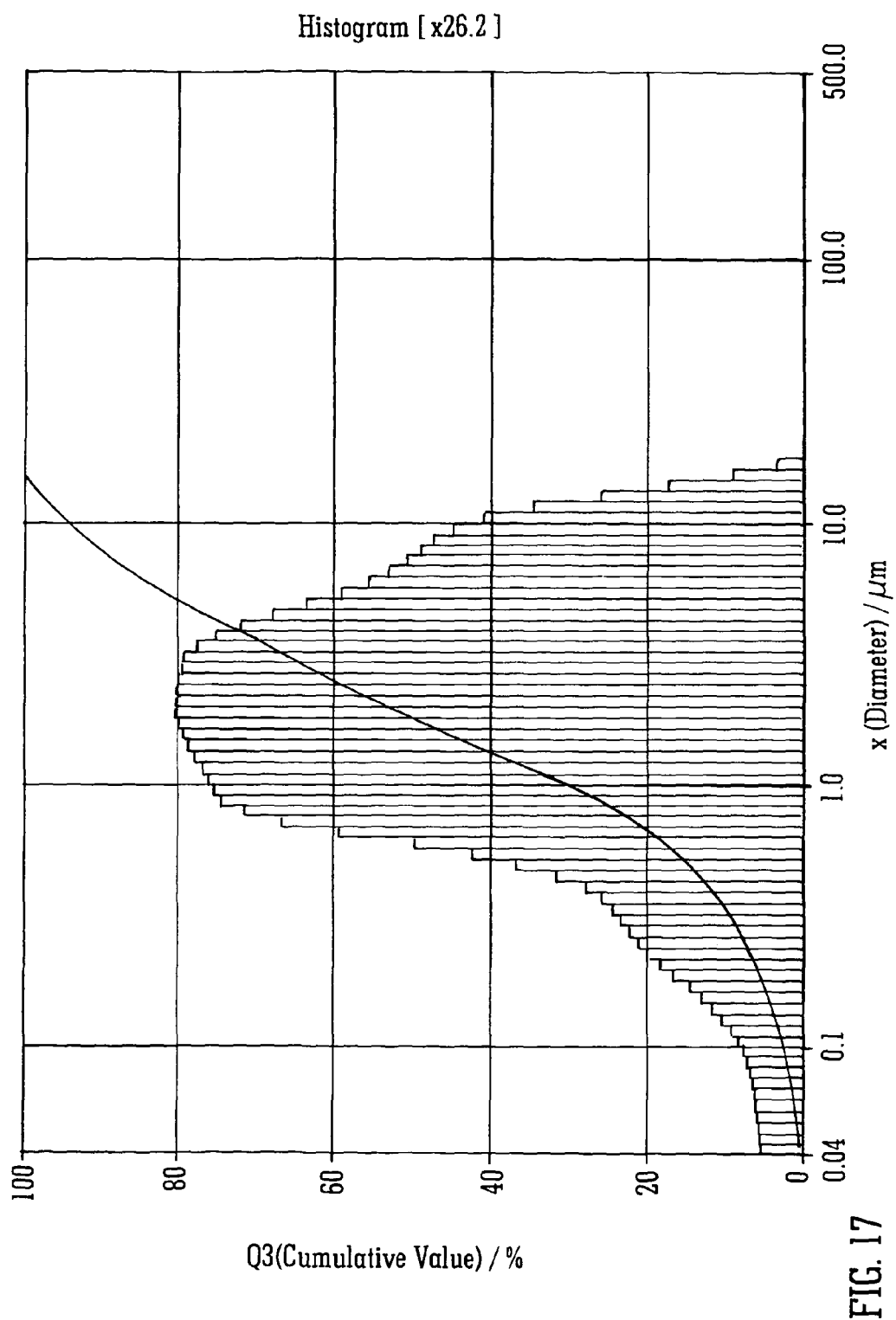
FIG. 17 is a size distribution curve of the micro-particles of the composition of the invention produced by the method of Example 3 herein.

The cold process product micro-particles of this Example 3 were prepared in the same way as the product micro-particles of Example 1 were prepared except that the non-frangible starting material composition was Bell Mikro-Chips® Coolmint rather than Bell MikroChips® Alpinia. Bell MikroChips® Coolmint are the same as Bell Mikro-Chips® Alpinia except that the Coolmint active is carried rather than the Alpina active. The Coolmint flavor is non-toxic to humans such that it can be used as a food flavoring additive and is a proprietary blend of flavor chemicals chosen from the list quoted above. A light microscopy photomicrograph slide of this Example 3 product composition comprising a plurality the micro-particles of the composition of the composition of the invention dispersed in the liquid in which they were colloid milled with magnification 400× is shown in FIGS. 14 and 14A. An electron microscopy photomicrograph slide of this Example 3 product composition comprising a plurality the micro-particles of the composition of the invention dispersed in the liquid in which they were colloid milled with a 200 micrometer scale line marked on the photomicrograph is shown in FIG. 15. An electron microscopy photomicrograph slide of this product composition of Example 3 comprising a plurality the micro-particles of the composition of the invention dispersed in the liquid in which they were colloid milled with a 10 micrometer scale line marked on the photomicrograph is shown in FIG. 16. The electronmicrographs were produced by Quantachrome. A sample of this Example 3 product composition was then provided to Quantachrome GmbH and a size distribution curve of the micro-particles of the composition of the invention was produced in the same way as for Example I which is shown in FIG. 17 hereof. The % obscuration during the particle size measurement was 9%. As can be seen a majority of the micro-particles shown in FIG. 17 have a particle size of from 1-10 micrometers.

Example 4

Figure 18:
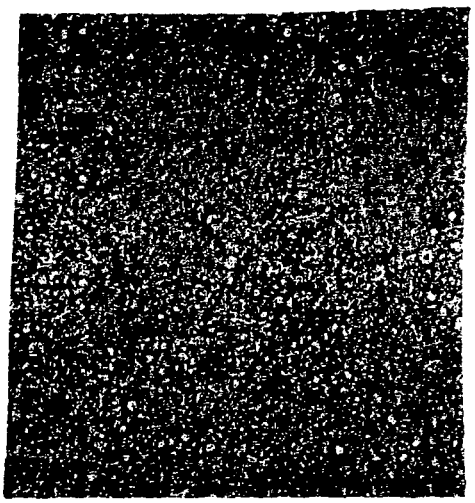
FIG. 18 shows a cut out part of a photomicrograph (magnification 400 fold) showing micro-particles of the composition of the invention produced by the method of Example 4 herein.
Figure 19:
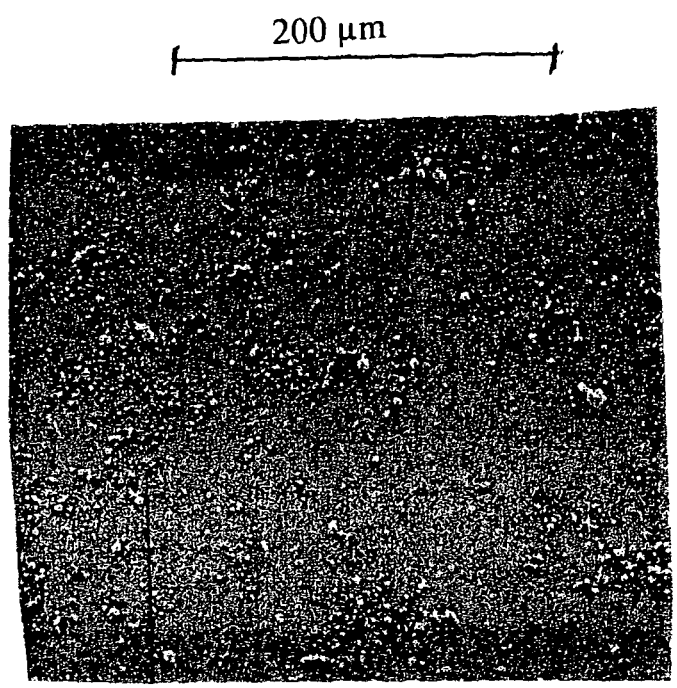
FIG. 19 is an electronmicrograph with a 200 micrometer scale line marked on the electronmicrograph showing micro-particles of the composition of the invention produced by the method of Example 4 herein.
Figure 20:
FIG. 20 is an electronmicrograph with a 10 micrometer scale line marked on the electronmicrograph showing micro-particles of the composition of the invention produced by the method of Example 4 herein.
Figure 21:
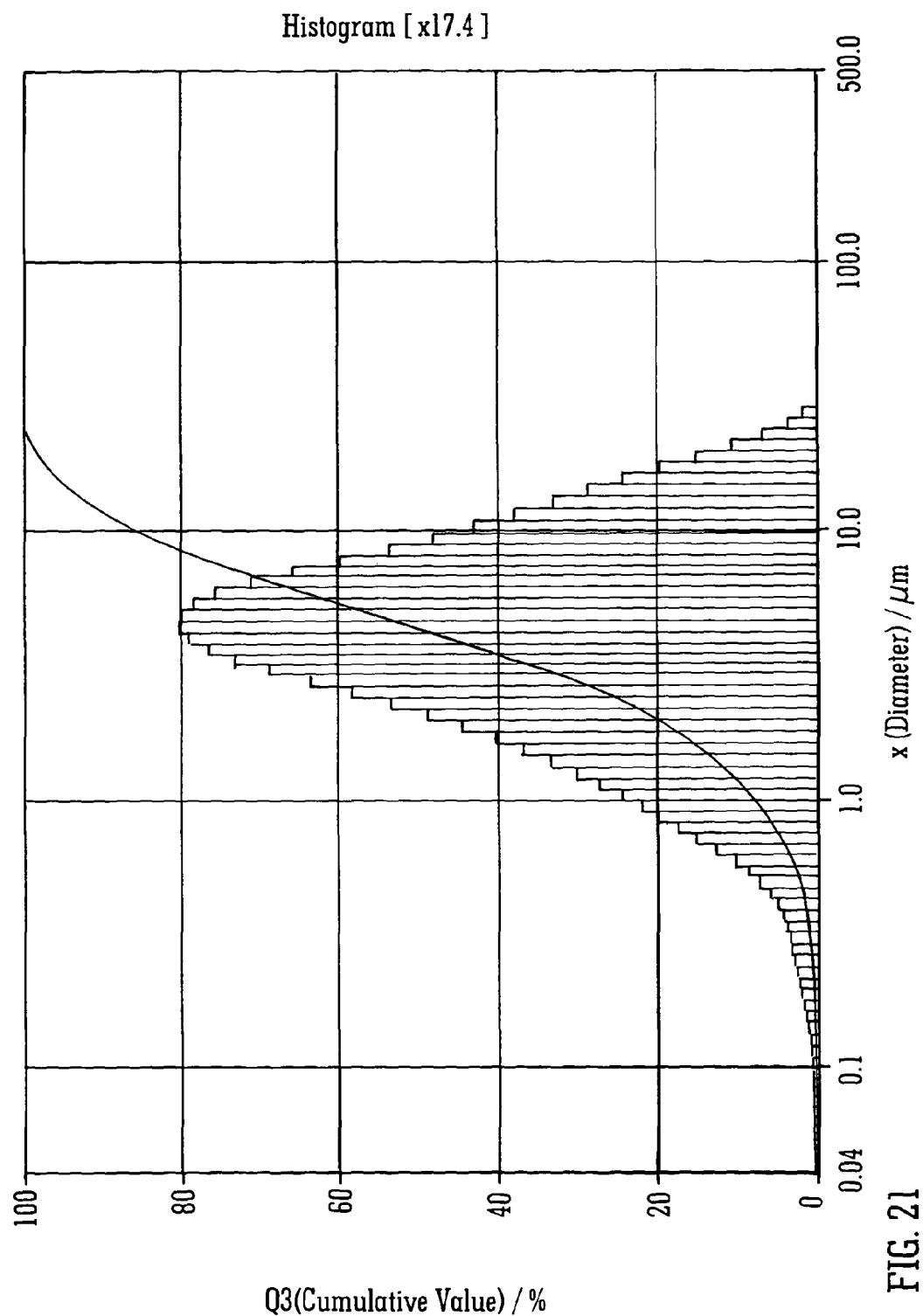
FIG. 21 is a size distribution curve of the micro-particles of the composition of the invention produced by the method of Example 4 herein.

In this process of the subject invention of Example 4 the starting material composition was Bell MikroChips® Orange Peel F. Bell MikroChips® Orange Peel F are the same as Bell MikroChips® Alpinia except that the Orange Peel F active is carried rather than the Alpina active. The Orange Peel F active is a proprietary blend of aroma chemicals and essential oils chosen from the list quoted above. Then 50 g of the Bell MikroChips® Orange Peel F blocks were melted. Then 12.5 g of sorbitan monooleate surfactant commercially available as Span® 80 from Croda International Plc, Cowick Hall, Snaith, Goole, East Yorkshire, DN14 9AA, UK was mixed with 437.5 g of hot water in a beaker at a temperature of 90° C. to provide a concentration of 2.5% by weight of the sorbitan monooleate surfactant in the hot water. To this hot water surfactant mixture in the beaker was added the 50 g of the melted Bell MikroChips® Orange Peel F a to provide a concentration of 10% by weight of the Bell MikroChips® Orange Peel F in the hot water surfactant mixture the addition taking place during homogenization with an Ultra-Turrax® emulsifying mixer Type T25 basic available from IKA Werke GmbH & Co KG, Germany. Homogenization was continued until the temperature of the mixture fell below 45° C. to produce the product composition comprising a plurality the micro-particles of the composition of the invention dispersed in the liquid in which they were homogenized. A light microscopy photomicrograph slide of this Example 4 product composition comprising a plurality the micro-particles of the composition of the invention dispersed in the liquid in which they were homogemized with magnification 400× is shown in FIGS. 18 and 18A. An electron microscopy photomicrograph slide of this Example 4 product composition comprising a plurality the micro-particles of the composition of the invention dispersed in the liquid in which they were homogenized with a 200 micrometer scale line marked on the photomicrograph is shown in FIG. 19. An electron microscopy photomicrograph slide of this product composition of Example 4 comprising a plurality the micro-particles of the composition of the invention dispersed in the liquid in which they were homogenized with a 10 micrometer scale line marked on the photomicrograph is shown in FIG. 20. The electronmicrographs were produced by Quantachrome. A sample of this Example 4 product composition was then provided to Quantachrome GmbH and a size distribution curve of the micro-particles of the composition of the invention was produced in the same way as for Example I which is shown in FIG. 21 hereof. The % obscuration during the particle size measurement was 14%. As can be seen a majority of the micro-particles shown in FIG. 21 have a particle size of from 1-10 micrometers.

Example 5

The cold process product micro-particles of this Example 5 were prepared following the preparation pattern of cold process Example I with the following exceptions. The non-frangible starting material composition was Bell MikroChips® Fresh Cotton/Jasmin rather than Bell MikroChips® Alpinia. Bell MikroChips® Fresh Cotton/Jasmin are the same as Bell MikroChips® Alpinia except that the Fresh Cotton/Jasmin active is carried rather than the Alpina active. The Fresh Cotton/Jasmin active is a proprietary blend of aroma chemicals and essential oils chosen from the list quoted above. Also a 2.5 inch colloid mill powered by a 1.5 HP motor available from Sonic Corporation, Stratford, Conn., USA, was used rather than the FrymaKoruma colloid mill of Example I. In this example 35 grams of the Bell MikroChips® Fresh Cotton/Jasmin was dispersed in 700 grams of All 2× Super Concentrated (unperfumed) Laundry Liquid Detergent which is commercially available in US supermarkets. The Bell MikroChips® Fresh Cotton/Jasmin was dispersed into the Laundry Liquid detergent using a simple low speed paddle mixer. The resulting dispersion was then fed by gravity to the colloid mill. The colloid mill was set at the maximum gap setting for this equipment. The product was collected at the discharge port. A light microscopy photomicrograph slide of this Example 5 product composition comprising a plurality the micro-particles of the composition of the invention dispersed in the liquid in which they were colloid milled is shown in FIG. 22. An electron microscopy photomicrograph slide of this Example 5 product composition comprising a plurality the micro-particles of the composition of the invention dispersed in the liquid in which they were colloid milled with a 200 micrometer scale line marked on the photomicrograph is shown in FIG. 23. An electron microscopy photomicrograph slide of this product composition of Example 5 comprising a plurality the micro-particles of the composition of the invention dispersed in the liquid in which they were colloid milled with a 40 micrometer scale line marked on the photomicrograph is shown in FIG. 24. The electronmicrographs were produced by Quantachrome. A sample of this Example 5 product composition was then provided to Quantachrome GmbH and a size distribution curve of the micro-particles of the composition of the invention was produced in the same way as for Example I which is shown in FIG. 25 hereof. The % obscuration during the particle size measurement was 17%. As can be seen a majority of the micro-particles shown in FIG. 25 have a particle size of from 1-10 micrometers.

Example 6

The cold process product micro-particles of this Example 6 were prepared in the same way as the product micro-particles of Example 3 were prepared except that the liquid in which they were colloid milled was glycerol instead of Polyoxyethylene(20) sorbitan monooleate surfactant in cold water. A light microscopy photomicrograph slide of this Example 6 product composition comprising a plurality the micro-particles of the composition of the invention dispersed in the liquid in which they were colloid milled with magnification 400× is shown in FIGS. 26 and 26A. An electron microscopy photomicrograph slide of this Example 6 product composition comprising a plurality the micro-particles of the composition of the invention dispersed in the liquid in which they were colloid milled with a 200 micrometer scale line marked on the photomicrograph is shown in FIG. 27. The electronmicrograph was produced by Quantachrome. A sample of this Example 6 product composition was then provided to Quantachrome GmbH and a size distribution curve of the micro-particles of the composition of the invention was produced in the same way as for Example I which is shown in FIG. 29 hereof. The % obscuration during the particle size measurement was 18%. As can be seen a majority of the micro-particles shown in FIG. 29 have a particle size of from 1-10 micrometers.

Example 7

In this process in accordance with the subject invention of Example 7 the high energy micro-particle producing machine used was a 2.5 inch Sonic bench top colloid mill supplied by Sonic Corporation whose address is set out above. This mill comes fitted with a laboratory mixer for use in its premix hopper (i.e. 'feeding funnel'). This mill was further adapted as follows. A stopcock was fitted below the feeding funnel between feeding funnel and mill such that the stopcock could be either closed to close off the flow of fluid from the feeding funnel into the mill or the stopcock could be opened to allow the flow of fluid from the feeding funnel into the mill. Furthermore the feeding funnel was equipped with an immersion heater, the heating part of which could be introduced into the fluid contained within the feeding funnel when the stopcock was in the closed position to heat the fluid contained in the feeding funnel to a desired temperature. The stopcock below the feeding funnel was closed to close off the flow of fluid from the feeding funnel into the mill. Then a mixture of 720 g deionised water, preserved with 0.1% Nipagin M, 80 g Tween, 960 g L-Carvone perfume (active) and 240 g C22 fatty alcohol wax or wax-like dispersion matrix material was heated by the immersion heater to 75° C. in the feeding funnel whilst stirring with the laboratory mixture. The ratio of the above stated amount of perfume to C22 fatty alcohol wax or wax-like dispersion matrix material (960 g L-Carvone perfume to 240 g C22 fatty alcohol wax or wax-like dispersion matrix material) was such as to give a concentration of 80 weight % L-Carvone perfume dispersed in the C22 fatty alcohol wax or wax-like dispersion matrix of each micro-particle of the product composition. The size of the milling gap of the Sonic device was set to 20 thousand of an inch by turning the adjustment lever on top of the mill and the mill's water cooling was turned on. All feeding pipes of the mill were preheated with heating tape to approximately 80-90° C. The mill was switched on and the feed to the mill was started by opening the stopcock between funnel and mill inlet to allow the heated mixture contained in the feeding funnel to pass through the colloid mill within 30 seconds. The milled product was taken out of the mill and collected. The temperature of the cold water flowing through the mill's water cooling system had previously been adjusted such that the product exiting the mill had a temperature after the milling step of 60° C., which is 5° C. below the solidification point of 65° C. of each produced micro-particle having a concentration of 80 weight % L-Carvone perfume dispersed in the C22 fatty alcohol wax or wax-like dispersion matrix. The product composition of this Example contained a concentration of the produced micro-particles in their dispersion liquid of about 60 weight percent. Then this product composition comprising a plurality the micro-particles of the composition of the invention dispersed in the liquid in which they were colloid milled was further diluted 10× with water and a light microscopy photomicrograph slide was taken with magnification 400× and is shown in FIG. 33. A sample of this Example 7 product composition was then provided to Quantachrome GmbH and a size distribution curve of the micro-particles of the composition of the invention which is shown in FIG. 35 hereof was produced in the same way as for Example I. The % obscuration during the particle size measurement was 18%.

Example 8

In this process in accordance with the subject invention of Example 8 the high energy micro-particle producing machine used was a a FrymaKoruma Toothed Colloid Mill, Type MZ 80 available from FrymaKoruma AG, Switzerland, the FrymaKoruma Colloid Mill being provided with a water cooling jacket. A mixture of 900 g deionised water and 100 g Tween, preserved with 0.1% Nipagin M (Phase A), was heated in a beaker to 82° C. In a second beaker 900 g L-Carvone perfume (active) and 600 g C22 fatty alcohol wax or wax-like dispersion matrix material was heated to 90° C. and mixed to homogenity (Phase B). The solidification point of this Phase B composition comprising the C22 fatty alcohol wax or wax-like matrix with the L-Carvone perfume active dispersed therein is 71° C. The ratio of the above stated (Phase B) amount of perfume to C22 fatty alcohol wax or wax-like dispersion matrix material (900 g L-Carvone perfume to 600 g C22 fatty alcohol wax or wax-like dispersion matrix material) was such as to give a concentration of 60 weight % L-Carvone perfume dispersed in the C22 fatty alcohol wax or wax-like dispersion matrix of each micro-particle of the product composition. The heated phase A composition was filled into the Fryma colloid mill. The device was switched on to allow the heated Phase A composition containing inter alia the hot deionized water to recirculate through the mill. Then in a time period of 1 minute all the Phase B composition (wax or wax-like dispersion matrix with an active dispersed therein) was continuously poured into the mill containing the recirculating hot Phase A composition containing inter alia the deionized water. Then the Fryma's tap water cooling system was turned on to allow the combined contents of the mill of the Phase A composition plus the Phase B composition to cool down during the recirculating through the mill. After 4 min of running of the mill with its tap water cooling system in operation the temperature of the combination of Phase A plus Phase B in the mill dropped to 63° C., which is below the solidification point of 71° C. of each produced micro-particle having a concentration of 60 weight % L-Carvone perfume dispersed in the C22 fatty alcohol wax or wax-like dispersion matrix. The product dispersion was taken out of the mill and the device was switched off. The product composition of this Example contained a concentration of the produced micro-particles in their dispersion liquid of about 60 weight percent. Then this product composition comprising a plurality the micro-particles of the composition of the invention dispersed in the liquid in which they were colloid milled was further diluted 10× with water and a light microscopy photomicrograph slide was taken with magnification 400× and is shown in FIG. 34. A sample of this Example 8 product composition was then provided to Quantachrome GmbH and a size distribution curve of the micro-particles of the composition of the invention which is shown in FIG. 36 hereof was produced in the same way as for Example I hereof. The % obscuration during the particle size measurement was 18%.

Preferred features of the subject invention are listed below:
1. A micro-particle comprising a dispersion matrix with an active dispersed therein the micro-particle having a particle size of from 0.1 to 20 micrometers which provides for easy release of the active, wherein the dispersion matrix is a solid at a temperature of 21° C.
2. A micro-particle according to feature 1, which has a particle size from 0.1 to 10 micrometers, preferably from 0.5-10 micrometers, more preferably from 0.1 to 5 micrometers, yet more preferably from 1 to 10 micrometers, even more preferably from 1 to 7 micrometers, yet more preferably from 4 to 6 micrometers, even more preferably about 5 micrometers.
3. A micro-particle according to any preceding feature wherein the active is dispersed throughout the dispersion matrix.

4. A micro-particle according to any preceding feature wherein said active is easy releasable from the dispersion matrix at temperatures below the melting temperature of the dispersion matrix.
5. A micro-particle according to any preceding feature wherein said micro-particle comprises from 20 to 60 weight percent of said active, preferably from 25 to 40 weight percent of said active, more preferably from 28 to 32 weight percent of said active, yet more preferably about 30 weight percent of said active.
6. A micro-particle according to any preceding feature and wherein the active is substantially protected from oxidation.
7. A micro-particle according to any preceding feature wherein said dispersion matrix is formed from a wax or wax like material having the properties of water repellency and plasticity such as a C22 fatty alcohol.
8. A micro-particle according to any preceding feature wherein said dispersion matrix is formed from a wax or wax like material selected from animal waxes, beeswax; lanolin, shellac wax, vegetable wax, carnauba wax, candelilla wax, cutina wax, bayberry wax, ethylene-acrylic acid copolymer wax like materials; polyamide polymer wax like materials; polyethylene-vinyl acetate copolymer wax like materials, fatty alcohol wax like materials and a mixture of said fatty alcohol wax like materials with fatty acid(s) and/or fatty alcohol ethoxylate and/or polyethylene glycol, wax like edible oils, wax like edible fats, wax like fatty acid esters of monohydric alcohols and petroleum based wax like materials and alkane hydrocarbons and mixtures thereof.
9. A micro-particle according to feature 8 wherein said polyamide polymer wax like materials has a molecular weight in the range of from about 6,000 up to about 12,000, said petroleum based wax like materials are selected from paraffinic waxes with chemical formula $C_2H_{2n+2}$ where n=30 or more and microcrystalline waxes produced from heavy lubricating oil residues having a microcrystalline structure.
10. A micro-particle according to feature 8, wherein each said fatty alcohol(s) and said fatty acid(s) have 16-29 carbon atoms, more preferably 18-24 carbon atoms, wherein said fatty alcohol ethoxylate has 10-29 carbon atoms, preferably 14-20 carbon atoms with there being present 5-100 moles of ethylene oxide in each case, and wherein said polyethylene glycol has a molecular weight of 10-30,000 g per mole, more preferably 15,000-25,000 g per mole.
11. A micro-particle according to preceding feature wherein said micro-particle is either substantially rod shaped or substantially spherical.
12. A micro-particle according to any preceding feature wherein the micro-particle is non-frangible.
13. A composition comprising a plurality of the micro-particles according to any preceding feature and a dispersion liquid in which said micro-particles are dispersed.
14. A composition according to feature 13 wherein said dispersion liquid is selected from propylene glycol, a blend of surfactants suitable for use as a laundry detergent base, a blend of surfactants suitable for use as a fabric conditioner, glycerol, liquid paraffin oil dispersing agent, and liquid methyl silicone dispersing agent.
15. A composition according to feature 13 wherein said dispersion liquid comprises a blend of water and a surface tension lowering agent capable of lowering the surface tension of the water to 30 dynes/cm or less.
16. A composition according to feature 13 wherein said dispersion liquid is a blend of water and a surface tension lowering agent capable of lowering the surface tension of the water to 20 dynes/cm or less, preferably capable of lowering the surface tension of the water to 10 dynes/cm or less.
17. A composition according to any one of preceding features 13-16 wherein at least a majority of said micro-particles have a particle size from 0.1 to 20 micrometers, preferably from 0.1 to 10 micrometers, even more preferably from 0.1 to 5 micrometers, yet more preferably from 1 to 10 micrometers, even more preferably from 1 to 7 micrometers, yet more preferably from 4 to 6 micrometers, even more preferably about 5 micrometers.
18. A composition according to any one of preceding features 13-16 wherein at least 80% of said micro-particles have a particle size from 0.1 to 20 micrometers, preferably from 0.1 to 10 micrometers, even more preferably from 0.1 to 5 micrometers, yet more preferably from 1 to 10 micrometers, even more preferably from 1 to 7 micrometers, yet more preferably from 4 to 6 micrometers, even more preferably about 5 micrometers.
19. A composition according to any one of preceding features 13-16 wherein at least 90 percent of said micro-particles have a particle size from 0.1 to 20 micrometers, preferably from 0.1 to 10 micrometers, even more preferably from 0.1 to 5 micrometers, yet more preferably from 1 to 10 micrometers, even more preferably from 1 to 7 micrometers, yet more preferably from 4 to 6 micrometers, even more preferably about 5 micrometers.
20. A composition according to any one of preceding features 13-16 wherein substantially 100% of said micro-particles have a particle size from 0.1 to 20 micrometers, preferably from 0.1 to 10 micrometers, even more preferably from 0.1 to 5 micrometers, yet more preferably from 1 to 10 micrometers, even more preferably from 1 to 7 micrometers, yet more preferably from 4 to 6 micrometers, even more preferably about 5 micrometers.
21. A composition according to any one of preceding features 13-16 wherein said micro-particles have an average particle size from 3-7 micrometers preferably from 4-6 micrometers more preferably from 4.5-5.5 micrometers.
22. A composition according to any one of preceding features 13-21 wherein said micro-particles are present in said dispersion liquid in an amount of 0.05 to 60 weight percent.
23. A composition according to any one of preceding features 13-21 wherein said micro-particles are present in said dispersion liquid in an amount of 0.1 to 60 weight percent.
24. A composition according to any one of preceding features 13-21 wherein said micro-particles are present in said dispersion liquid in an amount of 0.1 to 40 weight percent.
25. A composition according to any one of preceding features 13-21 wherein said micro-particles are present in said dispersion liquid in an amount of 10 to 30 weight percent.

26. A process of preparing a micro-particle comprising the steps of:
    providing a composition comprising a dispersion matrix with an active dispersed therein wherein said dispersion matrix is a solid at a temperature of 21° C.;
    providing a dispersion liquid;
    providing a high shear micro-particle producing machine; combining said composition comprising said dispersion matrix with said active dispersed therein with said dispersion liquid and then processing said composition dispersion liquid combination in said high shear micro-particle producing machine to provide said micro-particle comprising said dispersion matrix with said active dispersed therein.
27. A process of preparing a micro-particle according to features 26 wherein said active is dispersed throughout said matrix.
28. A process of preparing a micro-particle according to any one of preceding features 26-27 wherein said high shear micro-particle producing machine is a colloid mill or a high shear mixer.
29. A process of preparing a micro-particle according to any one of preceding features 26-28 wherein said dispersion liquid is selected from propylene glycol, a blend of surfactants suitable for use as a laundry detergent base, a blend of surfactants suitable for use as a fabric conditioner and glycerol.
30. A process of preparing a micro-particle according to feature 29 wherein said process is an in-line process.
31. A process of preparing a micro-particle according to any one of preceding features 26-30 wherein said dispersion liquid comprises a surface tension lowering agent.
32. A process of preparing a micro-particle according to feature 31 wherein said dispersion liquid comprising said surface tension lowering agent comprises a blend of water and a surface tension lowering agent capable of lowering the surface tension of the water to 30 dynes/cm or less preferably capable of lowering the surface tension of the water to 20 dynes/cm or less, even more preferably capable of lowering the surface tension of the water to 10 dynes/cm or less.
33. A process of preparing a micro-particle according to feature 32 wherein said surface tension lowering agent is present in an amount of 0.5-10 weight percent.
34. A process of preparing a micro-particle according to any one of preceding features 31-33 wherein said surface tension lowering agent is either an ester of polyethoxylated sorbitan and oleic acid (Tween 80) or an ester of sorbitan and oleic acid.
35. A process of preparing a micro-particle according to any one of preceding features 31-34, wherein said process is a batch process.
36. A process of preparing a micro-particle according to any one of preceding features 26-35 wherein said composition comprising said dispersion matrix with said active dispersed therein is produced by means of the absorption of said active in liquid form in a solid or solid mixture, said solid or solid mixture comprising one or more surfactants and/or co-surfactants that are solid at 21° C., whereby the liquid active is dissolved in the solid or solid mixture at a temperature that lies above its solidification temperature, and then solidified by means of cooling of the solution, wherein the solid or the solid mixture forms said dispersion matrix.
37. A process of preparing a micro-particle according to any one of preceding features 26-36, wherein said dispersion matrix is formed from a wax or wax like material selected from animal waxes, beeswax; lanolin, shellac wax, vegetable wax, carnauba wax, candelilla wax, cutina wax, bayberry wax, ethylene-acrylic acid copolymer wax like materials; polyamide polymer wax like materials; polyethylene-vinyl acetate copolymer wax like materials, fatty alcohol wax like materials and a mixture of said fatty alcohol wax like materials with fatty acid(s) and/or fatty alcohol ethoxylate and/or polyethylene glycol, wax like edible oils, wax like edible fats, wax like fatty acid esters of monohydric alcohols and petroleum based wax like materials and alkane hydrocarbons and mixtures thereof.
38. A process of preparing a micro-particle according to feature 37 wherein said polyamide polymer wax like material has a molecular weight in the range of from about 6,000 up to about 12,000, and wherein said petroleum based wax like materials are selected from paraffinic waxes with chemical formula $C_2H_{2n+2}$ where n=30 or more and microcrystalline waxes produced from heavy lubricating oil residues having a microcrystalline structure.
39. A process of preparing a microparticle according to feature 37, wherein each said fatty alcohol(s) and said fatty acid(s) have 16-29 carbon atoms, more preferably 18-24 carbon atoms, wherein said fatty alcohol ethoxylate has 10-29 carbon atoms, preferably 14-20 carbon atoms with there being present 5-100 moles of ethylene oxide in each case, and wherein said polyethylene glycol has a molecular weight of 10-30,000 g per mole, more preferably 15,000-25,000 g per mole.
40. A process of preparing a micro-particle according to any one of preceding features 36-39, wherein 10 to 60 wt.-% of said active is dissolved in 90 to 40 wt.-% of a fatty alcohol C22, above its solidification point between 66 and 70° C., and then solidified by cooling the solution.
41. A process of preparing a micro-particle according to any one of preceding features 36-39, wherein 10 to 60 wt.-% of said active is dissolved in a mixture of 45 to 20 wt.-% of a fatty alcohol C22 and 45 to 20 wt.-% of a fatty acid, above a solidification point of the fatty alcohol/fatty acid mixture, and then solidified by cooling the solution.
42. A process of preparing a micro-particle according to any one of preceding features 36-39, wherein 10 to 60 wt.-% of said active is dissolved in a mixture of 45 to 20 wt.-% of a fatty alcohol C22 and 45 to 20 wt.-% of a fatty alcohol ethoxylate, above a solidification point of the fatty alcohol/fatty alcohol ethoxylate of 55 to 60° C., and then solidified by cooling the solution.
43. A process of preparing a micro-particle according to any one of preceding features 36-39 wherein 10 to 60 wt.-% of said active is dissolved in a mixture of 45 to 20 wt.-% of a fatty alcohol C22 and 45 to 20 wt.-% polyethylene glycol, above a solidification point of the fatty alcohol/polyethylene glycol mixture of 55 to 60° C., and then solidified by cooling the solution.
44. A process of preparing a micro-particle according to any one of features 26-43, said micro-particle having a particle size from 0.1 to 20 micrometers, preferably from 0.1-10 micrometers, more preferably from 0.1 to 5 micrometers, yet more preferably from 1 to 10 micrometers, even more preferably from 1 to 7 micrometers, yet more preferably from 4 to 6 micrometers, even more preferably about 5 micrometers.

45. A process of preparing a micro-particle according to any one of preceding features 26-44, wherein said micro-particle comprises from 20 to 60 weight percent of said active, preferably from 25 to 40 weight percent of said active, more preferably from 28 to 32 weight percent of said active, yet more preferably about 30 weight percent of said active.

46. A process of preparing a micro-particle according to any one of preceding features 26-45 wherein the active is easy releasable from the dispersion matrix at temperatures below the melting temperature of the dispersion matrix.

47. A process of preparing a micro-particle according to any one of preceding features 26-46 wherein said composition comprising said dispersion matrix with said active dispersed therein is either formed into a pastille or is formed into a block prior to being combined with said dispersion liquid.

48. A process of preparing a micro-particle according to any one of preceding features 26-47, wherein said composition comprising said dispersion matrix with said active dispersed therein is not melted prior to being combined with said dispersion liquid.

49. A process of preparing a micro-particle according to any one of preceding features 26-47 wherein said composition comprising said dispersion matrix with said active dispersed therein is melted prior to being combined with said dispersion liquid.

50. A process of preparing a micro-particle according to any one of preceding features 26-49 wherein said composition comprising said dispersion matrix with said active dispersed therein is shaped into a particle having a particle size of 0.5-7 mm and is then ground prior to being combined with said dispersion liquid whereby said particle having a particle size of 0.5-7 mm is combined with a grinding liquid to form a particle/grinding liquid combination which is then mechanically ground in a grinding machine.

51. A process according to any one of features 26-50, wherein a plurality of said micro-particles are produced.

52. A process according to feature 51 comprising the further step of collecting said plurality of micro-particles dispersed in said dispersion liquid as a product of the process.

53. A process according to feature 52 wherein at least a majority of said plurality of micro-particles have a particle size from 0.1 to 20 micrometers, preferably from 0.1 to 10 micrometers, even more preferably from 0.1 to 5 micrometers, yet more preferably from 1 to 10 micrometers, even more preferably from 1 to 7 micrometers, yet more preferably from 4 to 6 micrometers, even more preferably about 5 micrometers.

54. A process according to feature 52 wherein at least 80% of said plurality of micro-particles have a particle size from 0.1 to 20 micrometers, preferably from 0.1 to 10 micrometers, even more preferably from 0.1 to 5 micrometers, yet more preferably from 1 to 10 micrometers, even more preferably from 1 to 7 micrometers, yet more preferably from 4 to 6 micrometers, even more preferably about 5 micrometers.

55. A process according to feature 52 wherein at least 90% of said plurality of micro-particles have a particle size from 0.1 to 20 micrometers, preferably from 0.1 to 10 micrometers, even more preferably from 0.1 to 5 micrometers, yet more preferably from 1 to 10 micrometers, even more preferably from 1 to 7 micrometers, yet more preferably from 4 to 6 micrometers, even more preferably about 5 micrometers.

56. A process according to feature 52 wherein substantially 100% of said plurality of micro-particles have a particle size from 0.1 to 20 micrometers, preferably from 0.1 to 10 micrometers, even more preferably from 0.1 to 5 micrometers, yet more preferably from 1 to 10 micrometers, even more preferably from 1 to 7 micrometers, yet more preferably from 4 to 6 micrometers, even more preferably about 5 micrometers.

57. A process according to any one of preceding features 52-56 wherein said micro-particles are present in said dispersion liquid in an amount of 0.05 to 60 weight percent.

58. A process according to any one of preceding features 52-56 wherein said micro-particles are present in said dispersion liquid in an amount of 0.1 to 60 weight percent.

59. A process according to any one of preceding features 52-56 wherein said micro-particles are present in said dispersion liquid in an amount of 0.1 to 40 weight percent.

60. A process according to any one of preceding features 52-56 wherein said micro-particles are present in said dispersion liquid in an amount of 10 to 30 weight percent.

61. A process according to any one of features 26-60, wherein said composition comprising said dispersion matrix with said active dispersed therein is a non-frangible composition.

62. A micro-particle comprising a dispersion matrix with an active dispersed therein prepared by the process of any one of preceding features 26-50 and 61 when depending on said features 26-50.

63. A composition comprising a plurality of micro-particles and a dispersion liquid in which said micro-particles are dispersed prepared by the process of any one of preceding features 51-61.

The invention claimed is:
1. A process of preparing a composition comprising a plurality of micro-particles and a dispersion liquid in which said micro-particles are dispersed comprising the steps of:
providing a high energy micro-particle producing machine comprising a micro-particle producing assembly within a cooling system;
providing a combination of dispersion liquid, an active and a wax material at such a temperature that the active and the wax material of the combination is in molten form;
passing said combination into said cooling system whilst said micro-particle producing assembly is operating to disperse said active and said wax material of the combination in molten form in said dispersion liquid then while said micro-particle producing assembly is kept operating, cooling said combination in said cooling system to below the solidification temperature of the micro-particles such that cooling of the combination occurs while said micro-particle producing assembly is operating to disperse said active and said wax components so that cooling occurs at the same time as micro-particle formation to produce a composition comprising a plurality of solid micro-particles dispersed in said dispersion liquid before said micro-particles dispersed in said dispersion liquid leave said cooling system, said micro-particles comprising a wax dispersion matrix with said active dispersed therein.

2. A process according to claim 1, wherein said high energy micro-particle producing machine further comprises a feeding assembly and means for providing fluid flow communication between said feeding assembly and said micro-particle producing assembly, said high energy micro-particle producing machine further comprising means for opening and closing said fluid flow between said feeding assembly and said micro-particle producing assembly.

3. A process according to claim 2, wherein said combination of said dispersion liquid, said active and said wax material are provided in said feeding assembly at such a temperature that the active and the wax material are melted with fluid flow between said feeding assembly and said micro-particle producing assembly closed and then said fluid flow is opened.

4. A process according to claim 2, wherein said feeding assembly comprises heating means for melting or keeping melted said active and said wax material of said combination.

5. A process according to claim 2, wherein said means for providing fluid flow communication further comprises insulating means for keeping said active and said wax material of said combination melted during flow.

6. A process according to claim 1, comprising the additional steps of recycling said composition comprising said plurality of micro-particles dispersed in said dispersion liquid through the micro-particle producing assembly one or more times whilst cooling is continued such that said composition comprises further micro-particles resulting from cooling of the composition dispersed in said dispersion liquid.

7. A process according to claim 1, wherein said composition is diluted with a dilution liquid after said composition has left said high energy micro-particle producing machine for the final time.

8. A process according to claim 7, wherein said dilution liquid is selected from the group consisting of propylene glycol, a blend of surfactants suitable for use as a laundry detergent base, a blend of surfactants suitable for use as a fabric conditioner, glycerol, water, a combination of water and a surface tension lowering agent and mixtures of two or more thereof.

9. A process according to claim 8, wherein said dilution liquid is colder than said composition.

10. A process according to claim 1, wherein said composition is further cooled by a cooled heat exchanger after said composition has left said high energy micro-particle producing machine for the final time.

11. A process according to claim 6, wherein said a high energy micro-particle producing machine is provided with a temperature regulating assembly for controlling the temperature of said combination as it passes through said micro-particle producing assembly.

12. A process according to claim 11, wherein said temperature regulating assembly is operated during a first step of operation to hold the temperature of said combination at such a first temperature that said active and said wax material of the combination are kept melted when said combination is passed into said micro-particle producing assembly and then is operated during a second step of operation to hold the temperature of said combination at such a second temperature that said plurality of micro-particles are produced by cooling said combination to a temperature below the solidification temperature of each of said micro-particles before each said micro-particle dispersed in said dispersion liquid leaves said micro-particle producing assembly.

13. A process according to claim 11, wherein said temperature regulating assembly is a cooling jacket which provides said cooling of said combination to a temperature below the solidification temperature of each of said micro-particles before each said micro-particle leaves said micro-particle producing assembly.

14. A process according to claim 1, wherein said cooling is provided by introducing additional dispersion liquid into said micro-particle producing assembly at a sufficiently low temperature to cool said combination to a said temperature below said solidification temperature of each of said micro-particles.

15. A process according to claim 1, wherein said high energy micro-particle producing machine is a colloid mill equipped with a feeding funnel.

16. A process according to claim 15, wherein said feeding funnel is equipped with an immersion heater and a stirrer.

17. A process according to claim 15, wherein said colloid mill is equipped with a stopcock downstream from its feeding funnel.

18. A process according to claim 1, wherein said dispersion liquid is selected from the group consisting of propylene glycol, a blend of surfactants suitable for use as a laundry detergent base, a blend of surfactants suitable for use as a fabric conditioner and glycerol and mixtures of two or more thereof.

19. A process according to claim 18, wherein said process is an in-line process where said produced composition comprising a plurality of micro-particles dispersed in said dispersion liquid is fed into a line of a further process.

20. A process according to claim 1, wherein said dispersion liquid comprises a surface tension lowering agent.

21. A process according to claim 20, wherein said process is a batch process wherein said composition comprising a plurality of solid micro-particles dispersed in said dispersion liquid is collected batch wise as a final product of said process, or an in-line process.

22. A process according to claim 1, wherein each said micro-particle comprises from 20 to 80 weight percent of said active.

23. A process according to claim 1, further comprising a step of collecting said plurality of solid micro-particles dispersed in said dispersion liquid as a product of the process.

24. A process according to claim 1, wherein the active is selected from the group consisting of botanical extracts including essential oils, other perfumes and mixtures of two or more thereof.

25. A process according to claim 1, wherein each of the wax material and the dispersion matrix of the micro-particle is a C22 fatty alcohol.

26. A process according to claim 1, wherein said high energy micro-particle producing machine comprising said micro-particle producing assembly is a high energy rotor-stator machine comprising a rotor-stator assembly.

27. A process according to claim 1, wherein said micro-particle producing assembly comprises an orifice, a means for forcing said combination through said orifice and a surface downstream from said orifice whereby said combination is forced through said orifice to strike said surface at a velocity of at least 300 ft/sec.

28. A process according to claim 27, wherein said means for forcing said combination through said orifice is a pump.

29. A process according to claim 27, wherein said surface can withstand pressures of up to 5000 psi.

30. A process according to claim 1, wherein said high energy micro-particle producing machine comprises a rotating mixing portion and a stationary surface surrounding said rotating mixing portion whereby said rotating mixing portion forces said combination towards said stationary surface with such a force that said combination is accelerated to a velocity of at least 300 ft/sec before striking said surface.

31. The process according to claim 1, wherein the cooling of said combination in said cooling system occurs at a temperature below 65° C.

\* \* \* \* \*